(12) United States Patent
Avantaggiati et al.

(10) Patent No.: US 12,016,834 B2
(45) Date of Patent: Jun. 25, 2024

(54) SMALL MOLECULE INHIBITORS OF SLC25A1

(71) Applicants: GEORGETOWN UNIVERSITY, Washington, DC (US); GEORGE MASON UNIVERSITY, Fairfax, VA (US)

(72) Inventors: Maria Laura Avantaggiati, Kensington, MD (US); Mikell Paige, Fairfax, VA (US)

(73) Assignees: Georgetown University, Washington, DC (US); George Mason University, Fairfax, VA (US)

( * ) Notice: Subject to any disclaimer, the term of this patent is extended or adjusted under 35 U.S.C. 154(b) by 31 days.

(21) Appl. No.: 16/636,226

(22) PCT Filed: Aug. 3, 2018

(86) PCT No.: PCT/US2018/045156
§ 371 (c)(1),
(2) Date: Feb. 3, 2020

(87) PCT Pub. No.: WO2019/028343
PCT Pub. Date: Feb. 7, 2019

(65) Prior Publication Data
US 2020/0246285 A1 Aug. 6, 2020

Related U.S. Application Data

(60) Provisional application No. 62/540,725, filed on Aug. 3, 2017.

(51) Int. Cl.
*A61K 31/18* (2006.01)
*A61P 35/04* (2006.01)
*A61K 45/06* (2006.01)

(52) U.S. Cl.
CPC .............. *A61K 31/18* (2013.01); *A61P 35/04* (2018.01); *A61K 45/06* (2013.01)

(58) Field of Classification Search
None
See application file for complete search history.

(56) References Cited

U.S. PATENT DOCUMENTS

| 5,451,677 A | 9/1995 | Fisher et al. |
| 7,119,120 B2 | 10/2006 | Jozefiak et al. |
| 2010/0035940 A1 | 2/2010 | Ostrov et al. |

FOREIGN PATENT DOCUMENTS

| WO | WO 2007/076055 A2 * | 7/2007 | ............. A61K 31/44 |
| WO | WO 2017/162834 A1 * | 9/2017 | ............. A61K 31/41 |

OTHER PUBLICATIONS

Woolley et al., CAS SciFinder (database CAPLUS, Acc. No. 1963:29288) abstract of Biochemical Pharmacology (1962), 11(12), pp. 1163-1173.*
Woolley et al., Biochemical Pharmacology (1962), vol. 11, pp. 1163-1173.*
PCT/US2018/045156 , "International Preliminary Report on Patentability", dated Feb. 13, 2020, 7 pages.
Fernandez, et al., "The Mitochondrial Citrate Carrier, SLC25A1, Drives Stemness and Therapy Resistance in Non-Small Cell Lung Cancer", Cell Death & Differentiation, vol. 25, Apr. 12, 2018, pp. 1239-1258.
Kolukula, et al., "SLC25A1, or CIC, is A Novel Transcriptional Target of Mutant p53 and a Negative Tumor Prognostic Marker", Oncotarget., vol. 5, Issue 5, Mar. 15, 2014, pp. 1212-1225.
International Application No. PCT/US2018/045156, "International Search Report and Written Opinion", dated Oct. 16, 2018, 10 pages.

\* cited by examiner

*Primary Examiner* — Brian J Davis
(74) *Attorney, Agent, or Firm* — Kilpatrick Townsend & Stockton LLP

(57) ABSTRACT

Methods of treating or preventing cancer, diabetes, and/or obesity in a subject are provided. The methods comprise administering to a subject a therapeutically effective amount of an SLC25A1 inhibitor as described herein. Also provided herein are pharmaceutical compositions comprising an SLC25A1 inhibitor and a chemotherapeutic agent. Further provided herein are methods of inhibiting SLC25A1 in a cell.

13 Claims, 52 Drawing Sheets
Specification includes a Sequence Listing.

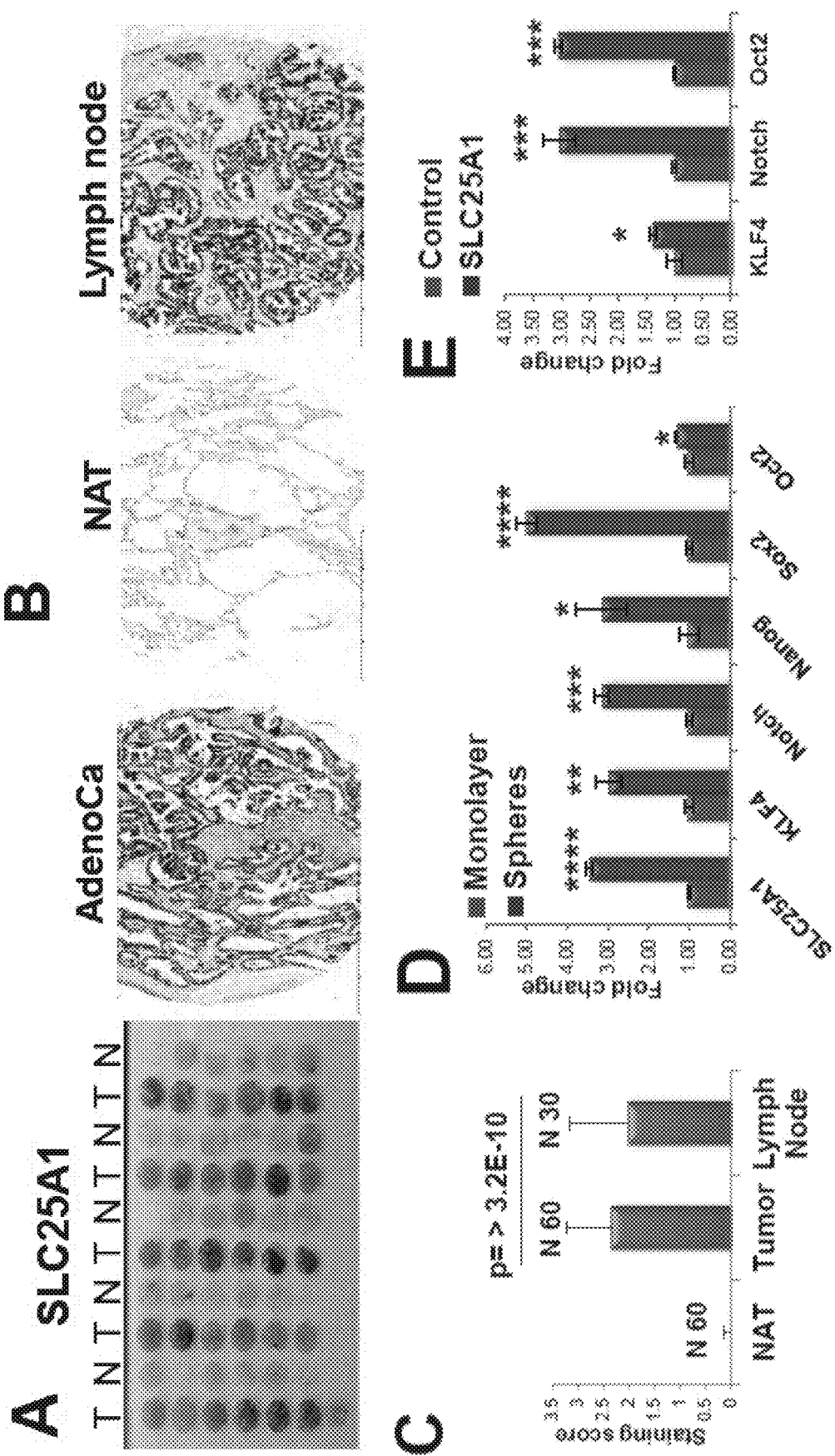
Figures 1A-E

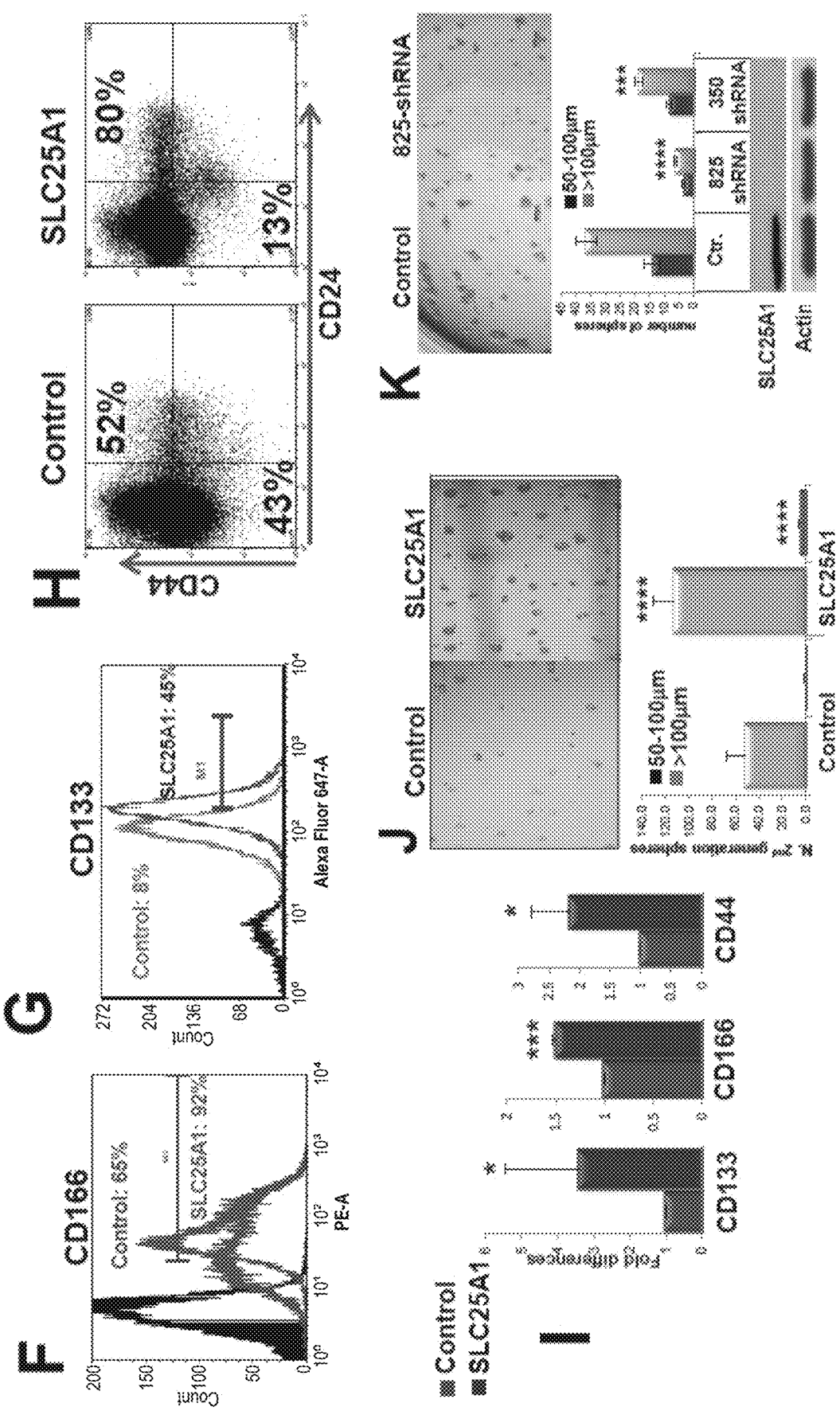
Figures 1F-K

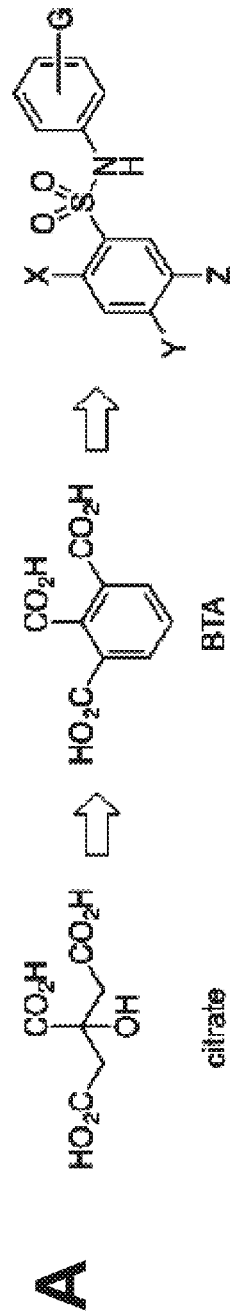
Comparison of SLC25A1 inhibitors
| Compond | X | Y | Z | G | $^a$log P | $^b$TPSA (Å$^2$) | $^c$K$_D$ (μM) | Docking Score |
|---|---|---|---|---|---|---|---|---|
| Citrate | N/A | N/A | N/A | N/A | -1.25 | 132.1 | N/D | -34.187920 |
| BTA | N/A | N/A | N/A | N/A | 0.78 | 111.9 | N/D | -32.761131 |
| CTPI-1 | Cl | H | CO2H | 3-NO2 | 3.64 | 140.7 | 63.6 | -40.476402 |
| CTPI-2 | H | Cl | NO2 | 2-CO2H | 3.64 | 140.7 | 5.3 | -62.963432 |
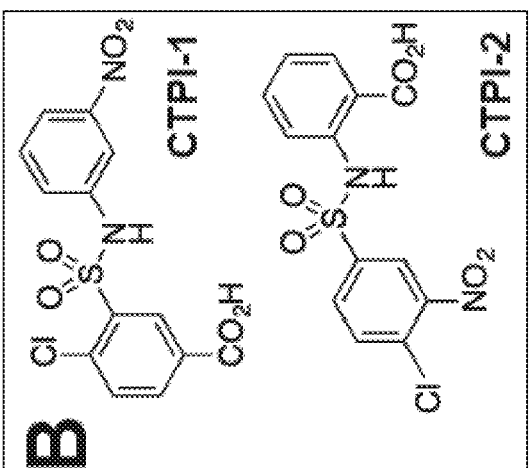
Figures 2A-B

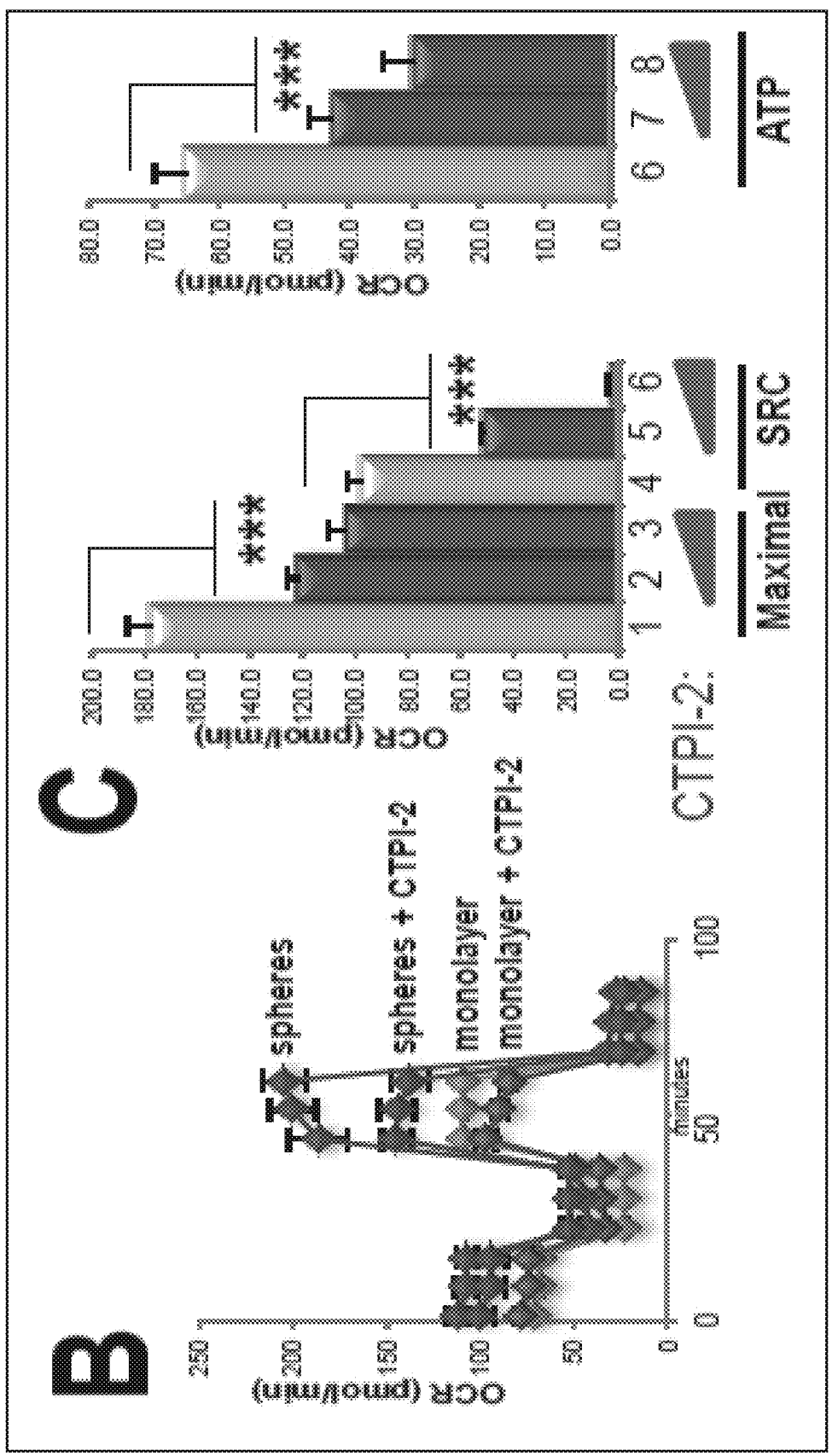
Figures 3B-C

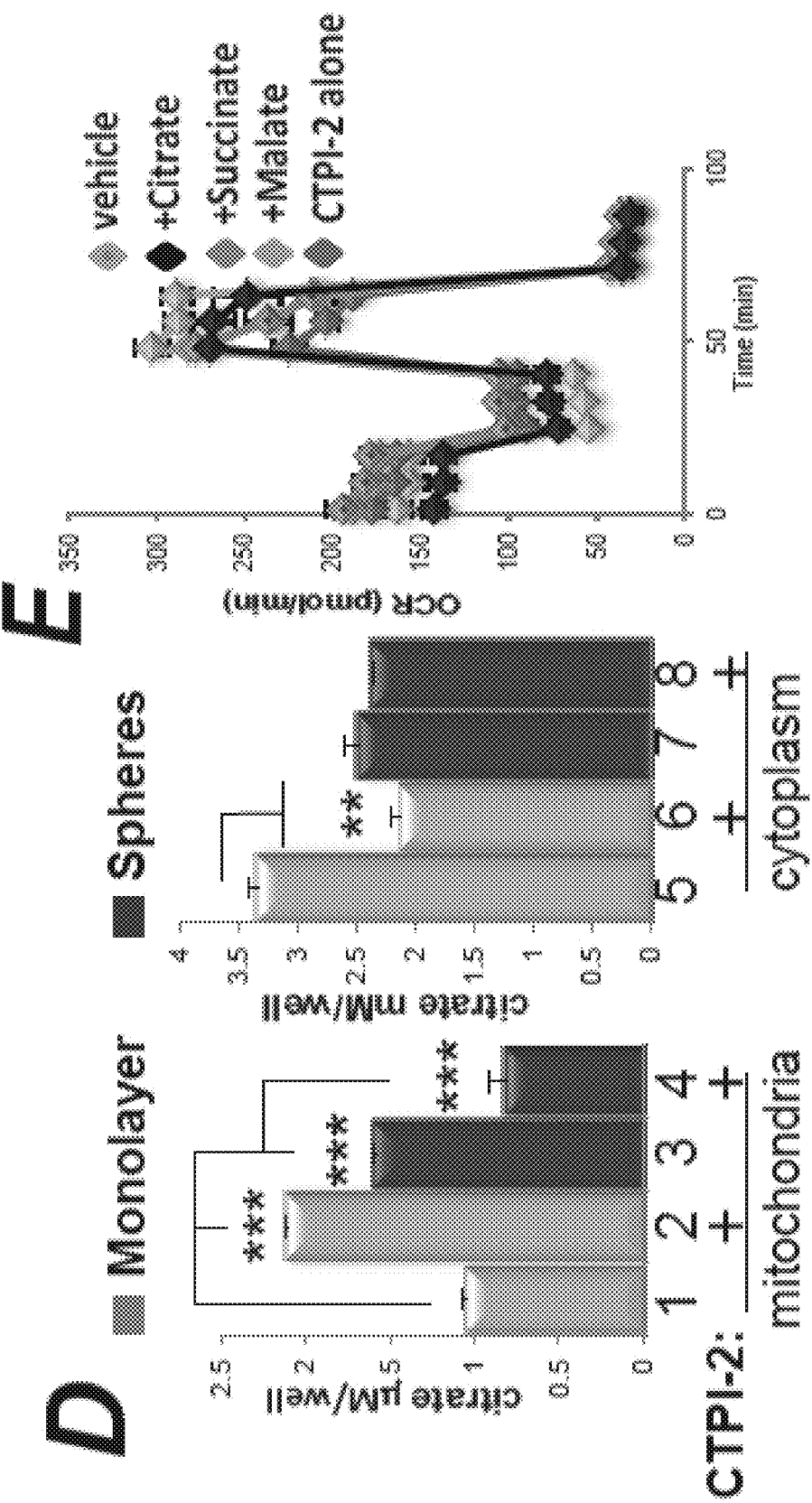
Figures 3D-E

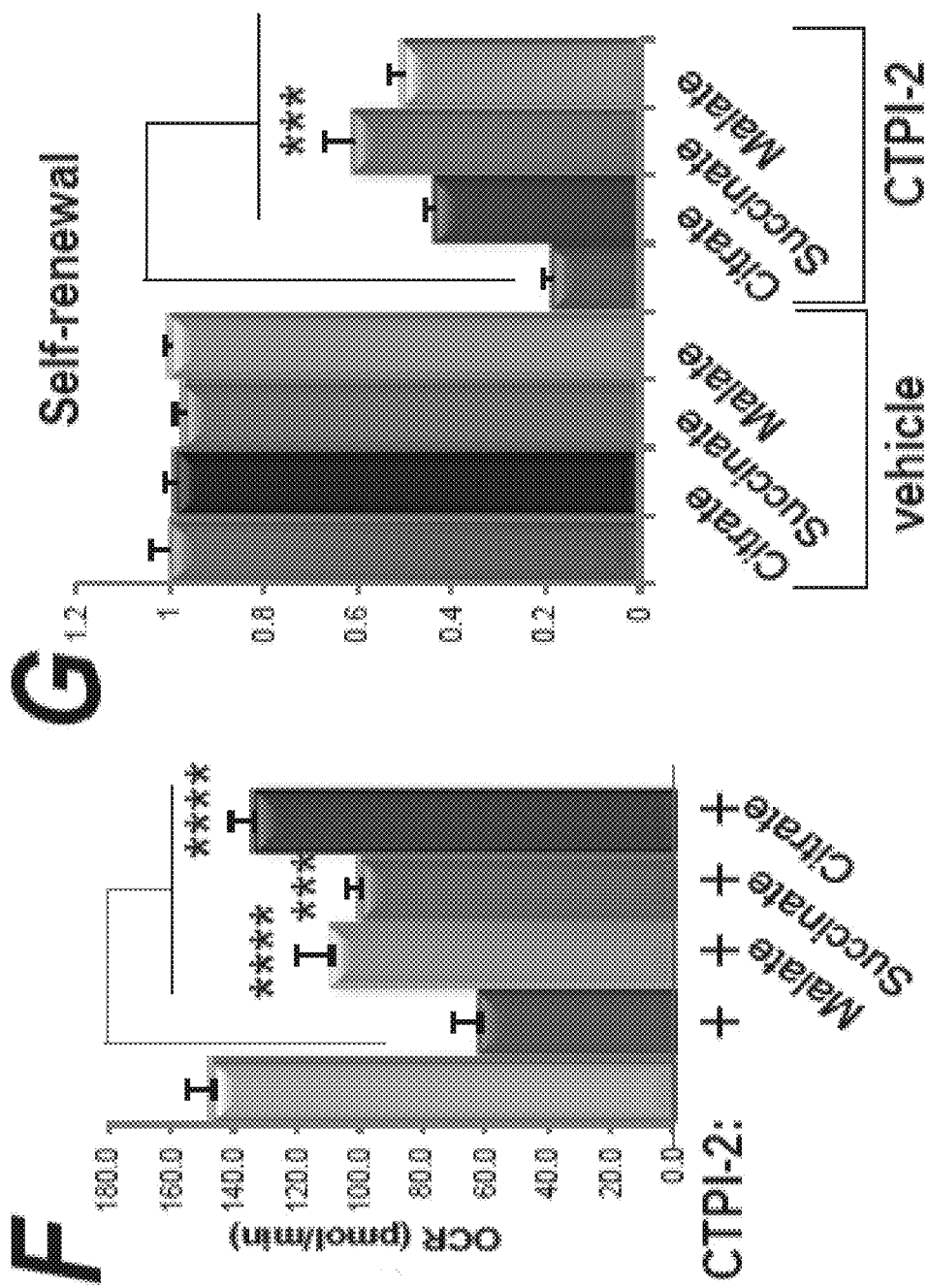
Figures 3F-G

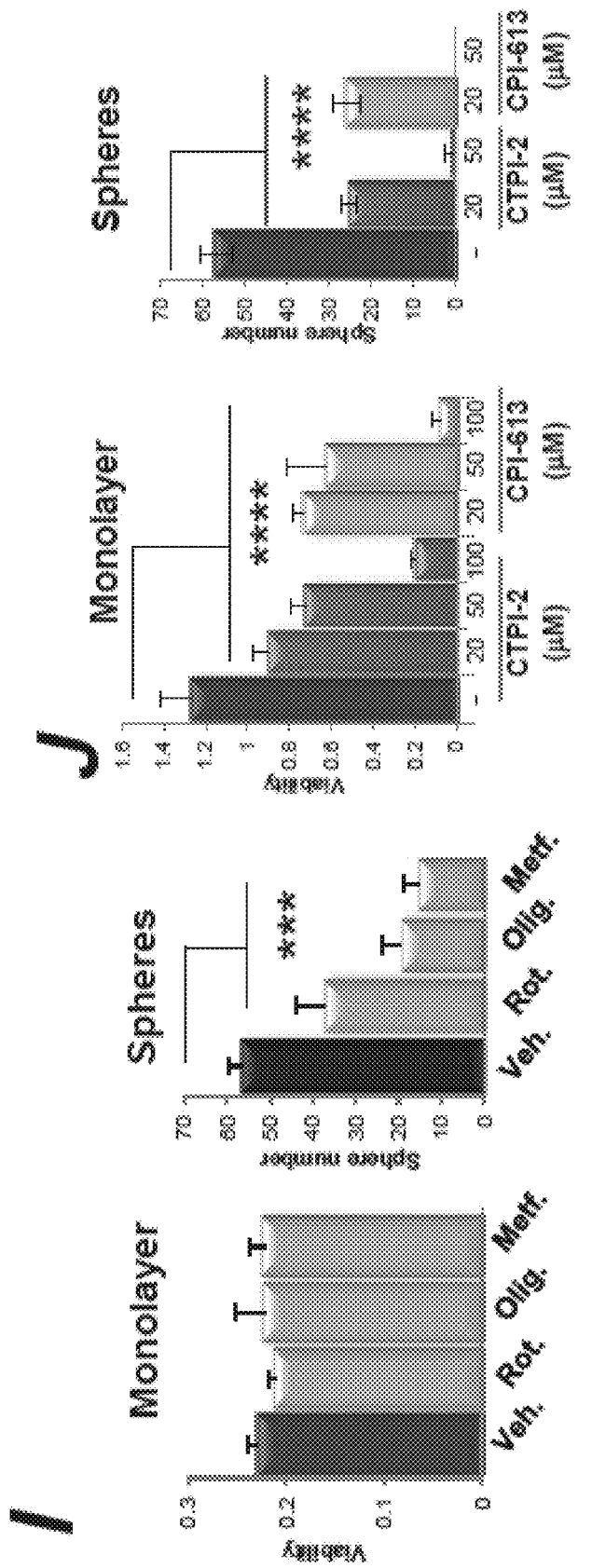
Figures 3I-J

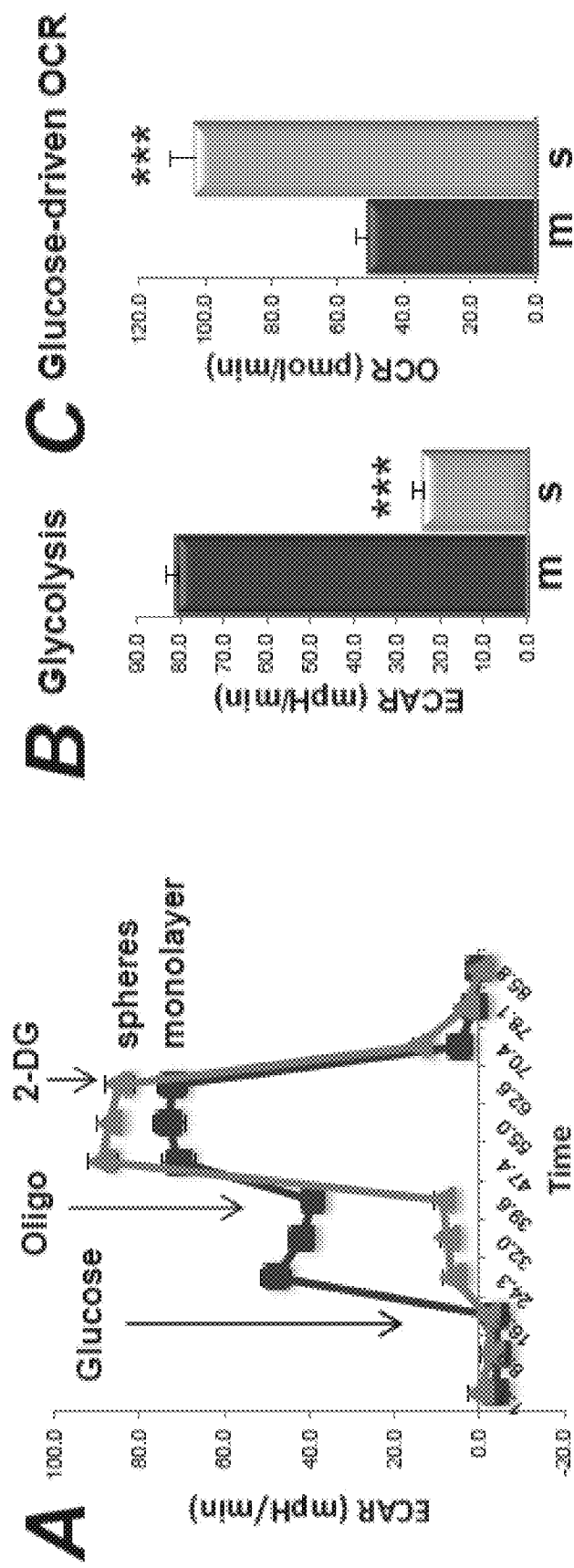
Figures 4A-C

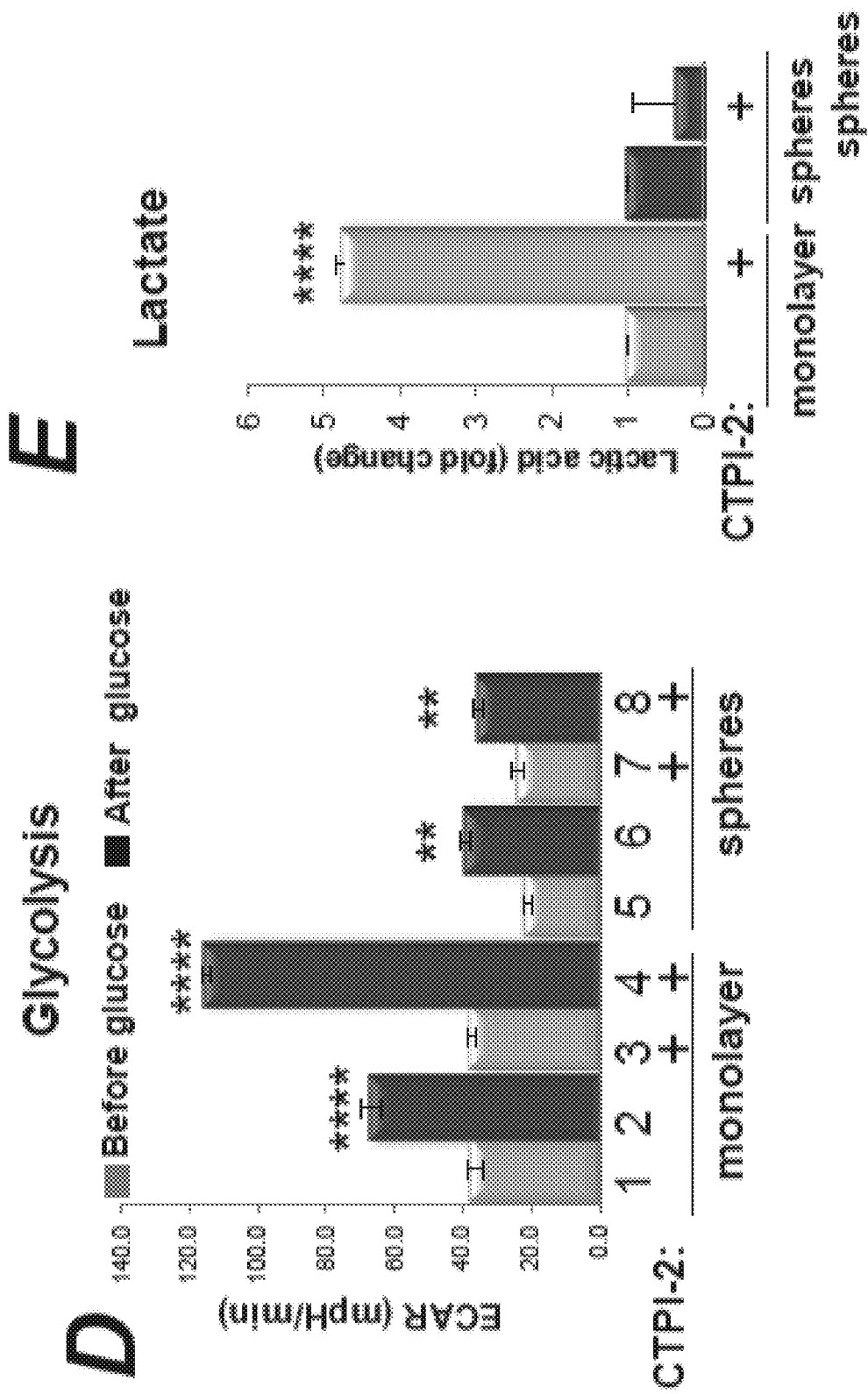
Figures 4D-E

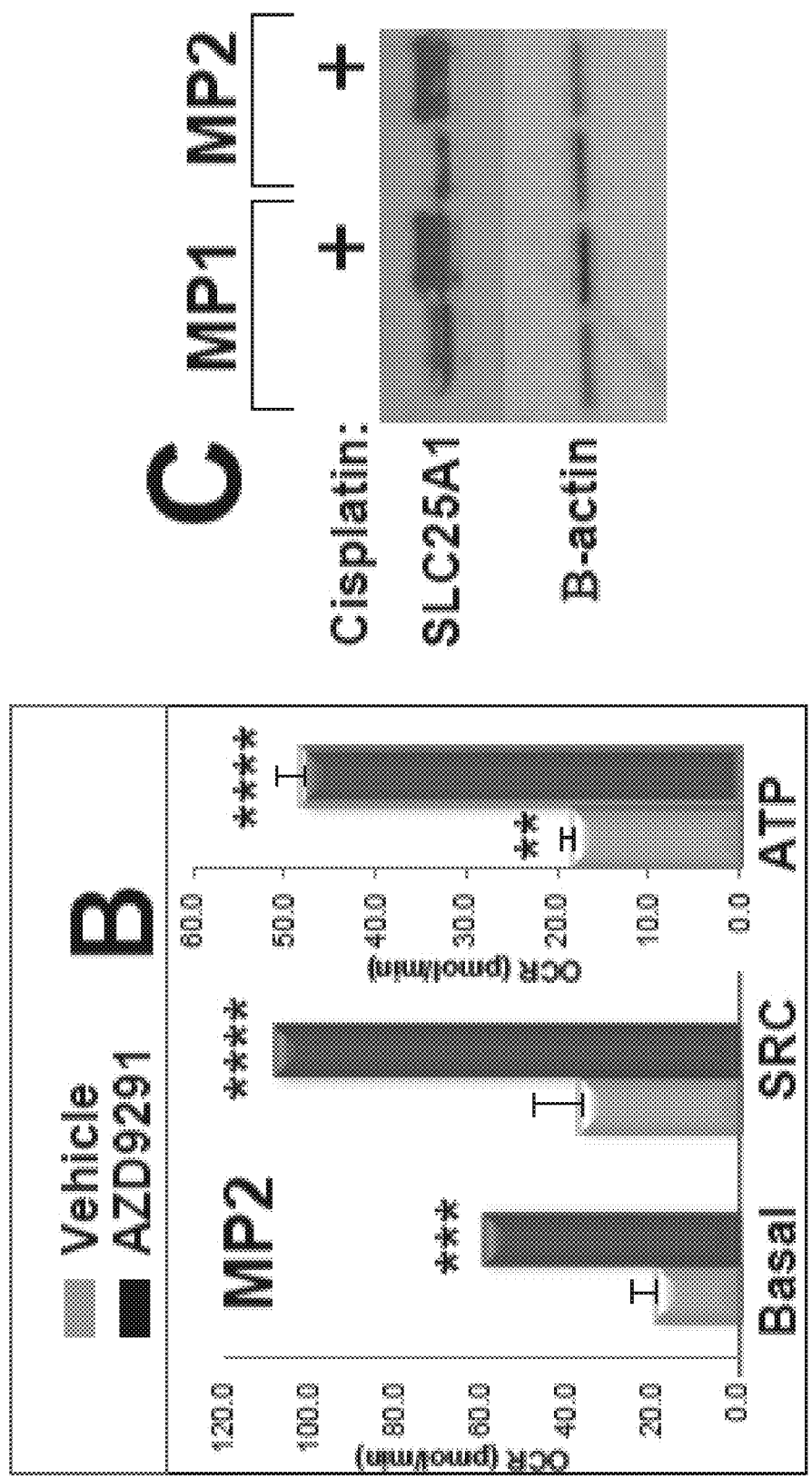
Figures 6B-C

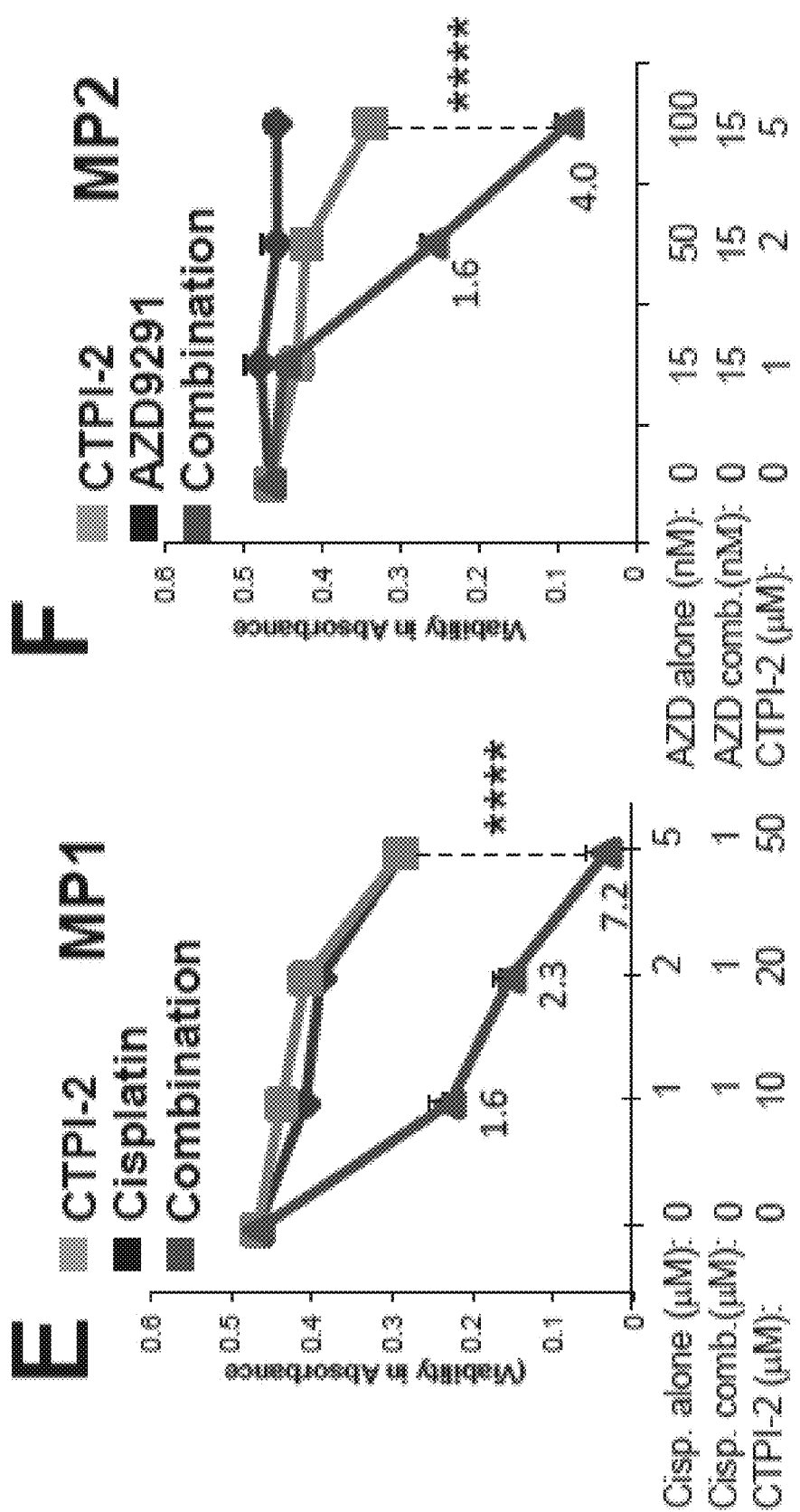
Figures 6E-F

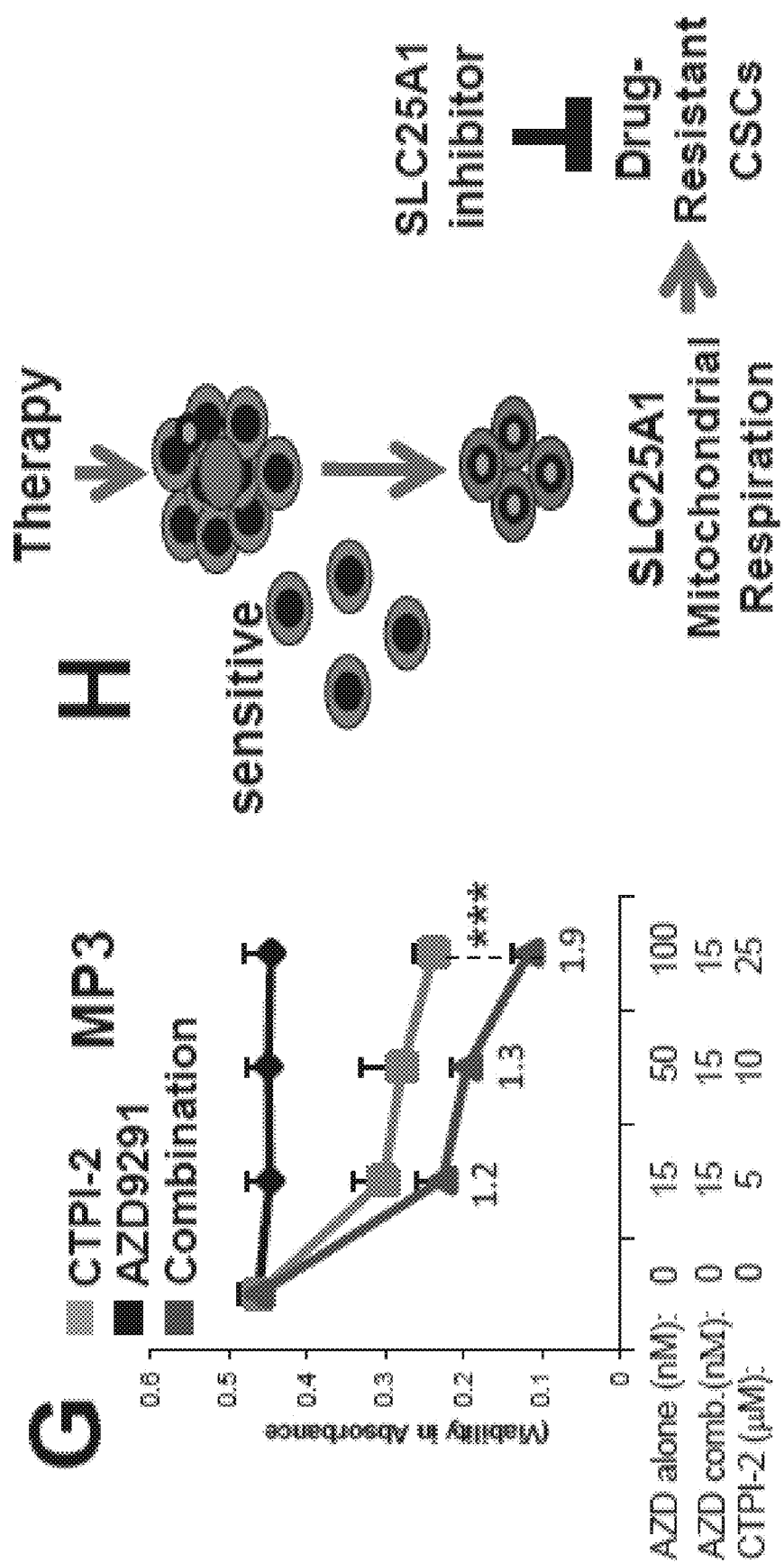
Figures 6G-H

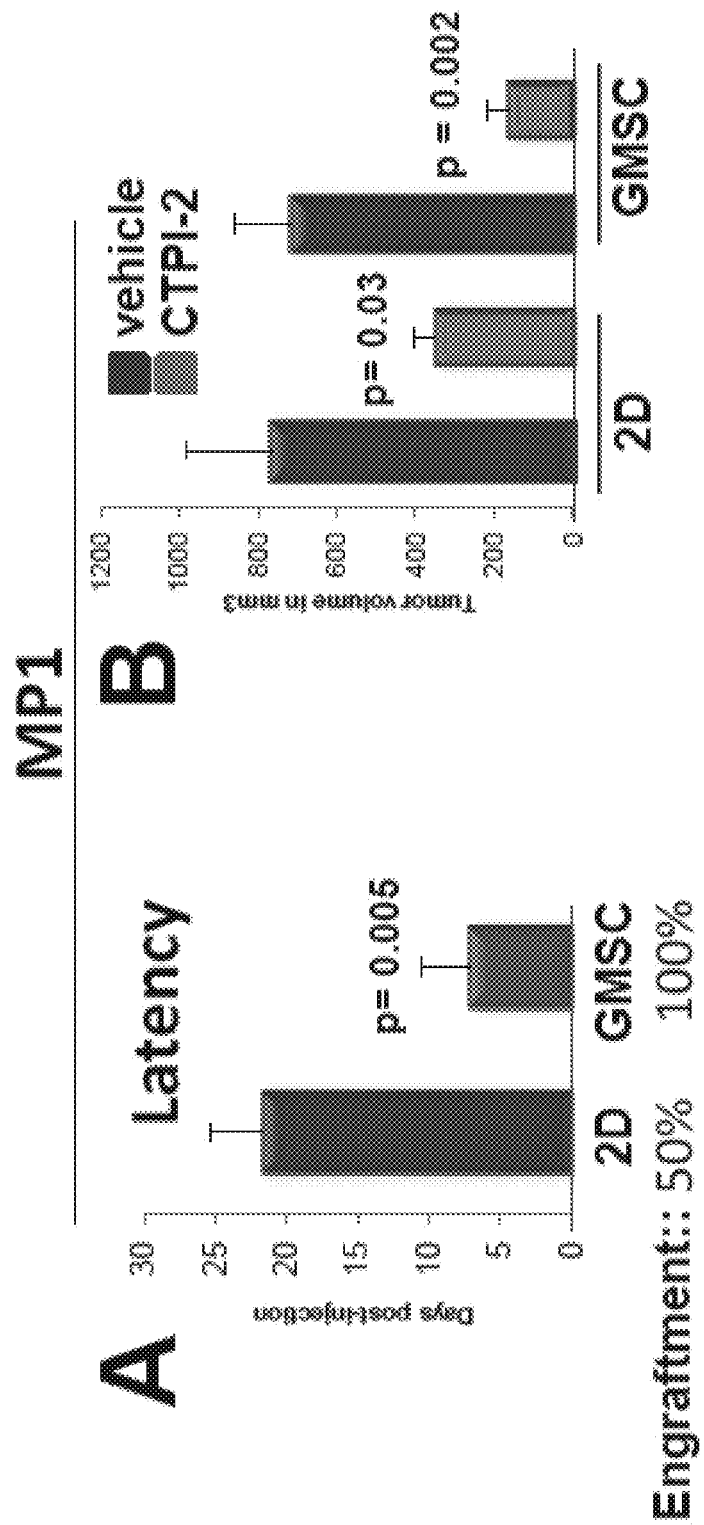
Figures 7A-B

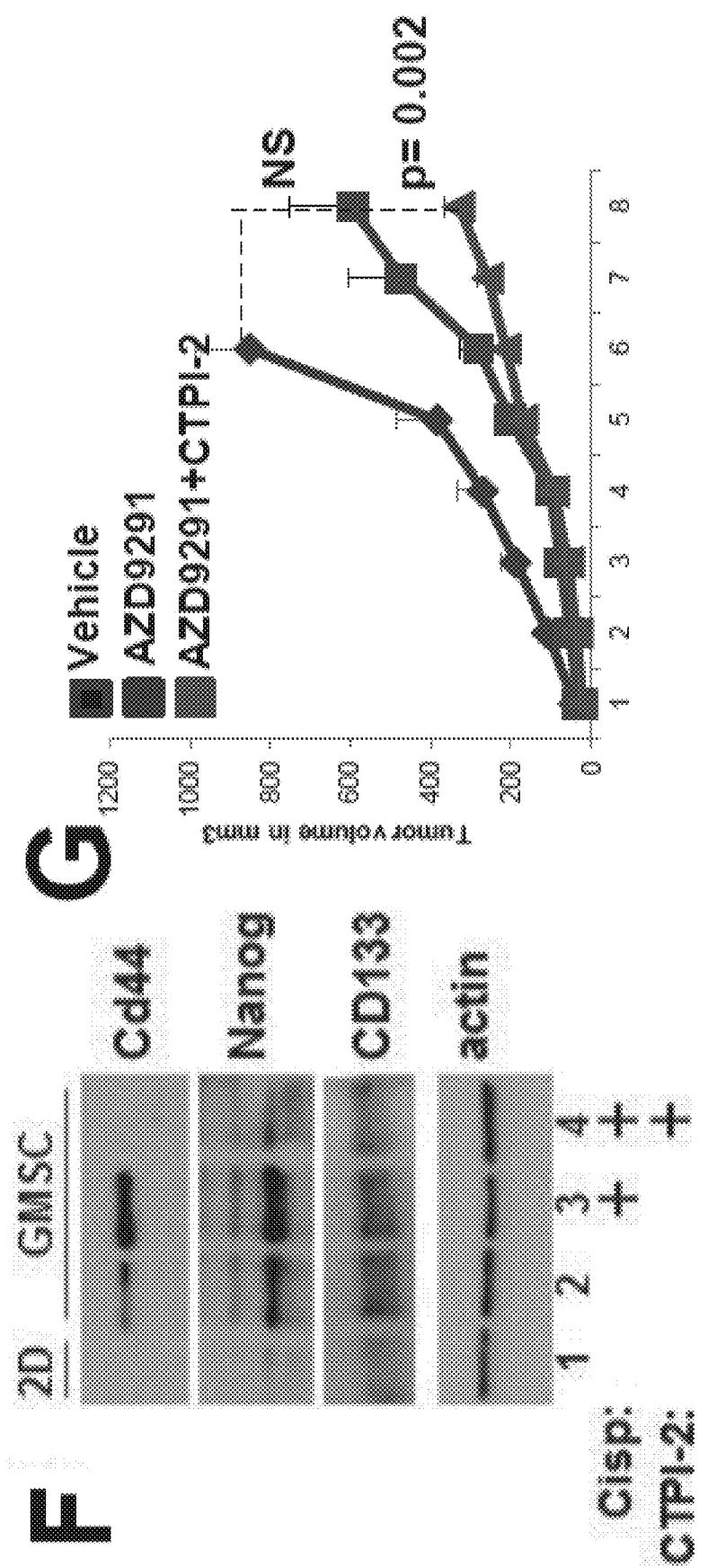
Figures 7F-G

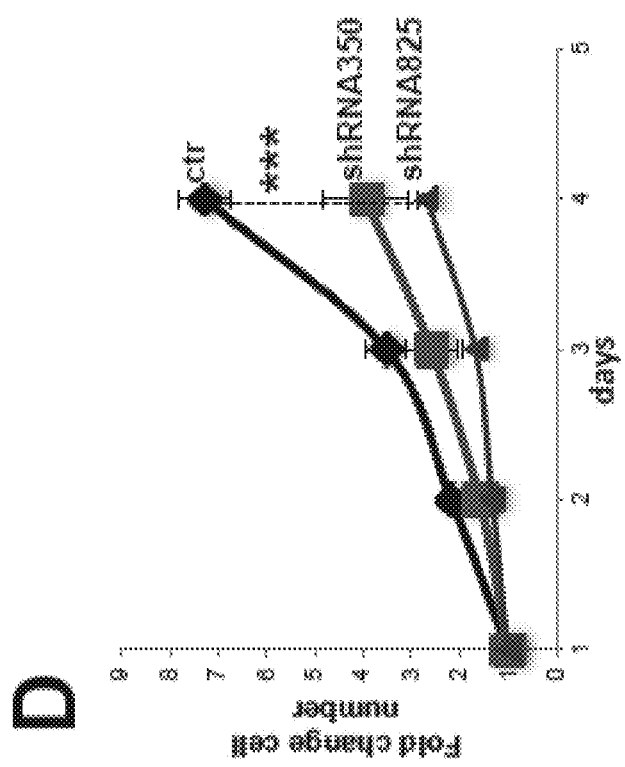
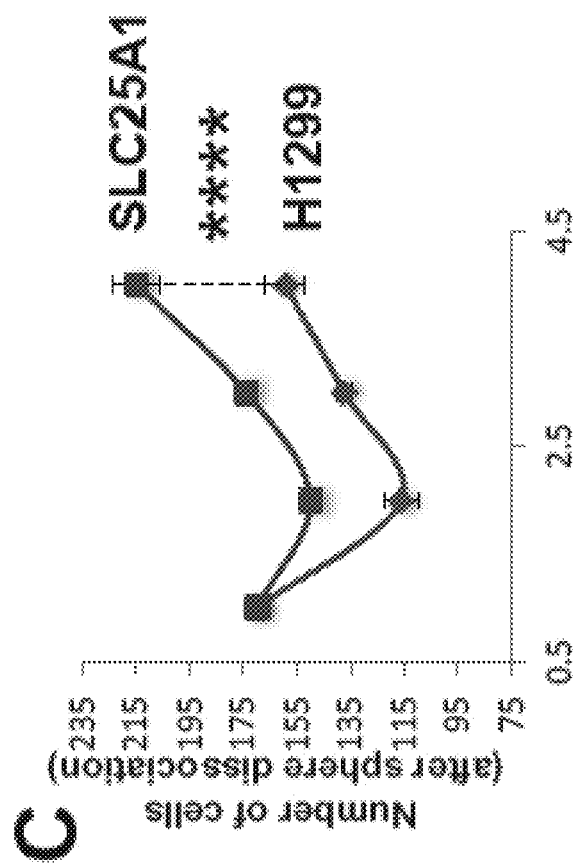
Figures 9C-D

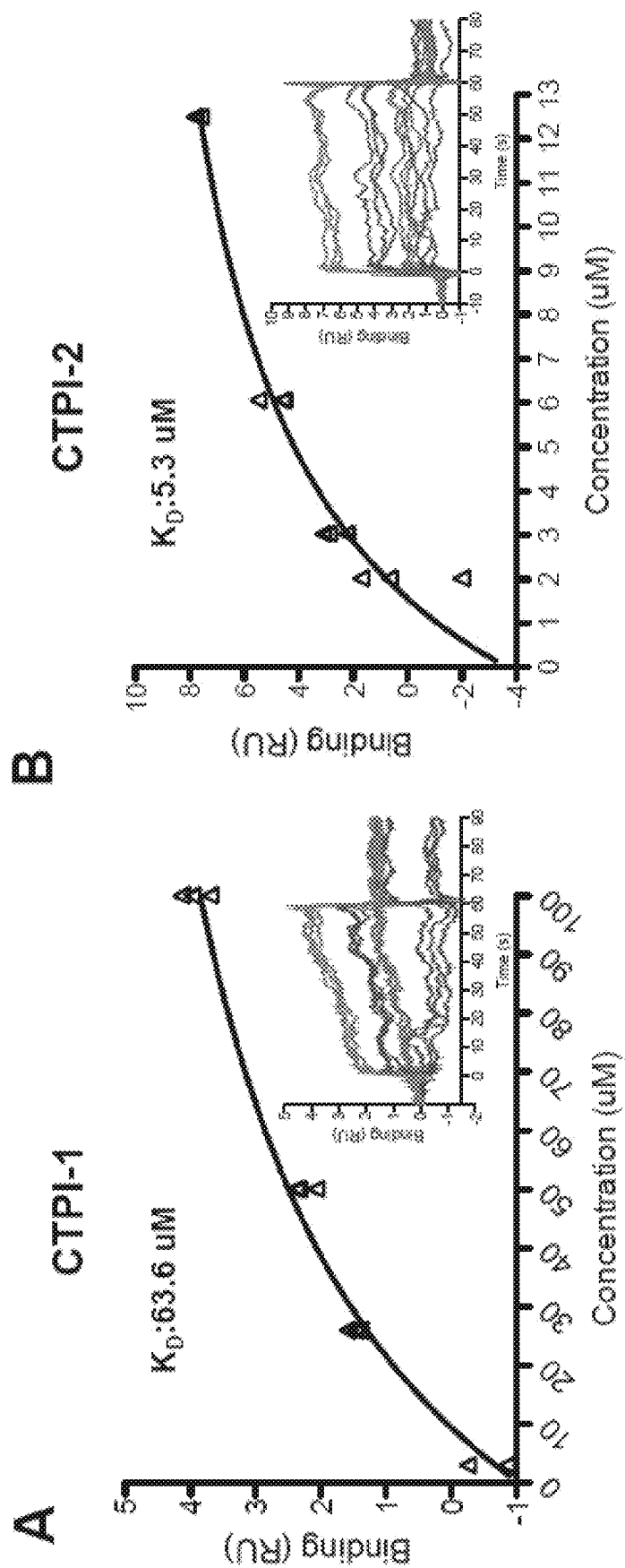
Figures 10A-B

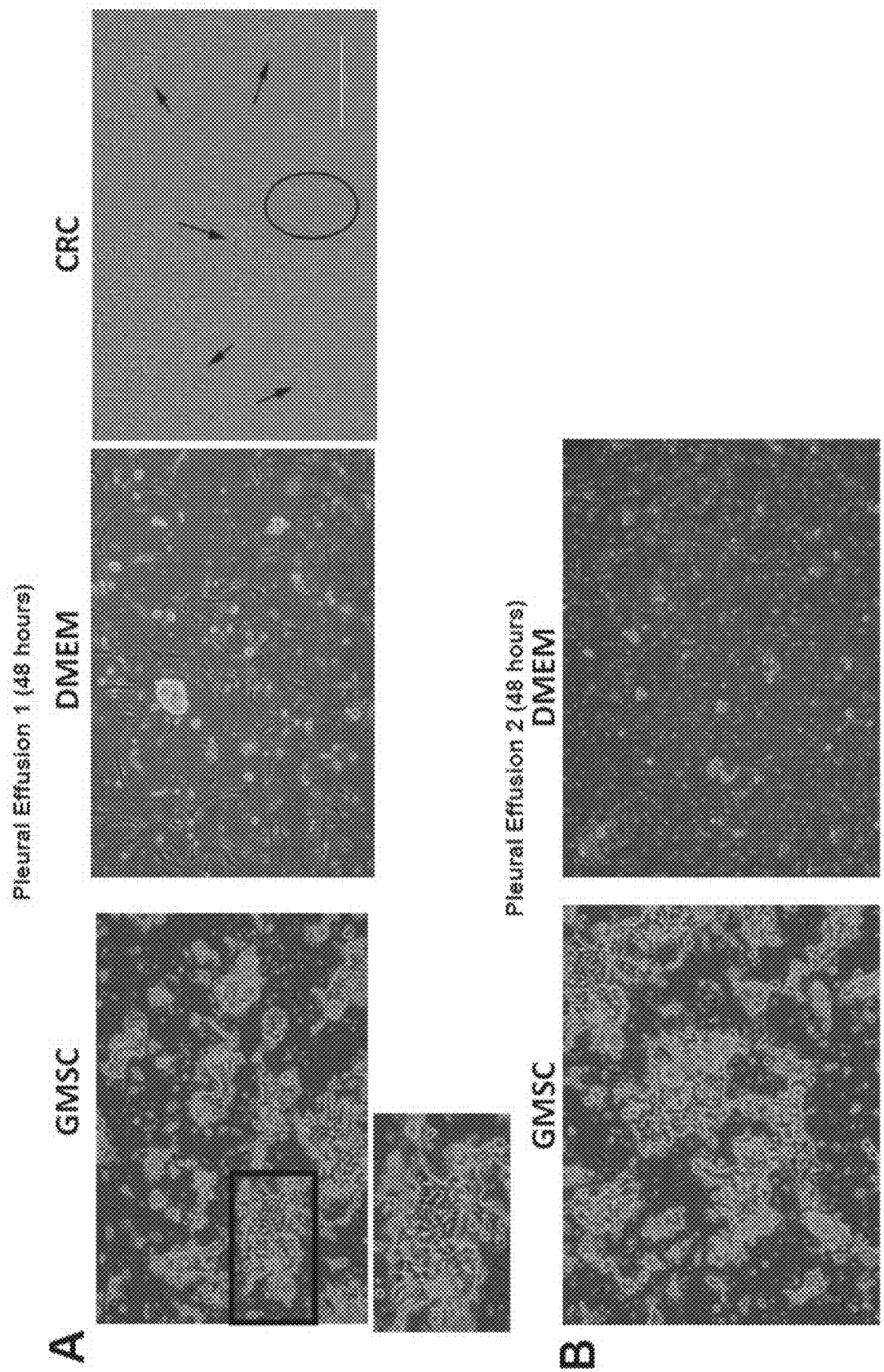
Figures 12A-B

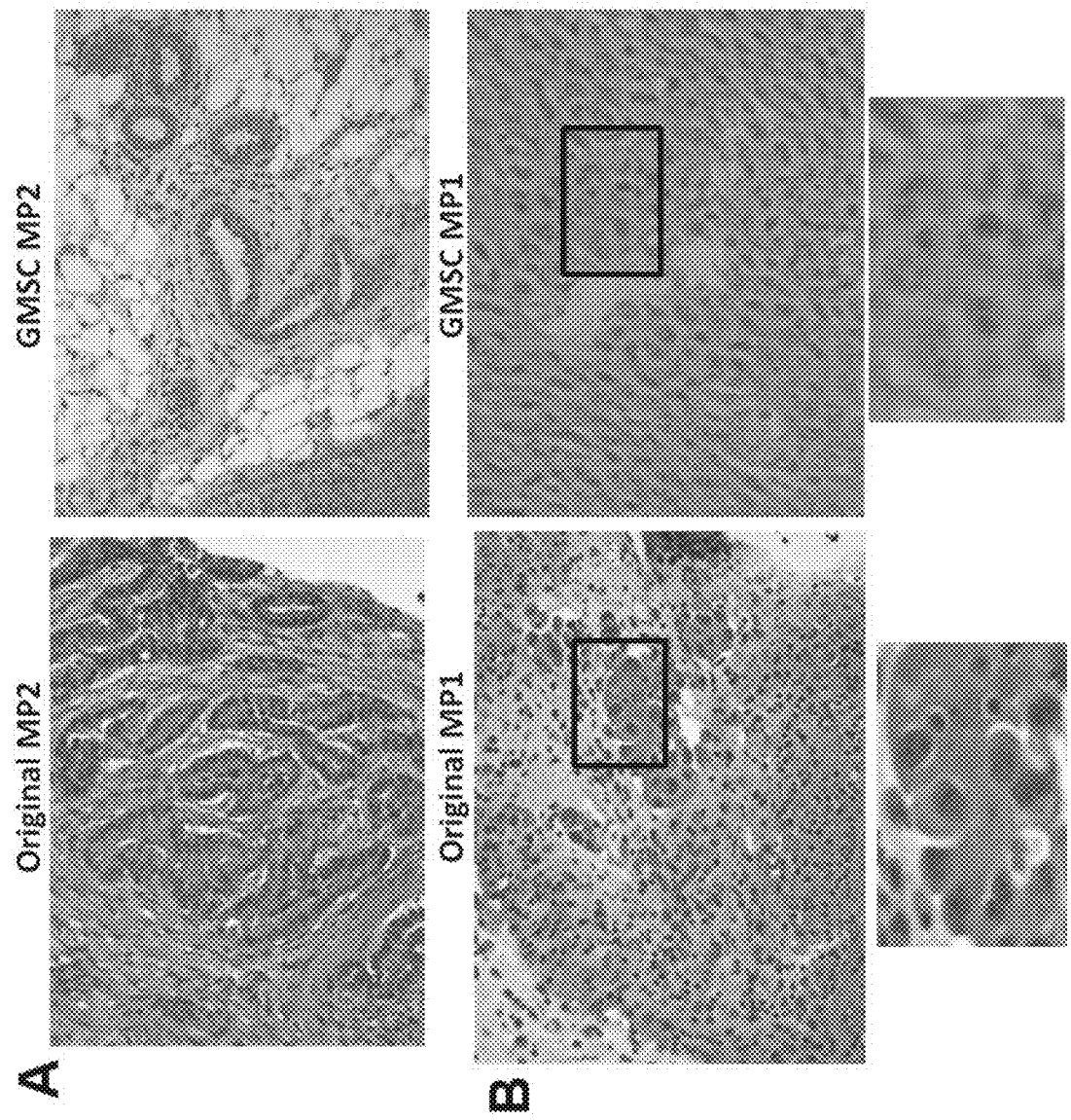
Figures 13A-B

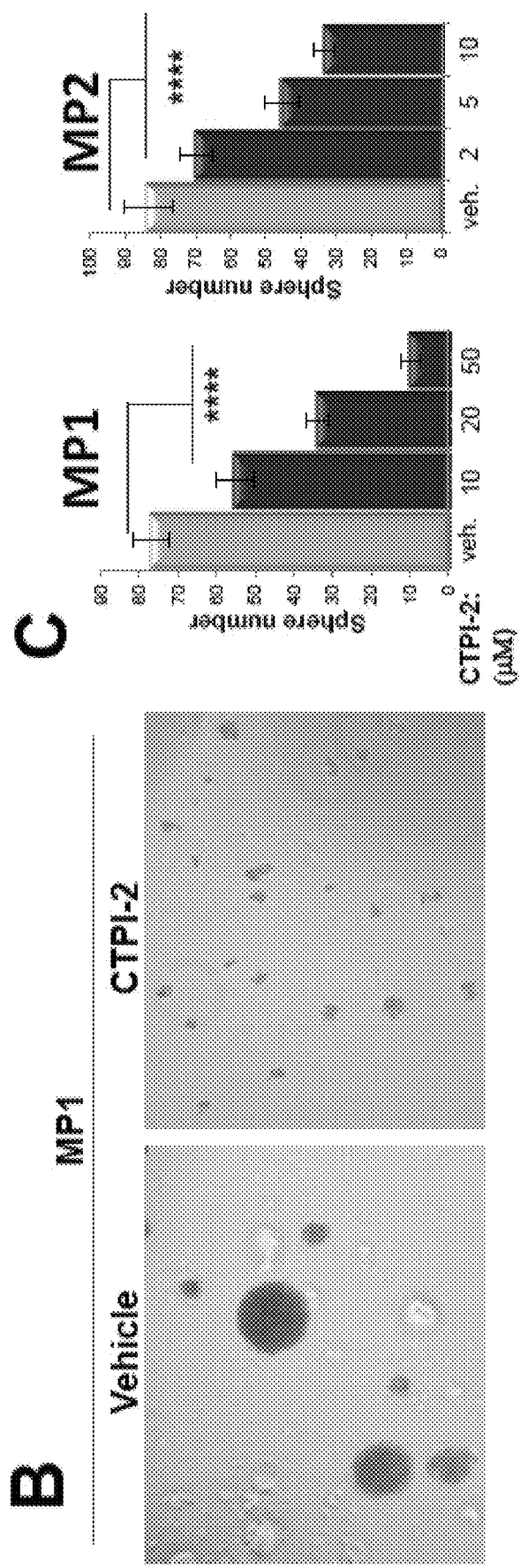
Figures 14B-C

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: synthetic construct

<400> SEQUENCE: 1
ccctccggga aactgtggcg                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic construct

<400> SEQUENCE: 2
gcagtgggga cacggaaggc                                              20

<210> SEQ ID NO 3
<211> LENGTH: 20
<212> TYPE: DNA
<213> ORGANISM: Artificial Sequence
<220> FEATURE:
<223> OTHER INFORMATION: synthetic construct

<400> SEQUENCE: 3
gaggacaaca tgaactgcca                                              20

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
taacatgggt gcgttcttca                                              20

<210> SEQ ID NO 5
<211> LENGTH: 19
<212> TYPE: DNA
<213> ORGANISM: Artificial Sequence
<220> FEATURE:
<223> OTHER INFORMATION: synthetic construct

<400> SEQUENCE: 5
ggtgagacct gcctgaatg                                               19

<210> SEQ ID NO 6
<211> LENGTH: 17
<212> TYPE: DNA
<213> ORGANISM: Artificial Sequence
<220> FEATURE:
<223> OTHER INFORMATION: synthetic construct

<400> SEQUENCE: 6
gttcttgcag ggggtgc                                                 17

<210> SEQ ID NO 7
<211> LENGTH: 30
<212> TYPE: DNA
<213> ORGANISM: Artificial Sequence

```
<220> FEATURE:
<223> OTHER INFORMATION: synthetic construct

<400> SEQUENCE: 7
caccatggac ccgggcgtgg ctgccagaaa                                        30

<210> SEQ ID NO 8
<211> LENGTH: 25
<212> TYPE: DNA
<213> ORGANISM: Artificial Sequence
<220> FEATURE:
<223> OTHER INFORMATION: synthetic construct

<400> SEQUENCE: 8
aagctgactt gctgggaact tgacc                                             25

<210> SEQ ID NO 9
<211> LENGTH: 20
<212> TYPE: DNA
<213> ORGANISM: Artificial Sequence
<220> FEATURE:
<223> OTHER INFORMATION: synthetic construct

<400> SEQUENCE: 9
agatcaaggc tgaagacccc                                                   20

<210> SEQ ID NO 10
<211> LENGTH: 20
<212> TYPE: DNA
<213> ORGANISM: Artificial Sequence
<220> FEATURE:
<223> OTHER INFORMATION: synthetic construct

<400> SEQUENCE: 10
gaggagctgc tgtatgtccc                                                   20

<210> SEQ ID NO 11
<211> LENGTH: 19
<212> TYPE: DNA
<213> ORGANISM: Artificial Sequence
<220> FEATURE:
<223> OTHER INFORMATION: synthetic construct

<400> SEQUENCE: 11
ccccatggag accatcaag                                                    19

<210> SEQ ID NO 12
<211> LENGTH: 19
<212> TYPE: DNA
<213> ORGANISM: Artificial Sequence
<220> FEATURE:
<223> OTHER INFORMATION: synthetic construct

<400> SEQUENCE: 12
cctggtacgt ccccttcag                                                    19
```

SMALL MOLECULE INHIBITORS OF SLC25A1

CROSS-REFERENCE TO PRIORITY APPLICATION

This application claims priority to U.S. Provisional Application No. 62/540,725, filed Aug. 3, 2017, which is incorporated by reference herein in its entirety.

STATEMENT REGARDING FEDERALLY FUNDED RESEARCH

This invention was made with government support under grant number R01CA193698 awarded by the National Institutes of Health. The government has certain rights in the invention.

BACKGROUND

SLC25A1 is a mitochondrial carrier that promotes the efflux of citrate from the mitochondria to the cytoplasm, in exchange for the mitochondrial entry of cytosolic malate or citrate itself. In the cytoplasm, citrate is the precursor for lipid biosynthesis and an inhibitor of glycolysis, while in the mitochondria, citrate enters the Krebs cycle and promotes mitochondrial respiration. SLC25A1 is a metabolic oncogene, but the exact mechanisms of action of this protein are still unclear. Furthermore, the mitochondrial oxidative metabolism has not been methodically considered as a target for drug development due to the Warburg hypothesis, whose central tenet is that tumor cells rely on aerobic glycolysis for production of energy, while mitochondria respiration is inactive.

SUMMARY

Provided herein are methods for the use of small molecules for treating or preventing cancer, diabetes, and obesity in a subject. The methods comprise administering to the subject an effective amount of a compound of the following structure:

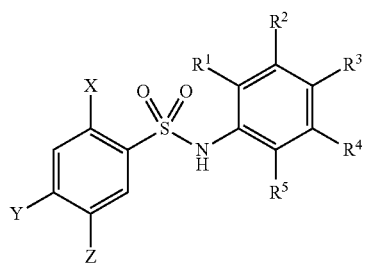

or a pharmaceutically acceptable salt thereof, wherein $R^1$, $R^2$, $R^3$, $R^4$, $R^5$, X, Y, and Z are each independently selected from the group consisting of hydrogen, halogen, nitro, hydroxy, amino, alkoxy, substituted or unsubstituted carbonyl, substituted or unsubstituted alkyl, substituted or unsubstituted alkenyl, and substituted or unsubstituted alkynyl. Optionally, when $R^1$, $R^2$, $R^3$, $R^5$, and Y are hydrogen, X is chloro, and Z—$CO_2H$, $R^4$ is not nitro. Optionally, X is hydrogen, Y is chloro, Z is nitro, and/or $R^5$ is —$CO_2H$. Optionally, the compound is

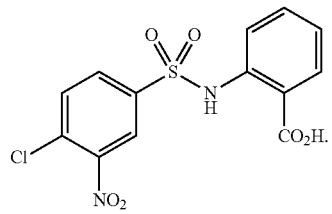 [SMILES: O=C(O)c1ccccc1NS(=O)(=O)c1ccc(Cl)c([N+](=O)[O-])c1]

The method can further comprise administering a second therapeutic agent to the subject. Optionally, the second therapeutic agent for treating cancer is a chemotherapeutic agent, such as an epidermal growth factor receptor (EGFR) inhibitor (e.g., gefitinib, erlotinib, lapatinib, cetuximab, panitumumab, vandetanib, necitumumab, or osimertinib) or cisplatin. The compound and the second therapeutic agent can be administered concomitantly or sequentially.

Optionally, the cancer can be lung cancer (e.g., non-small cell lung cancer), breast cancer, or colon cancer. The cancer can optionally be a cisplatin-resistant cancer or an EGFR inhibitor-resistant cancer.

Further described herein is a pharmaceutical composition comprising a compound of the following formula:

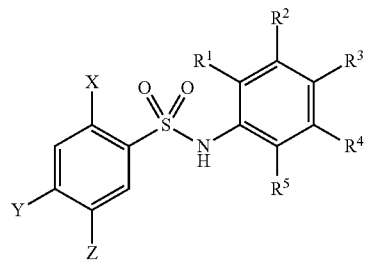

or a pharmaceutically acceptable salt thereof, wherein $R^1$, $R^2$, $R^3$, $R^4$, $R^5$, X, Y, and Z are each independently selected from the group consisting of hydrogen, halogen, nitro, hydroxy, amino, alkoxy, substituted or unsubstituted carbonyl, substituted or unsubstituted alkyl, substituted or unsubstituted alkenyl, and substituted or unsubstituted alkynyl. In the compound, when $R^1$, $R^2$, $R^3$, $R^5$, and Y are hydrogen, X is chloro, and Z—$CO_2H$, $R^4$ is not nitro. Optionally, X is hydrogen, Y is chloro, Z is nitro, and/or $R^5$ is —$CO_2H$. Optionally, the compound is

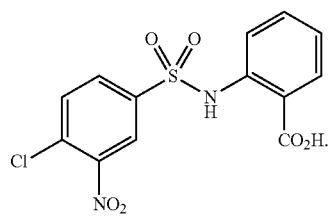 [SMILES: O=C(O)c1ccccc1NS(=O)(=O)c1ccc(Cl)c([N+](=O)[O-])c1]

The composition optionally further comprises a second therapeutic agent such as a chemotherapeutic agent. Optionally, the chemotherapeutic agent is an epidermal growth factor receptor (EGFR) inhibitor (e.g., gefitinib, erlotinib, lapatinib, cetuximab, panitumumab, vandetanib, necitumumab, or osimertinib) or cisplatin. The composition can further comprise a pharmaceutically acceptable carrier.

Also provided herein are methods of inhibiting SLC25A1 in a cell. The methods of inhibiting SLC25A1 in a cell comprise contacting a cell with an effective amount of a compound of the following structure:

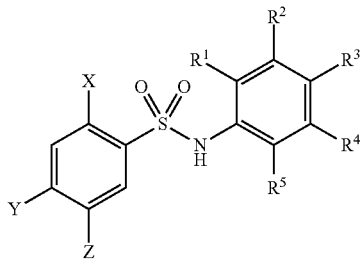

or a pharmaceutically acceptable salt thereof, wherein $R^1$, $R^2$, $R^3$, $R^4$, $R^5$, X, Y, and Z are each independently selected from the group consisting of hydrogen, halogen, nitro, hydroxy, amino, alkoxy, substituted or unsubstituted carbonyl, substituted or unsubstituted alkyl, substituted or unsubstituted alkenyl, and substituted or unsubstituted alkynyl. In the compound, when $R^1$, $R^2$, $R^3$, $R^5$, and Y are hydrogen, X is chloro, and Z—$CO_2H$, $R^4$ is not nitro. Optionally, X is hydrogen, Y is chloro, Z is nitro, and/or $R^5$ is —$CO_2H$. Optionally, the compound is

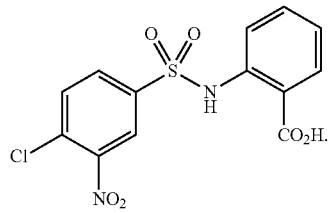 [SMILES: O=C(O)c1ccccc1NS(=O)(=O)c1ccc(Cl)c([N+](=O)[O-])c1]

The contacting can be performed in vivo or in vitro.

The details of one or more embodiments are set forth in the drawings and the description below. Other features, objects, and advantages will be apparent from the description and drawings, and from the claims.

DESCRIPTION OF DRAWINGS

FIGS. 1A-1K demonstrate that SLC25A1 expression correlates with metastatic disease and promotes stemness in lung adenocarcinoma. FIG. 1A shows a representative SLC25A1 immuno-histochemical staining of tissue microarrays of lung adenocarcinomas. FIG. 1B shows representative images of an immuno-reactive tumor, normal adjacent tissue (NAT) and metastatic lymph node. FIG. 1C provides a quantitative analysis of SLC25A1 staining by scoring based on percentage of reactive cells. FIG. 1D shows results of a quantitative real time PCR (normalized values) on the indicated gene products performed in either monolayer (red bars) or spheres (blue bars) of H1299 cells analyzed in triplicate samples. FIG. 1E shows results of a real time PCR performed in naive or SLC25A1 H1299 expressing cells as described in FIG. 1D. FIGS. 1F, 1G, and 1H show the results of a FACS analysis of CD166 and CD133 expression and of the CD44high/CD24low population in naive H1299 and tet-induced SLC25A1 cells. FIG. 1I shows quantification of the indicated markers from three independent experiments each with duplicate values. FIG. 1J shows cells derived from control or SLC25A1 expressing cells dissociated and plated as single cells in semi-solid media. After one week spheres were isolated, dissociated again and re-plated in the same conditions, producing second generation spheres. FIG. 1K shows the sphere-forming ability of H1299 cells infected with lentivirus control shRNA, or harboring either of two SLC25A1 shRNAs (825 and 350), dissociated and plated as single cells in semi-solid media. Bars represent the standard deviation, asterisks refer to * $P \leq 0.05$  $P \leq 0.01$ * $P \leq 0.001$ **** $P \leq 0.0001$ by unpaired T test relative to control cells.

FIGS. 2A-F depict the structures and activity of SLC25A1 inhibitors as described herein. FIG. 2A top panel shows a comparison of the structure of SLC25A1 inhibitors. FIG. 2A bottom panel shows the properties of citrate, BTA, CTPI-1, and CTPI-2: a: Calculated octanol-water partition coefficient; b: Topical polar surface area (TPSA); c: Experimental dissociation constant. d: Docking score calculated by the UCSF DOCK6.7 software. FIG. 2B shows the structure of the leading compound (CTPI-1) and of the newly identified SLC25A1 inhibitor, (CTPI-2). FIG. 2C is a binding model for citrate, CTPI-1, or CTPI-2 in complex with a homology model of human SLC25A1. The DOCK6.7 software provided a score for binding and a potential pose for the structure. Refinement of the structure using the AMBER MD module in the UCSF DOCK6.7 suite of software was performed to give the optimized models. The model shows the relevant amino acids previously known to be involved in citrate binding. The interaction of citrate with SLC25A1 appears to be mainly through hydrogen bond interactions with several basic residues in the SLC25A1 including Lys147, Lys245, Arg285, Lys50, and Arg282. The dissociation constant as assessed with SPR (Kd) and the docking score calculated by the UCSF DOCK6.7 software are shown. FIG. 2D shows H1299 cells transduced with control or with the SLC25A1-shRNA lentivirus. Cells were selected in puromycin for one week and the total number of live cells was counted after one week. FIG. 2E shows a comparison of the activity of CTPI-1 and CTPI-2 in sphere forming assays at the indicated concentrations. Asterisks indicate p values calculated from cells plated in five or six independent wells. Numbers in FIGS. 2D and 2E indicate fold changes relative to control. FIG. 2F is an analysis of the cell cycle of H1299 spheres or of spheres treated with CTPI-2 after three days of treatment.

FIGS. 3A-J show that SLC25A1 affects mitochondrial activity in cancer stem cells (CSCs) via a citrate import pathway. FIG. 3A shows oxygen consumption rates (OCR) assessed using the Seahorse Extracellular Flux Analyzer after injection of oligomycin (0), FCCP (F) and Antimycin/Rotenone (A+R), in H1299 cells expressing SLC25A1 grown as a monolayer or as spheres. OCR was normalized to cell number. To eliminate the influence of the media composition, monolayer and sphere cultures were first grown for several days and were then dissociated, plated on 96 wells coated with Geltrex, and pre-equilibrated in the same media containing serum and 5% glucose for 6-12 hours, prior to the assessment of the OCR. FIG. 3B is the dynamic profile of OCR of H1299 cells grown as indicated. FIG. 3C shows H1299 cells derived from spheres and treated with CTPI-2 (25 mM and 50 mM) for three hours. FIG. 3D shows an assessment of citrate levels in mitochondrial or cytoplasmic fractions and in the presence or absence of CTPI-2 (4 hours treatment). FIGS. 3E and 3F show OCR assessed in untreated or CTPI-2 treated cells with or without malate, succinate, or citrate over the course of a three hours period. In FIG. 3E, the curves overlap. FIG. 3G shows an assessment of self-renewal in monolayer cultures or in sphere forming assays after one week of treatment with the indicated metabolites in mock treated or CTPI-2 treated cells. FIG. 3H shows images of H1299 2D (top panels) or 3D (bottom panels) cultures treated with the indicated inhibitors. FIG. 3I shows a quantification of cell viability or sphere number in monolayer or single-cell derived sphere cultures treated with Rotenone (Rot.; 10 nM), Oligomycin (Olig.; 1 mM), or metformin (met. 3 mM). FIG. 3J shows results for H1299 cells plated as a monolayer or in methylcellulose as single cells and treated with the indicated concentrations of CTPI-2 or CPI-163. Bars represent standard deviations and asterisks refer to * $P \leq 0.05$  $P \leq 0.01$ * $P \leq 0.001$ **** $P \leq 0.0001$ by unpaired T test relative to control cells.

FIGS. 4A-G depict the effects of CTPI-2 on aerobic glycolysis. FIGS. 4A-B show an ECAR profile (FIG. 4A) and levels of glycolysis (FIG. 4B) in H1299 cells grown as a monolayer or spheres (abbreviated "m" and "s," respectively). Cells were first grown in media lacking glucose, glutamine, and pyruvate for 3 hours, following the consecutive injection of 10 mM glucose, oligomycin, and 2-deoxyglucose, as shown. FIG. 4C shows levels of glucose-driven OCR extrapolated from the same experiment. FIG. 4D shows ECAR rates for H1299 spheres or monolayer cultures first starved of glucose, followed by injection of 10 mM glucose with CTPI-2 (lanes 3,4,7 and 8) or without CTPI-2 (lanes 1, 2, 5, and 6). ECAR rates were calculated by plotting the values before (grey bars) and after (black bars) glucose injection. FIG. 4E shows lactic acid levels assessed in the indicated growth conditions and in the presence or absence of CTPI-2. FIG. 4F is a model for the import and export activity of SLC25A1 in monolayer versus spheroid CSC cultures and the effects of CTPI-2 on glycolysis. FIG. 4G shows phosphofructokinase (PFK) activity assessed in the same conditions described in FIG. 4D. Cells were first plated as a monolayer or as spheres for 36 hours and treated with citrate (10 mM) overnight, the day before the measurements (lanes 3 and 6). The following day, cells were treated as in FIG. 4D, 5 mM citrate was re-added and cells were simultaneously either mock treated (lanes 1,4) or treated with CTPI-2 (lanes 2,3,5,6) for 3 hours.

FIG. 5A shows morphological features of primary lung cancer cells, MP1 and MP2, grown in GMSC for one week or in 2D cultures in regular attachment plates, with serum and DMEM. FIG. 5B shows the results of analysis with FACS of the CD166, CD133, and CD87 markers in the MP1 and MP2 cells in the indicated growth conditions. FIGS. 5C-D show normalized OCR and ATP levels in MP1 or MP2 cells grown as monolayer or in GMSC. Once spheres were formed cells were dissociated, plated in 96 wells coated with Geltrex, and incubated in the same media for 6-12 before assessment of the OCR. Treatment with CTPI-2 was for 3 hours. FIG. 5E shows spheres derived from MP1 cells grown for several passages in GMSC. The spheres were collected by sedimentation and embedded in 100% geltrex. Spheres were imaged immediately after plating, and fields were identified by numbers on the plate and re-imaged for 7-10 days. The rectangles indicate the enhanced areas of each field shown on the right side. Invadopodia formation was calculated using the 'imageJ' program by first measuring the areas of the spheres (inner area) and the area of the spheres along with its invadopodia (outer area). FIG. 5F shows the percent difference between the outer area and the inner area. Spheres of similar areas were selected for comparison, whereas the outliers were eliminated so as to exclude the influence of different cell number.

FIGS. 6A-H show that SLC25A1-dependent mitochondrial-respiration drives therapy resistance. FIGS. 6A-B show the results for MP1 and MP2 cells treated with cisplatin (0.5-1 mM) or AZD9291 (1 mM), as indicated in each panel, passaged in the presence of the drugs, then subjected to OCR analysis with the Seahorse analyzer. FIG. 6C shows SLC25A1 protein levels in MP1 and MP2 cells cultured in the presence or absence of cisplatin. FIG. 6D shows FACS analysis of CD166 and CD133 markers in the cisplatin or AZD9291 resistant MP1 or MP2 cells. FIGS. 6E-G show results for MP1 (FIG. 6E), MP2 (FIG. 6F) and MP3 (FIG. 6G) cells untreated or treated with the indicated drugs. The concentration of drugs employed is indicated at the bottom of each panel. Viability was assessed with Crystal Violet after 5 days of treatment. Relative (R) index calculations were used to assess the type of drug interactions and are indicated in each panel. The R index is calculated as the expected cell survival (Sexp; the product of relative survival in cisplatin and relative survival in CTPI-2) divided by the observed relative survival in the presence of both drugs (Sobs). Sexp/Sobs=1.0 denotes an additive interaction, while >1.0 denotes a synergistic interaction, R index values approaching 2.0 are indicative of strong synergy. FIG. 6H is a proposed model for the effects of SLC25A1 and CTPI-2 in resistant cell populations.

FIGS. 7A-G show anti-tumor activity of CTPI-2. FIG. 7A shows results for MP1 cells grown as monolayer cultures or in GMSC conditions and injected in Balb/c athymic nude mice at 5 million cells/injection site. The time at which tumors started to appear was recorded and plotted in the graph (n=7 per group). FIG. 7B shows tumor volumes of monolayer (bars on the left in each pair) or GMSC-expanded spheres (bars on the right in each pair) from FIG. 7A, which were treated with vehicle (DMSO) or CTPI-2 (N=6 per group). FIG. 7C shows representative images of tumor growth in mock-treated or CTPI-2-treated mice. Arrows indicate the injected sites. FIG. 7D shows the results for MP1 cells injected in immuno-compromised mice, which were randomized to receive vehicle or cisplatin (3 mg/Kg every three days) alone or in combination with CTPI-2. Treatments were started when tumors became solid and palpable (between 30-50 mm$^3$) (n=8 tumors for vehicle, n=17 for cisplatin, n=17 for combination group). The right panel shows the comparison of cisplatin versus combination treatment only. Each point represents the mean±SEM of tumor volumes. FIG. 7E shows the tumor doubling times calculated by using the formula employed by radiologist (an online calculator was used at: http://www.chestx-ray.com/index.php/calculators/doubling-time), by analyzing the difference between tumor volumes the day before starting treatments and at the end of the experiment. FIG. 7F shows immuno-blots with the indicated antibodies of tumors derived from MP1 cells injected as a monolayer (lane 1), or as GMSC (lanes 2-4) treated with vehicle (2), cisplatin (lane 3), or a combination of cisplatin and CTPI-1 (lane 4). FIG. 7G shows data for MP2 cells injected in immuno-compromised mice. When tumors reached a size of 30-50 mm$^3$, mice were randomly assigned to either the control group (vehicle), AZD9291 treatment (10 mg/Kg every other day), or a combination treatment of AZD9291 with CTPI-2 (n=6 tumors per group).

FIG. 8A shows tissue microarrays of 30 matched tumor and normal tissues from squamous carcinoma stained for SLC25A1. FIG. 8B shows scoring criteria examples for squamous cell carcinomas and adenocarcinomas. FIG. 8C shows the results of staining score relative to normal and adjacent normal tissues in squamous cell carcinoma, showing positivity in tumors.

FIGS. 9A-F show that SLC25A1 inhibition affects stemness and sphere forming ability. FIG. 9A shows the cell cycle profile of H1299 cells grown as monolayers or spheres. FIG. 9B are immuno-blots for SLC25A1, mitofilin or actin of H1299 cells harboring tetracycline-inducible SLC25A1 cDNA, grown as a monolayer (lanes 1-3), or as spheres (lanes 4-6) in the presence (+) or absence of tetracycline. Two exposures of the SLC251A blot are shown. Note the enrichment of SLC25A1 in spheres versus monolayer cultures (lane 1 versus 4). FIG. 9C shows growth curves of H1299 or SLC25A1 expressing cells cultured as spheres, dissociated and counted at each of the indicated time points. FIG. 9D shows growth curves of H1299 cells infected with lentivirus control shRNA or harboring either of two SLC25A1 shRNAs (825 and 350). FIG. 9E shows CD166 and CD44 expression in cells infected with PLKO control lentivirus or with lentivirus harboring the specific SLC25A1 shRNA. FIG. 9F shows sphere forming ability assessed one week after treatment with the SLC25A1 inhibitors BTA (2 mM) and CTPI (1 mM).

FIGS. 10A and B show identification of a SLC25A1 inhibitor. FIG. 10A shows direct binding of CTPI-1, and FIG. 10B shows direct binding of CTPI-2 as measured by SPR. Recombinant purified SLC25A1 protein was immobilized on Biacore NTA chip and different concentrations of compounds were injected over the protein coated surface in triplicates (insets show raw data). Binding values from 5 seconds prior to the end of injection were plotted against compound concentration to calculate steady state binding affinity (KD) based on a 1:1 binding model in BiaEvaluation software.

FIG. 11A shows oxygen consumption rates (OCR), maximal and spare respiratory capacity (SPR) assessed using the Seahorse Extracellular Flux Analyzer after injection of oligomycin, FCCP and Antimycin/Rotenone in H1299 cells grown as adherent or spheres. FIG. 11B shows OCR levels and activity of the CTPI-2 in H1299 cells infected with control PLKO lentivirus (labeled "PLKO+CTPI-2" and indicated as dark squares), or with SLC25A1-shRNAs in the absence (labeled "shRNA SLC25A1" and indicated as light squares) or presence (labeled "shRNA SLC25A1+CTPI-2" and indicated as triangles) of CTPI-2. PLKO alone is indicated in the graph as diamonds. The curves for shRNA-SLC25A1 untreated and treated with CTPI-2 overlap and are not discernable. FIG. 11C shows a side-by-side comparison of the effects of metformin and CTPI-2 on the glycolytic rates of sphere-grown-CSCs.

FIGS. 12A and 12B show the characteristics of the GMSC system. FIGS. 12A and 12B are side-by-side comparisons of primary tumor cells derived from two pleural effusions. Abundant cell pellets were obtained after centrifugation of approximately 400-800 ml of pleural fluid, which was equally divided and plated in GMSC (on matrix-coated plates and in the presence of stem cell media), or in regular attachment plates cultured with DMEM and 10% FBS. FIG. 12A also shows results with irradiated JC1 fibroblasts using Conditionally Reprogramming Conditions (CRC). The rectangle shows an area enlarged at the bottom of the panel. In the CRC panel, circles and arrows indicate colonies of cells embedded on top of irradiated J2 cells. The different viabilities of the cells in DMEM adherent cultures versus GMSC cultures are displayed.

FIGS. 13A-B show two primary tumor lines, MP1 and MP2, that were grown as GMSC spheroid cultures and injected in nude mice. Tumors were isolated and were stained with hematoxylin and eosin (H&E). The panels show a comparison of the histological characteristics of the original tumor (left panels) with the GMSC expanded tumor. In FIG. 13B, the rectangles outline atypical cells of the original tumor with enlarged nucleoli that were detected in the xenografted GMSC-expanded MP1 line.

FIGS. 14A-F show that patient-derived CSCs depend upon SLC25A1 for survival. FIG. 14A shows results for MP1 cells expanded as GMSC-spheres for several passages, dissociated and sorted for CD166 or alternatively left unsorted. OCR measurements of basal, maximal, and SRC were performed as described previously. FIGS. 14B-C show that CTPI-2 disrupts self-renewal and sphere forming capacity of MP1 and MP2 cells plated in semi-solid media in methylcellulose. FIG. 14D shows the effects of CTPI-2 on patient-derived (MP4) differentiated monolayer cultures or on self-renewal, assessed on GMSC-derived single cells plated in semi-solid media. FIG. 14E shows H1299 cells or SLC25A1-expressing cells were grown as spheres for several passages and then embedded in an ECM matrix (geltrex). The spheres were either mock treated or treated with CTPI-2. Representative images are shown. FIG. 14F shows invadopodia formation calculated using 'imageJ' program by first measuring the areas of the spheres (inner area) and the area of the spheres along with its invadopodia (outer area). The percent difference between the outer area and the inner area was graphed and spheres of similar areas were selected for comparison, whereas the outliers were eliminated so as to exclude the influence of different cell number.

FIGS. 15 A-D show the effects of CTPI-2 on resistant cancer cells. FIG. 15A shows mitochondrial respiratory profile from monolayer cultures of MP2 cells exposed to cisplatin treatment alone or in combination with CTPI-2. Assessment of mitochondrial respiratory profile was performed as described before. On the left panel, the curves of untreated control and CTPI-2 treated overlap and are not distinguishable. FIG. 15B shows flow cytometry analysis with annexin V and PI staining of MP1 cells treated with cisplatin or CTPI-2, alone or in combination. FIG. 15C shows results for H1299 cells mock-infected or infected with the SLC25A1 lentivirus established for one week after selection in puromycin. Cells were treated with cisplatin (5 mM) and viability was assessed with trypan blue exclusion after five days. FIG. 15D shows results for a single clone of MP1 cisplatin-resistant cells (squares) or parental cells (diamonds) treated with cisplatin alone (left panel) or with combination cisplatin and CTPI-2 at the indicated concentrations. Relative (R) index calculations are indicated.

DETAILED DESCRIPTION

Figure 2C:
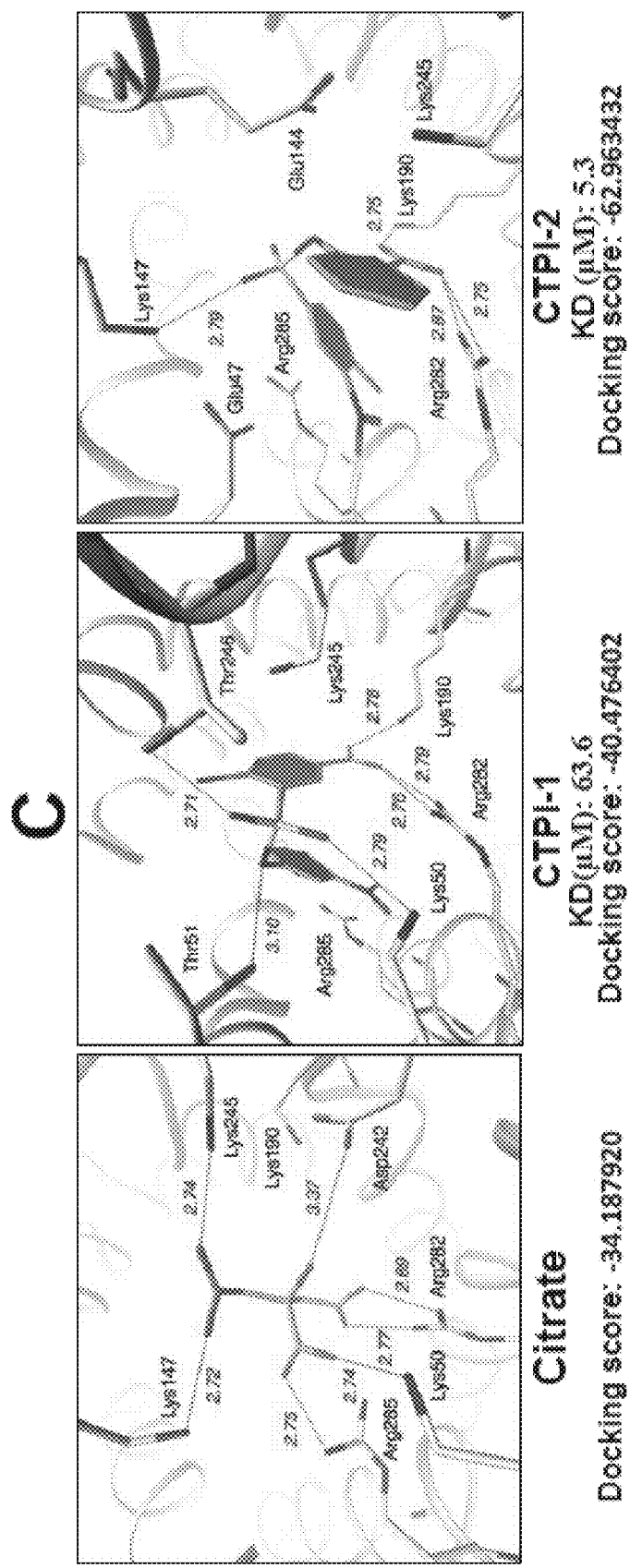

Described herein are inhibitors of SLC25A1 and methods of using the SLC25A1 inhibitors. SLC25A1 is required for the proliferation of tumor cells, particularly for the expansion of the cancer stem cell population in lung cancer. Genetic or pharmacological inhibition of SLC25A1 hampers tumor growth and blocks important metabolic branches required for the growth and expansion of cancer stem cells. The SLC25A1 inhibitors described herein can be used to treat or prevent cancer (e.g., non-small cell lung cancer), diabetes, and/or obesity. Also described herein are pharmaceutical compositions including an SLC25A1 inhibitor and, optionally, a second therapeutic agent (e.g., a chemotherapeutic agent).

I. Compounds

A class of SLC25A1 inhibitors useful in the methods described herein includes compounds represented by Formula I:

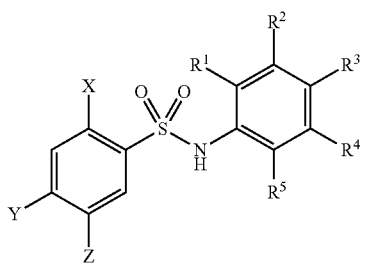

or a pharmaceutically acceptable salt or prodrug thereof.

In Formula I, $R^1$, $R^2$, $R^3$, $R^4$, $R^5$, X, Y, and Z are each independently selected from the group consisting of hydrogen, halogen (e.g., chloro, fluoro, bromo, or iodo), nitro, hydroxy, amino, alkoxy, substituted or unsubstituted carbonyl, substituted or unsubstituted alkyl, substituted or unsubstituted alkenyl, and substituted or unsubstituted alkynyl. Optionally, X is hydrogen. Optionally, Y is a halogen, such as chloro. Optionally, Z is nitro. Optionally, $R^5$ is —$CO_2H$.

In some examples of Formula I, when $R^2$, $R^3$, $R^5$, and Y are hydrogen, X is chloro, and Z—$CO_2H$, $R^4$ is not nitro.

An example of Formula I includes the following compound:

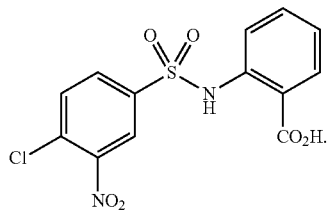

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

The term alkoxy as used herein is an alkyl group bound through a single, terminal ether linkage. The term hydroxy as used herein is represented by the formula —OH.

The terms amine or amino as used herein are represented by the formula —$NZ^1Z^2$, where $Z^1$ and $Z^2$ can each be substitution group as described herein, such as hydrogen, an alkyl, halogenated alkyl, alkenyl, or alkynyl group described above.

The alkoxy, amino, alkyl, alkenyl, alkynyl, or carbonyl molecules used herein can be substituted or unsubstituted. As used herein, the term substituted includes the addition of an alkoxy, amino, alkyl, alkenyl, alkynyl, or carbonyl group to a position attached to the main chain of the alkoxy, amino, alkyl, alkenyl, alkynyl, or carbonyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, amino, alkyl, alkenyl, alkynyl, or carbonyl has a full complement of hydrogens, i.e., commensurate with its saturation level, with no substitutions, e.g., linear decane (—$(CH_2)_9$—$CH_3$).

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. Eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, New Jersey), polyethylene glycol (PEG), and PLURONICS™ (BASF; Florham Park, NJ).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.0001 to about 200 mg/kg of body weight of active compound per day, which may be administered in a single dose or in the form of individual divided doses, such as from 1 to 4 times per day. Alternatively, the dosage amount can be from about 0.01 to about 150 mg/kg of body weight of active compound per day, about 0.1 to 100 mg/kg of body weight of active compound per day, about 0.5 to about 75 mg/kg of body weight of active compound per day, about 0.5 to about 50 mg/kg of body weight of active compound per day, about 0.01 to about 50 mg/kg of body weight of active compound per day, about 0.05 to about 25 mg/kg of body weight of active compound per day, about 0.1 to about 25 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, about 5 mg/kg of body weight of active compound per day, about 2.5 mg/kg of body weight of active compound per day, about 1.0 mg/kg of body weight of active compound per day, or about 0.5 mg/kg of body weight of active compound per day, or any range derivable therein.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

III. Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety. The synthesis and subsequent testing of various compounds as described by Formula I to determine efficacy is contemplated.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H-NMR or $^{13}$C-NMR) infrared spectroscopy, spectrophotometry (e.g., UV-visible), or mass spectrometry, or by chromatography such as high performance liquid chromatography (HPLC) or thin layer chromatography.

Optionally, the compounds described herein can be obtained from commercial sources. The compounds can be obtained from, for example, Sigma-Aldrich (St. Louis, Missouri).

IV. Methods of Use

Provided herein are methods to treat, prevent, or ameliorate cancer, diabetes, and obesity in a subject. The methods include administering to a subject an effective amount of one or more of the compounds or compositions described herein, or a pharmaceutically acceptable salt or prodrug thereof. The method can include selecting a subject with cancer, diabetes, or obesity, using methods within the art. The expression effective amount, when used to describe an amount of compound in a method, refers to the amount of a compound that achieves the desired pharmacological effect or other effect, for example, an amount that results in tumor growth rate reduction. The compounds and compositions described herein or pharmaceutically acceptable salts thereof are useful for treating cancer, diabetes, and obesity in humans, including, without limitation, pediatric and geriatric populations, and in animals, e.g., veterinary applications.

Optionally, the cancer is breast cancer (e.g., endocrine resistant breast cancer), lung cancer (non-small cell lung cancer), or colon cancer. Optionally, the breast cancer is endocrine resistant breast cancer. Optionally, the cancer is bladder cancer, brain cancer, colorectal cancer, cervical cancer, gastrointestinal cancer, genitourinary cancer, head and neck cancer, lung cancer, ovarian cancer, pancreatic cancer, prostate cancer, renal cancer, skin cancer, or testicular cancer. Optionally, the cancer is a cisplatin-resistant cancer or an epidermal growth factor receptor (EGFR) inhibitor-resistant cancer. Exemplary EGFR inhibitor-resistant cancers include gefitinib-resistant cancer, erlotinib-resistant cancer, lapatinib-resistant cancer, cetuximab-resistant cancer, panitumumab-resistant cancer, vandetanib-resistant cancer, necitumumab-resistant cancer, and osimertinib-resistant cancer.

The methods of treating or preventing cancer, diabetes, and obesity in a subject can further comprise administering to the subject a therapeutic agent or radiation therapy or a combination thereof. Thus, the provided compositions and methods can include one or more additional agents. The additional agent is optionally an agent to which the subject is unresponsive to if used alone. The one or more additional agents and the compounds described herein or pharmaceutically acceptable salts or prodrugs thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, chemotherapeutic agents, anti-depressants, anxiolytics, antibodies, antivirals, steroidal and non-steroidal anti-inflammatories, conventional immunotherapeutic agents, cytokines, chemokines, and/or growth factors. Therapeutic agents also include insulin and agents (e.g., glyburide, exenatide, pramlinitide, and metformin) used to control blood sugar in subjects with diabetes and anti-obesity medications (e.g., orlistat, sibutramine, and rimonabant).

The therapeutic agent can, for example, be a chemotherapeutic agent. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, EGFR inhibitors (e.g., gefitinib, erlotinib, lapatinib, cetuximab, panitumumab, vandetanib, necitumumab, and osimertinib), bexarotene, gemcitabine, paclitaxel, docetaxel, topotecan, irinotecan, temozolomide, carmustine, vinorelbine, capecitabine, leucovorin, oxaliplatin, bevacizumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g., anthracyclines such as doxorubicin, liposomal doxorubicin, and diethylstilbestrol doxorubicin, bleomycin, daunorubicin, and dactinomycin); antiestrogens (e.g., tamoxifen or faslodex); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); steroids (e.g., bethamethasone sodium phosphate); and aromatase inhibitors (e.g., letrozole).

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of cancer, diabetes, or obesity), during early onset (e.g., upon initial signs and symptoms of cancer, diabetes, or obesity), or after the development of cancer, diabetes, or obesity. Prophylactic administration can occur for several days to years prior to the manifestation of symptoms of cancer, diabetes, or obesity. Therapeutic treatment involves administering to a subject a therapeutically effective amount of the compounds and compositions or pharmaceutically acceptable salts thereof as described herein after cancer, diabetes, or obesity is diagnosed.

The methods and compounds described herein are also useful in inhibiting SLC25A1 in a cell. The methods include contacting a cell with an effective amount of one or more compounds as described herein. Optionally, the contacting is performed in vivo. Optionally, the contacting is performed in vitro.

The methods herein for prophylactic and therapeutic treatment optionally comprise selecting a subject with or at risk of developing cancer, diabetes, or obesity. A skilled artisan can make such a determination using, for example, a variety of prognostic and diagnostic methods, including, for example, a personal or family history of the disease or condition, clinical tests (e.g., imaging, biopsy, genetic tests and the like for cancer; measurements of body weight or body fat for obesity and diabetes; blood glucose levels for diabetes), and the like.

V. Kits

Also provided herein are kits for treating or preventing cancer, diabetes, or obesity in a subject. A kit can include any of the compounds or compositions described herein. For example, a kit can include a compound of Formula I. A kit can further include one or more additional agents, such as EGFR inhibitors (e.g., gefitinib, erlotinib, lapatinib, cetuximab, panitumumab, vandetanib, necitumumab, and osimertinib) or cisplatin. A kit can include an oral formulation of any of the compounds or compositions described herein. A kit can additionally include directions for use of the kit (e.g., instructions for treating a subject), a container, a means for administering or measuring the compounds or compositions, and/or a carrier.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1

Materials and Methods

Cells, reagents, antibodies, primers. The H1299 cell lines and other cell lines employed in this study were obtained from ATCC or from the tissue culture core facility at LCCC. Cells were grown in Dulbecco's Modified Eagle's Medium (DMEM, 25 mM glucose, with glutamine and pyruvate from Invitrogen; Carlsbad, CA) and supplemented with 10% fetal calf serum (FCS). The reagents used in this study were: 1,2,3, Benzenetricarboxylic acid (BTA), which is commercially available from Sigma (St. Louis, MO); CTPI-1 which is commercially available from Sigma; and CTPI-2, which is commercially available Enamine Ltd (Kiev, Ukraine) and from Santa Cruz Biotech (Dallas, TX). The SLC25A1 specific shRNA vectors were purchased from Sigma. The vector expressing human SLC25A1 untagged or Flag-Myc epitope tagged were from Origene; Rockville, MD (#SC120727 and RC200657, respectively). The anti-SLC25A1 antibody used in immuno-blot was from Santa Cruz Biotech, #sc-86392 employed at 1:1000 dilution. Citrate, lactate, and PFK measurements were performed by using commercially available kits (Biovision (Milpitas, CA)).

Growth of monolayers and sphere cultures. Tumor cell lines were grown as monolayers in complete Dulbecco's Modified Eagle's Media (DMEM, Gibco; supplemented with 10% fetal bovine serum and 1% of 5,000 units/mL of penicillin-streptomycin (pen-strep), Gibco). To generate spheroids, cells were grown in Falcon bacteriological petri dishes coated with 2% poly(2-hydroxyethyl methacrylate) dissolved in 100% ethanol. The growth media was DMEM/F12 (Gibco) supplemented with 20 ng/mL of epidermal growth factor (EGF), 5 ng/mL of fibroblast growth factor, 0.375% 100× N2 supplements (Gibco), and 1% pen-strep. Monolayer cells were dissociated using 0.25% trypsin-edta (Gibco), whereas spheroid cultures were dissociated using StemPro Accutase (Gibco). Patient derived cell lines were grown as described below in the primary lung cultures section.

Self-renewal assays. Tumor cells cultured as spheroids were dissociated and diluted in 2× sphere media containing 1% methyl cellulose, which was previously dissolved in cold DMEM/F12 media. Either 200, 500, or 1000 cells were then plated in each 96 well and were incubated in the presence or absence of drugs, as indicated. The spheres were allowed to form for a period of a week to ten days, at which point they were counted. Six biological replicates were used for quantification of the results.

Invadopodia measurements. After embedding the spheres in a 3D matrix, their extent of invasion was monitored over 24 hours. Using an inverted microscope set at a magnification of 20×, images of the spheres were obtained at 0 hours, 24 hours, and 48 hours after plating. Analysis for invasion was done using 'imageJ' by NIH. The area of invasion was measured by sketching an outline around the spheres using the freehand draw tool. The 'measure' tool in 'Analyze' on the top menu calculated the area for the selected spheroid. The areas of just the spheres (inner area) and the area of the spheres along with its invadopodia (outer area) were measured. The percent difference between the outer area and the inner area was graphed to understand the extent of invasion in each cell type at different time points. The obtained areas for all the spheres were graphed. Spheres of similar areas were selected, whereas the outliers were eliminated so as to compare the spheres of similar volumes.

Primary lung cancer cultures and GMSC. Surgical samples were minced and digested with dispase (50 U/ml) in DMEM media containing 5% serum for 1 hour. Pleural effusions were centrifuged, washed once in PBS, and then plated. All primary cultures were initially grown on 6-well plates pre-coated with 2% Geltrex (Life Technologies; Carlsbad, CA) and 1% Maxgel (Sigma Aldrich). Maxgel is a humanized matrix, native and non-denatured. The inclusion of Maxgel in the system enhanced the initial attachment of primary tumor cells, partially because Maxgel provides a more natural ECM conformational substrate. The day after plating, the media containing unattached cells was typically transferred to a fresh plate, in most of cases generating new attached cultures. The media (Stem Cell Media) is the DMEM/F12 (Thermo-Fisher #11320-033 basic media) supplemented with the following components: Insulin-Transferrin-Sodium selenite (ITS; 1:1000; Sigma #11884); glutamine (Thermo-Fisher) to 4 mM final concentration; sodium pyruvate (Thermo-Fisher) to 2 mM final concentration; rock inhibitor (Y-27632) 10 micrograms/mL; 2-5% Knock Out Serum Replacement (KNOSR, Thermo-Fisher #10828-028); 0.5% ALBUMAX-(Lipid enriched BSA; Thermo-Fisher #11020-021); N2 Supplement (Thermo-Fisher) 1:250; EGF (5 ng/ml; Peprotech); hFGF (20 ng/ml; Bechman); and IGF-1 (Peprotech; 10-20 ng/ml).

The matrix was replaced every two days. At each passage, duplicate cultures were generated by plating an aliquot of the GMSC-grown cells in regular attachment plates grown in DMEM and serum. This switch could often be achieved at around passage 7-10. The stromal component (mostly fibroblasts) was eliminated in early cultures with differential trypsinization (fibroblasts are more resistant to trypsin) and by growing the cells in low attachment plates and in Stem Cell Media for two or three passages. Fibroblasts were unable to form spheres while epithelial cells were enriched in these conditions. Cells could be frozen in stem cell media (or in DMEM media) and re-started on matrix-coated plates.

Cellular proliferation and cytotoxicity assays. The proliferative capacity of cells was assessed by plating cells in triplicate at a concentration of 2,000 to 10,000 cells/well in 96 well plates in triplicate, with or without drug treatment for 48 hours. The cells were then washed with 1×PBS and fixed with cold 100% methanol at –20° C. for 20 minutes. Methanol was washed off and the cells were stained with 0.5% crystal violet dissolved in 25% methanol and water at 4° C. for 20 minutes. The staining was washed off using deionized (DI) water and the plate was dried overnight. On the second day, 100 mM sodium citrate in 50% ethanol and 50% water was added to the wells and absorbance at 550 nm was measured and corrected with readings at 405 nm. In other experiments, cell viability was assessed by trypan blue exclusion and visual count of the live cells was performed.

Flow cytometry. Tumor cells were trypsinized and washed in 1×PBS. The cells were then stained with the antibodies of choice: CD166-PE (Biolegend), CD133-647 (Biolegend), or CD44 (Biolegend), in 1% BAS-PBS. The cell cycles of monolayers or spheres of the cells were analyzed by fixing the cells in cold 75% ethanol. The annexin V (Biolegend) and propidium iodide (Biolegend) experiments were carried out.

Mitochondria isolation and cellular sub-fractionation. Mitochondria and cytoplasmic fractions were prepared as follows. Cells were collected in PBS for 5', then the pellet was e-suspended in 5 packed cell volumes of mitochondria buffer (250 mM sucrose; 20 mM HEPES (7.4); 10 mM KCl, 1.5 mM $MgCl_2$; 1 mM EDTA; 1 mM EGTA 0.5 M, supplemented with freshly added PMSF and 1 mM DDT). Cell lysates were passed through a 25 G needle 10 times, then 5 times through a 27 G needle, followed by incubation on ice for 10-15 minutes. Extracts were centrifuged at 720 G for 5 minutes. The supernatant was centrifuged again at 10000 G and the derived pellet provided the mitochondrial fraction and the supernatant provided the cytoplasmic fraction. To extract the mitochondria for measurement of citrate, the pellet from the previous centrifugation was resuspended in PBS and subjected to 3 cycles of freeze-and-thaw in dry ice immersed in ethanol. The fraction was centrifuged again and re-suspended in PBS. The supernatant (containing cytosolic and membrane fractions) was centrifuged multiple times to eliminate particulate material, and was used as the cytosolic fraction.

Surface Plasmon Resonance (SPR). SPR experiments were performed on a Biacore 4000 instrument at room temperature. The NTA sensorchip surface was activated by injecting 0.5 mM $NiCl_2$ for 1 minute. Histidine-tagged recombinant purified SLC25A1 protein (0.07 mg/ml stock concentration) was used as the ligand to capture on the sensor surface. SLC25A1 was dissolved (1:50 dilution) in PBS-P (20 mM phosphate buffer (pH 7.4), 2.7 mM KCl, 137 mM NaCl and 0.05% surfactant P20) buffer and captured onto spots 2 and 4. SLC25A1 was captured to a level of ~3000. PBS-P was used as the capture running buffer. Small molecules were used as analytes to flow over the ligand immobilized surface. Spot 3 of all flow cells were used as reference. The calculated theoretical $R_{max}$ was ~30 RU based on a 1:1 interaction. The kinetics experiments were performed in the presence of HBS-P (10 mM HEPES (pH7.4), 150 mM NaCl, and 0.05% surfactant P20). The flow rate of all the solutions was maintained at 30 µL/min. The analyte concentrations were 0 µM, 1.5216 µM, 3.625 µM, 6.25 µM, 12.5 µM, 25 µM, 50 µM, and 100 µM. Analyte concentrations showing signs of aggregation were excluded from the analysis. Data were analyzed by Biacore BiaEvaluation software for 1:1 steady state binding model.

Immunohistochemistry and analysis of tissue microarrays. The tissue microarrays were obtained from Biomax (Rockville, MD) and included the following: LC10013at: Lung adenocarcinoma with matched adjacent normal lung tissue; HLug-Ade060PG-01: Human lung carcinoma with matched normal adjacent tissue; and OD-CT-RsLug03-002: Human lung carcinoma tissue with matched normal adjacent tissue. The SLC25A1 antibody for IHC was from Abcam (ab174924) used at 1:20 dilution. Visual scoring of the tissue-stained sections was done using a semi-quantitative 4-point scale. This 4-point scale is based on the degree of intensity of staining of the tumor cells and other tissues.

Statistical methods for drug interactions. Relative (R) index calculations were used to test the nature of the interaction between cisplatin, AZD9291, and CTPI-2. Briefly, the R index is calculated as the expected cell survival (Sexp; the product of relative survival in cisplatin and relative survival in CTPI-2) divided by the observed relative survival in the presence of both drugs (Sobs). Sexp/Sobs=1.0 denotes an additive interaction, while >1.0 denotes a synergistic interaction. R index values approaching 2.0 are indicative of strong synergy.

Seahorse extracellular flux analyzer experiments. Cells derived from spheres or monolayer cultures were dissociated and plated overnight at 12,000 cells/well in DMEM with 10% FBS, 5 mM glucose, 1 mM pyruvate, 2 mM glutamine. For CTPI-2 or metformin treatments, the following day the media was replaced with drug/vehicle, and treated for 3 hours.

For the mitochondrial stress test, the media was replaced with DMEM without FBS or bicarbonate, containing 5 mM glucose, 1 mM pyruvate, 2 mM glutamine and placed in a $CO_2$ free incubator at 37° C. for 1 hour, and then transferred to the Xf96 extracellular flux analyzer (Agilent; Santa Clara, CA). The program consisted of 3 measurements of OCR/ECAR before the injection of each drug: oligomycin (0.5 µM final concentration), FCCP (2 µM) and rotenone/antimycin (0.5 µM of each). For the glycolysis stress test, cells were plated overnight as above, and the media was washed twice the following day with DMEM without FBS, bicarbonate, glucose, glutamine or pyruvate, and incubated in this media in a $CO_2$ free incubator with/without drug treatments at 37° C. for 4 hours. There were 3 measurements of OCR/ECAR before each injection: glucose (10 mM final concentration), oligomycin (0.5 or 2-deoxyglucose (50 mM). For the analysis of glutamine oxidation, the protocol was the same as the glucose stress test, but with glutamine being the only compound injected (final concentration 4 mM) and OCR/ECAR measured for 60 minutes. When spheres were analyzed, they were dissociated with StemPro® Accutase® (Thermo Scientific; Waltham, MA) and plated under the same conditions as above as for the monolayers the day before the assay (H1299 spheres), or in stem cell media (See Stem Cell Media) with the wells coated in 15 µL of 2% geltrex diluted in DMEM:F12 (Thermo Scientific). The results were normalized to cell number.

Real time PCR. Total RNA was isolated using Trizol® (Thermo Scientific), and 5 µg of total RNA was treated with DNase I (Thermo Scientific), in the presence of SUPERase.In™ (Thermo Scientific) for 30 minutes at 37° C. EDTA was then added to 5 mM and the DNase I heat inactivated at 75° C. for 10 minutes. After adding $MgCl_2$ to 5 mM, cDNA was generated using Superscript IV (Thermo Scientific) and random hexamers following the manufacturer's instructions. Real time PCR was carried out using PowerUp™ SYBR® Green Master Mix (Thermo Scientific), using the reference genes glyceraldehyde-3-phosphate dehydrogenase (GAPDH) and small nuclear ribonucleoprotein D3 (SNRPD3). The gene expression was normalized to the two reference genes, and the relative gene expression fold changes calculated using the ΔΔCT method. Dissociation curves were analyzed and showed single amplification products to confirm the specificity of each primer pair, and −RT samples run to verify no genomic DNA contamination was present. The primer sequences were as follows:

GAPDH:
Forward:
(SEQ ID NO: 1)
CCCTCCGGGAAACTGTGGCG;

Reverse:
(SEQ ID NO: 2)
GCAGTGGGGACACGGAAGGC;

SNRPD3:
Forward:
(SEQ ID NO: 3)
GAGGACAACATGAACTGCCA;

Reverse:
(SEQ ID NO: 4)
TAACATGGGTGCGTTCTTCA;

Notch-1:
Forward:
(SEQ ID NO: 5)
GGTGAGACCTGCCTGAATG;

Reverse:
(SEQ ID NO: 6)
GTTCTTGCAGGGGGTGC;

KLF4: Forward:
(SEQ ID NO: 7)
CACCATGGACCCGGGCGTGGCTGCCAGAAA;

Reverse:
(SEQ ID NO: 8)
AAGCTGACTTGCTGGGAACTTGACC;

Oct2:
Forward:
(SEQ ID NO: 9)
AGATCAAGGCTGAAGACCCC;

Reverse:
(SEQ ID NO: 10)
GAGGAGCTGCTGTATGTCCC;

SLC25A1:
Forward:
(SEQ ID NO: 11)
CCCCATGGAGACCATCAAG;

Reverse:
(SEQ ID NO: 12)
CCTGGTACGTCCCCTTCAG.
Nanog (Bio-rad, Cat # 10025636);
Sox2 (Bio-rad, Cat # 10025636).

Modeling of human SLC25A1 and identification of SLC25A1 inhibitor. The in silico homology model for human SLC25A1 was derived from the Protein Model Portal of the PSI-Nature Structural Biology Knowledgebase (Uniprot ID: P53007). The docking pose for citrate, CTPI-1, and CTPI-2 were performed using UCSF DOCK6.7 software. Briefly, receptor spheres were generated using the program SPHGEN cover the area identified by Kaplan as Site 2. The ligand flexibility option was used for the docking and the top scoring conformation was minimized to give the final pose.

Melting points of the identified compounds were determined in open capillary tubes on a Electrothermal melting point apparatus MEL-TEMP and are uncorrected. All NMR spectra were recorded on Bruker DRX spectrometer (400 MHz) spectrometer. NMR data were collected at 400 MHz for $^1$H and 100 MHz for $^{13}$C NMR. The chemical shifts are expressed in parts per million (ppm) downfield from tetramethylsilane (TMS) as the internal standard in deuterated solvent and coupling constants (J) are in hertz (Hz). Data are reported as follows: chemical shift, integration, multiplicity (s is singlet, d is doublet, t is triplet, dd is doublet of doublets, m is multiplet), and coupling constants. All solvents and reagents were obtained from commercial suppliers and used without further purification. All evaporations were carried out in vacuo with a Büchi rotary evaporator. Thin-layer chromatography (TLC) was performed on Merck silica gel plates 60F254 visualized by UV light at 254 nm or 310 nm. Flash chromatography was carried out using flash-grade silica gel 60 (40-63 micron, 230-400 mesh).

Mice and treatments. To produce tumor xenografts, $5 \times 10^6$ cells derived from either monolayer cultures or GMSC expanded spheres were dissociated with Accutase, resuspended in PBS, and injected subcutaneously in the flanks of female balb athymic mice. Once detectable tumors started to form, their sizes were measured with a caliper in three dimensions and mice were randomized in the different treatment groups. For drug treatments, mice were randomized to receive either PBS, DMSO, or CTPI-2 at a concentration of 26 mg/kg which was administered via intraperitoneal route on alternating days. Cisplatin was administered at 26 mg/kg every three or four days. AZD9291 was administered at 25/mg/Kg every 3 days. Serial measurements were made every day after the identification of the initial tumor mass to determine growth curves in vivo. Tumor volume was calculated using the formula for a prolate spheroid: volume=$(4/3) \times a^2 b$, where a is the width and b is the length. All animals were sacrificed when the tumors exceeded 1.5 cm. At the completion of experiments, tumors were excised, weighed, and the statistical significances of differences in tumor volume were assessed. Animals were monitored once a week for the presence of signs of disease, particularly neurological disturbances or weight loss, and they were weighed periodically.

Statistics. For the animal studies, power calculations for each treatment group were first determined. The number of animals was calculated to detect a 50% difference at alpha=0.05 and power=0.8. Statistical significance was assessed using both unpaired, two-tailed Student t test, and analysis of variance (ANOVA). Significant differences are indicated using the standard Michelin Guide scale (P<0.05, significant; P<0.01, highly significant; P<0.001, extremely significant).

Results

Figure 8A:
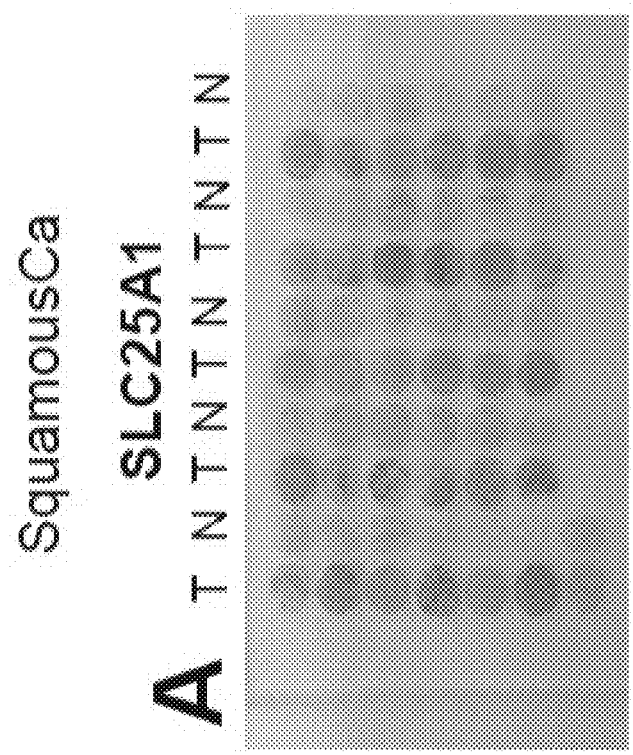
FIGS. 8A-C show the expression of SLC25A1 in tumor arrays.
Figure 8B:
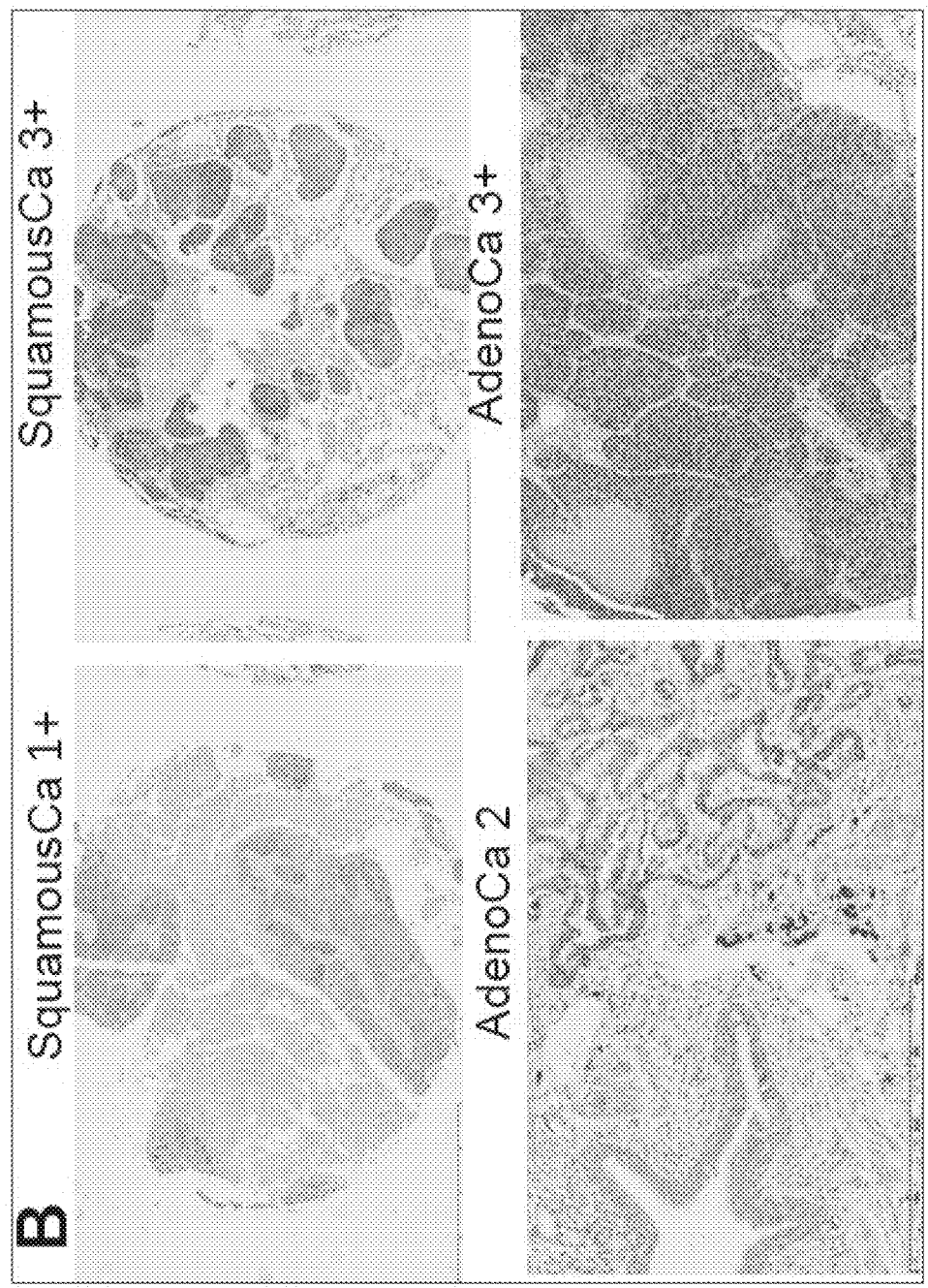
Figure 8C:
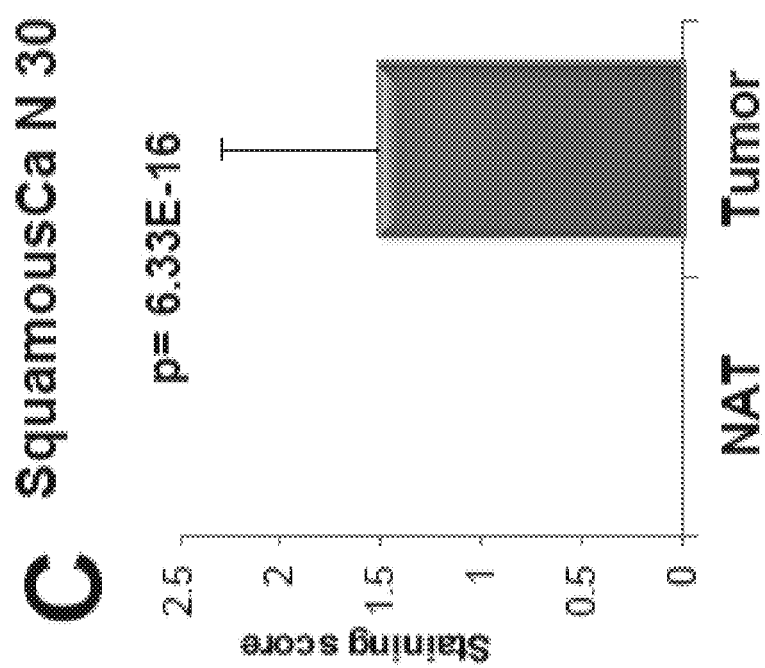

SLC25A1 is over-expressed in lung cancers and is necessary for lung CSCs enrichment. To elucidate the function of SLC25A1 in lung cancer, an immunohistochemical analysis of tissue microarrays (TMAs) containing 90 lung cancers, which included both adeno- and squamous carcinomas, was performed. All of the TMAs included core biopsies from matched tumor and normal adjacent tissues (NAT) and one also contained matched lymph nodes positive for metastasis. The majority of adenocarcinomas (FIGS. 1A-C) and squamous carcinomas (FIGS. 8A-C) were immunoreactive for SLC25A1 whereas in normal tissues the respiratory epithelium showed only very weak positivity. The matched metastatic foci in lymph nodes of adenocarcinomas were all positive for SLC25A1 (FIG. 1B-C), demonstrating that SLC25A1 expression is highly expressed in metastatic sites.

Figure 9A:
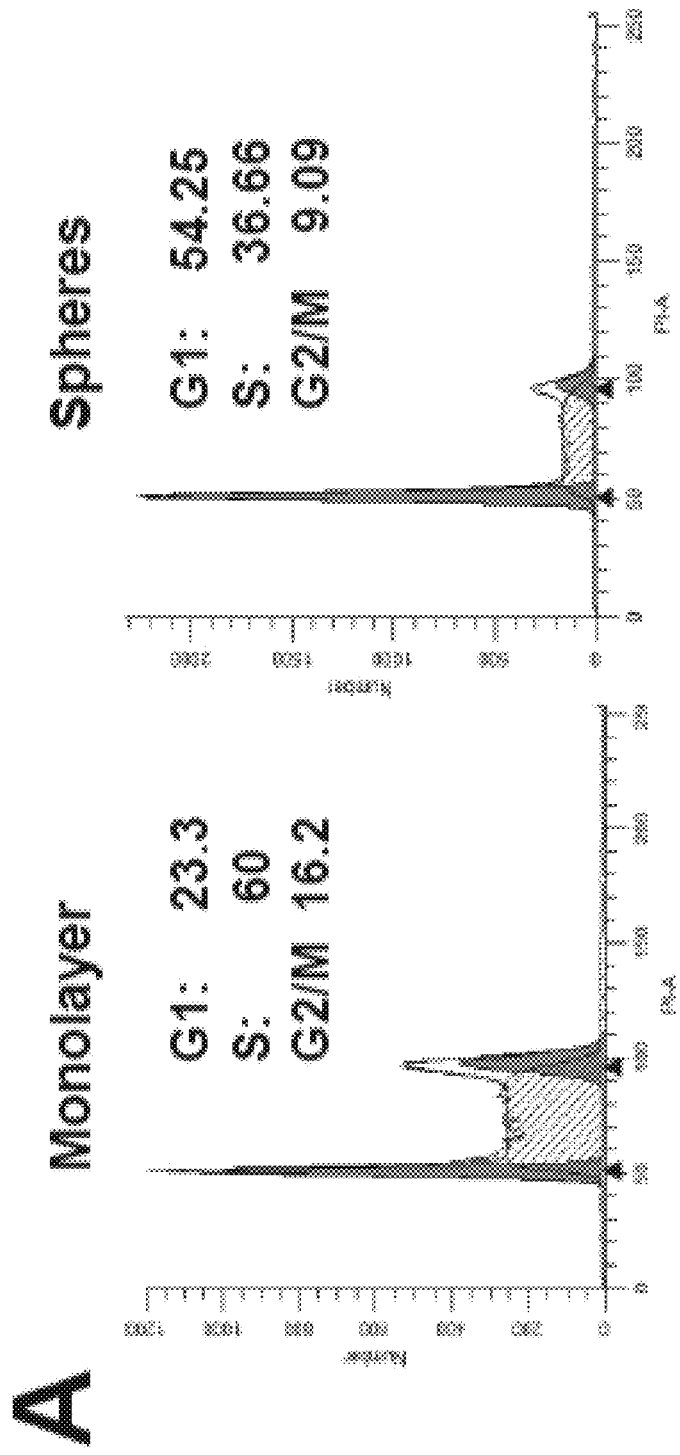
Figure 9B:
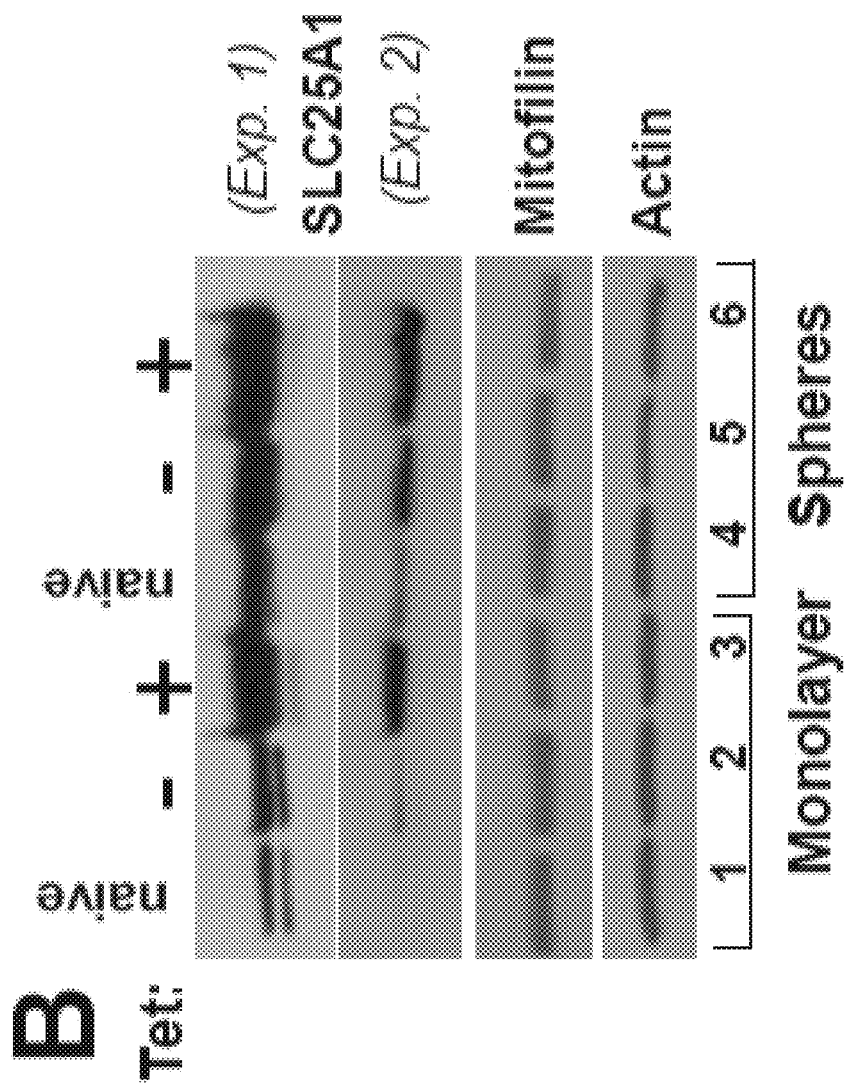
Figure 9E:
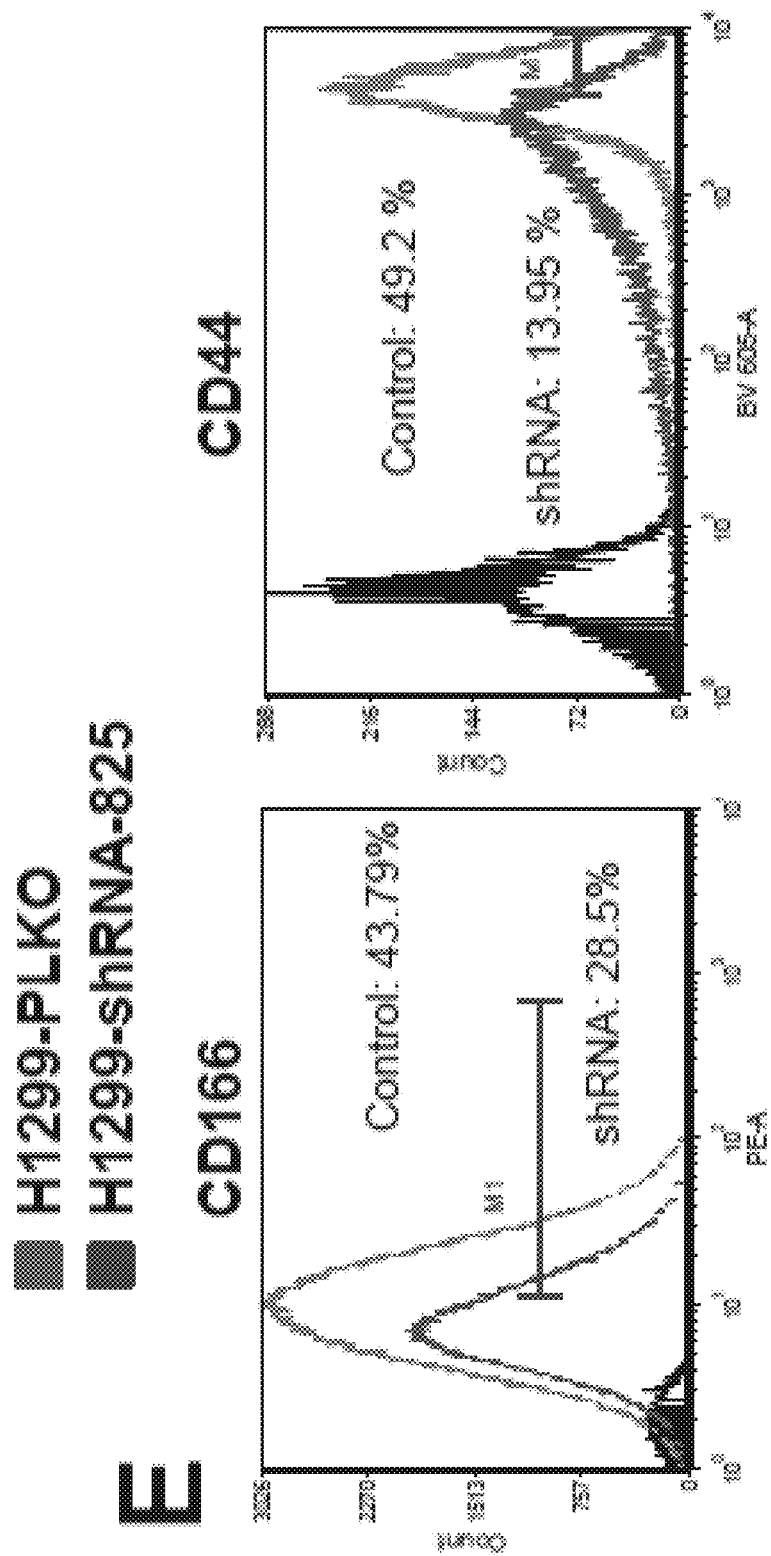
Figure 9F:
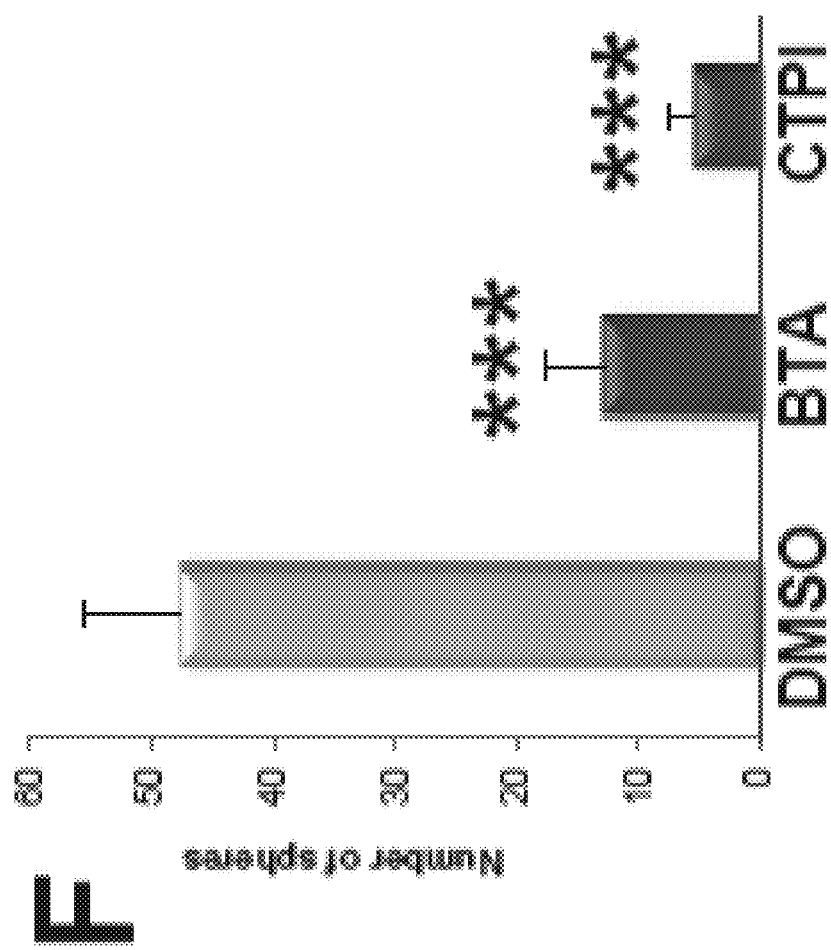

It was previously reported that SLC25A1 expressing cells are highly tumorigenic when injected in nude mice. CSCs are the main source of cancer initiation. It was determined whether SLC25A1 affects the expansion of this population. Anchorage-independent spheroid assays which lead to CSC enrichment were employed because in these conditions differentiated cells undergo anoikis, while CSCs are able to expand. Cells derived from the lung adenocarcinoma cell line, H1299, grown as spheres, exhibited a contraction of the G1 phase of the cell cycle compared to monolayer cultures (FIG. 9A), consistent with a quiescent, non-replicating state, and a stark enrichment of the stem cell markers KLF4, Notch-1, Nanog, Sox2 and Oc2 as well as of SLC25A1 itself (FIG. 1D). Accordingly, the SLC25A1 protein was enriched in H1299 spheres compared to 2D cultures while the mitochondrial amount was unaffected, as indicated by the comparable levels of mitofilin (FIG. 9B). Thus, 3D cultures model CSC growth and SLC25A1 is co-expressed with stemness genes. Compared to naïve H1299, spheres overexpressing SLC25A1 via a tetracycline inducible cDNA were enriched for Notch-1, Oct2 (FIG. 1E), as well as for CD133, CD166 and the CD44high/CD24low population which possessed self-renewal capabilities (FIG. 1F-H; quantified in FIG. 1I). Given that self-renewal is necessary for maintaining the CSC pool, second generation spheres were monitored by dissociating the first generation spheres and re-plating them in semisolid media (methyl-cellulose), which prevents cell-to-cell contacts and, thus, only allows growth of monoclonal cell populations. Expression of SLC25A1 in H1299 cells enhanced self-renewal relative to naive H1299 (FIG. 9C) and led to a significant enhancement of the number and size of first and second generation spheres (FIG. 1J). The effects of the SLC25A1 knock-down with two different shRNAs were then expressed. Although proliferation rates were reduced by the SLC25A1 knock-down, cells continued to grow and could be propagated as two-dimensional cultures (FIG. 9D). In contrast with their ability to grow as a monolayer, cells expressing these shRNAs had severely compromised sphere forming capacity (FIG. 1K) and reduced levels of stem cell markers (FIG. 9E). Similarly to the shRNAs, treatment with two previously validated SLC25A1 inhibitors, benzenetricarboxylate (BTA) and Citrate-Transporter Inhibitor-1 (CTPI-1), also reduced sphere forming capacity (FIG. 9F).

These data indicate that SLC25A1 promotes the expansion and self-renewal of CSCs and highlight the importance of modeling CSC proliferation in three-dimensional spheroid systems.

Identification of a novel SLC25A1 inhibitor compound. The finding that SLC25A1 promotes CSC expansion suggests that SLC25A1 inhibitors target this cell population. The best known SLC25A1 inhibitor is BTA, which, owing to a negative partition coefficient and topical polar surface area, does not easily cross the cell membrane, such that millimolar concentration of this drug are required for inhibition of SLC25A1. A second compound, CTPI-1, was described as an inhibitor of the yeast SLC25A1 protein. By employing surface plasmon resonance (SPR) spectroscopy it was found, however, that CTPI-1 exhibits suboptimal binding to the human protein ($K_D$ 63.6 μM) and displays growth inhibitory activity at millimolar range of concentrations in human cells (FIGS. 2A and 2E; FIG. 10A). A key difference between yeast and human SLC25A1 is that Arg181 in the yeast homolog is replaced by Lys190 in the human protein.

To optimize compounds for human SLC25A1, an in silico homology model was derived and docking experiments were performed. By exchanging the Z group to a nitro substituent with the chlorine atom for the Y group of CTPI-1, a compound (CTPI-2) was identified that exhibits an experimental $K_D$ of 5.3 μM and the best in silico docking score of all known SLC25A1 inhibitors (FIG. 2A-C; FIG. 10B). The docking model shows that CTPI-1 interacts with SLC25A1 through a network of hydrogen bonds involving amino acids known to contribute to citrate binding, specifically Lys190, Arg282, and Arg285, allowing for a closed conformation, which takes advantage of intramolecular pi-pi stacking of the two aromatic moieties (FIG. 2C). In comparison, CTPI-2 affords a related binding mode as CTPI-1 between the ligand and Arg282 and Lys90, but the sulfonamide moiety aligns in the direction of Lys190 for CTPI-2 rather than in the direction of Arg282 as seen with CTPI-1. In the binding mode for CTPI-2, a π-cation interaction exists between Lys245 and the aromatic ring of CTPI-2 that contains the carboxylate group. These interactions can contribute to a lower $K_D$ for the binding of CTPI-2 to the SLC25A1 protein.

Figure 2D:
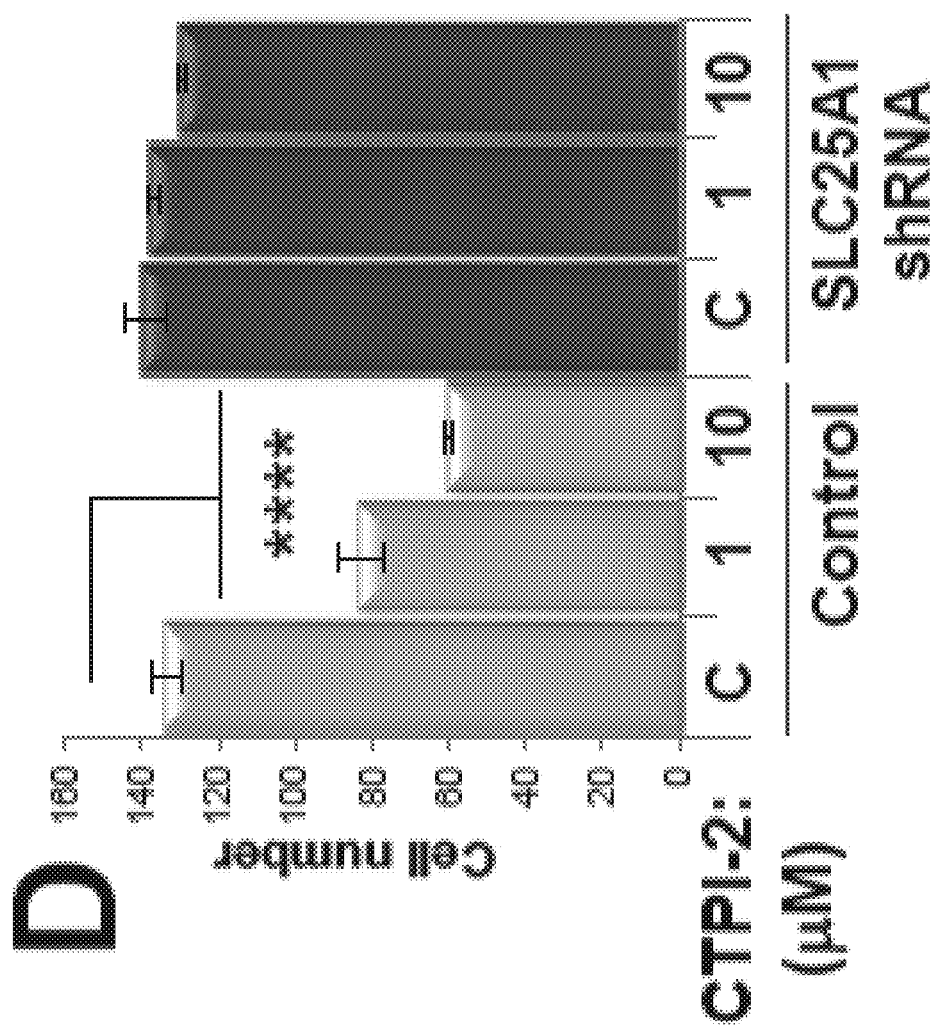
Figure 2E:
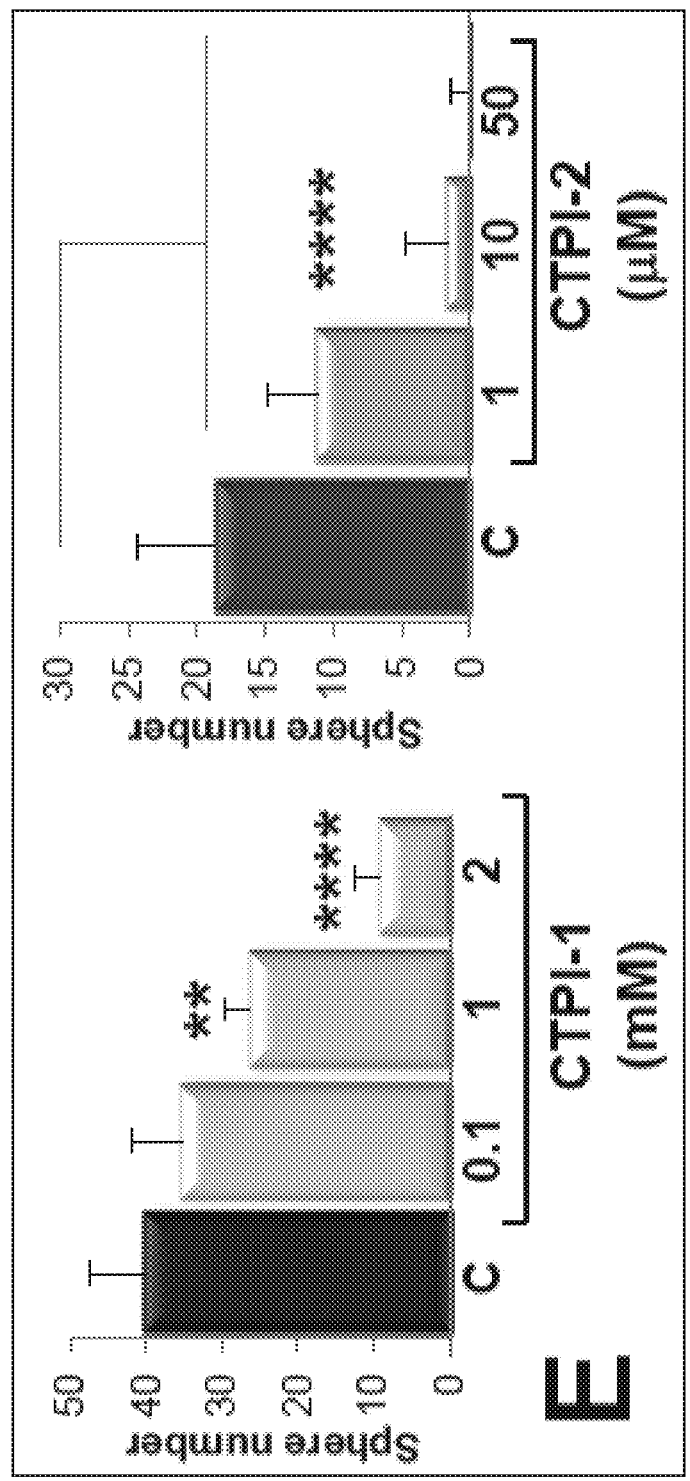
Figure 2F:
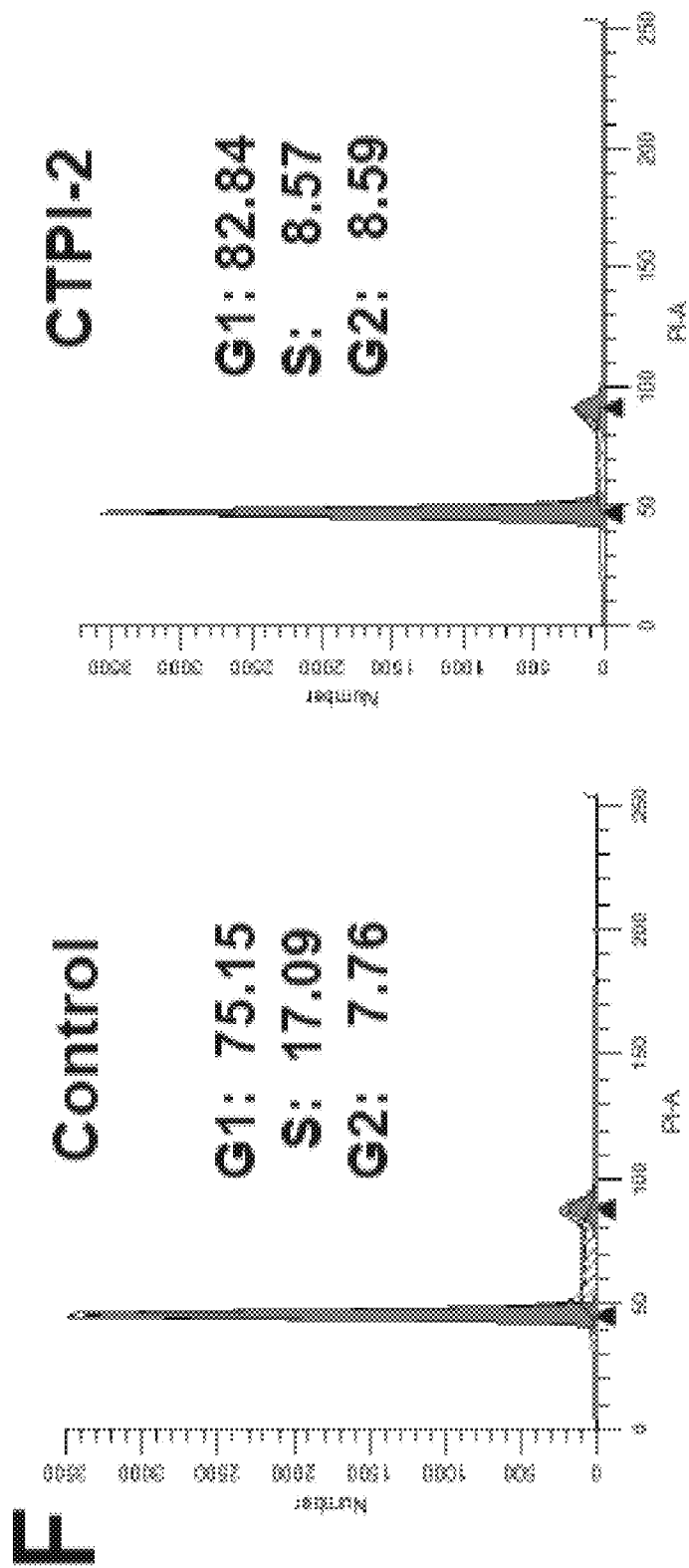

In cells expressing the SLC25A1-shRNA, CTPI-2 failed to inhibit proliferation (FIG. 2D), demonstrating that SLC25A1 is a bona fide determinant of the mechanism of action of this drug. Further, as predicted based on the SPR data, CTPI-2 inhibited sphere forming capacity more efficiently than CTPI-1 (FIG. 2E) and its activity was significantly more prominent in spheres than in 2D cultures (compare FIG. 2D and FIG. 2E). CTPI-2 was modestly cytostatic in spheres (FIG. 2F). Thus the reduction of sphere forming capacity is not merely due to induction of cell death.

Figure 3A:
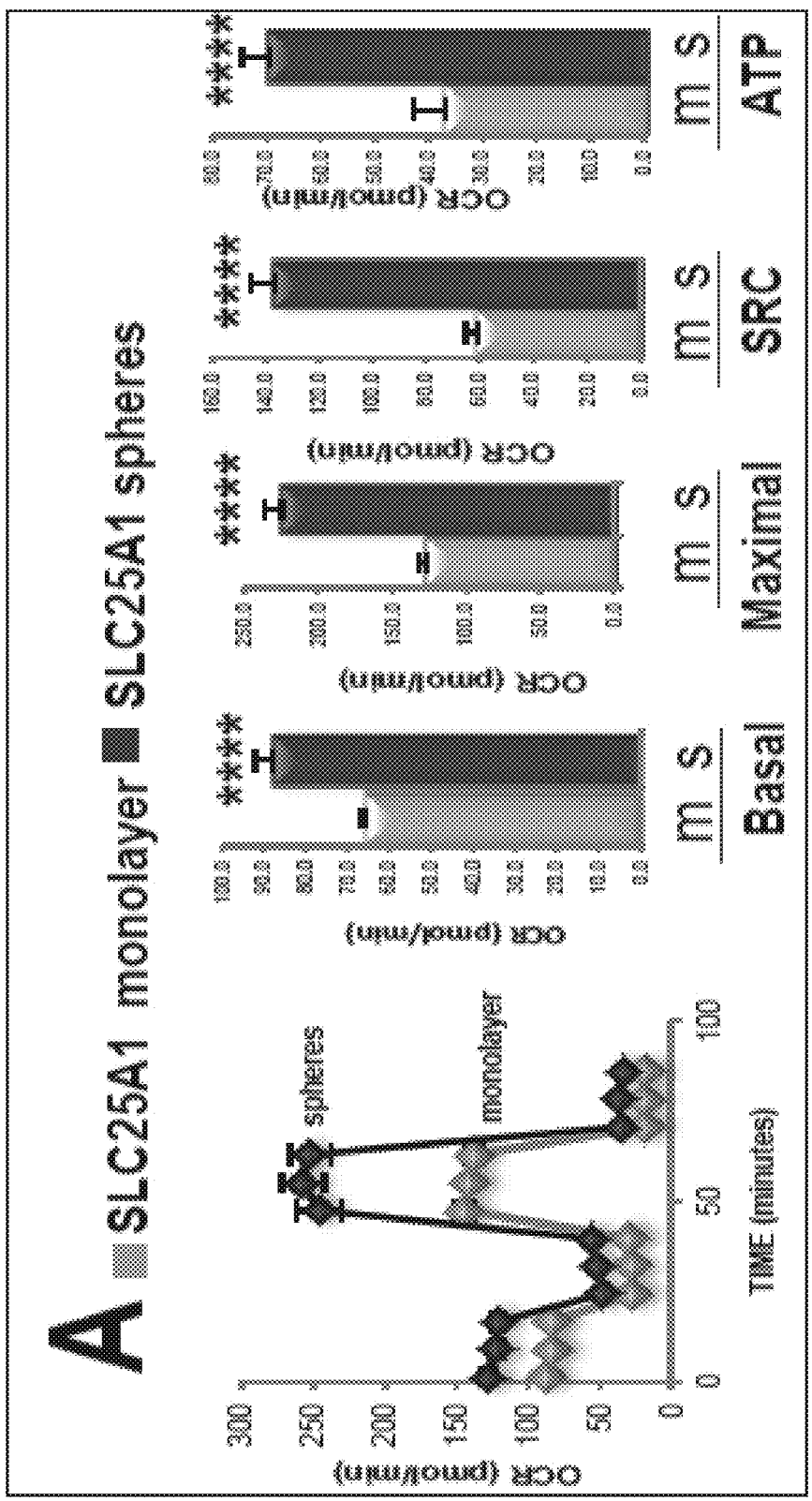
Figure 11A:
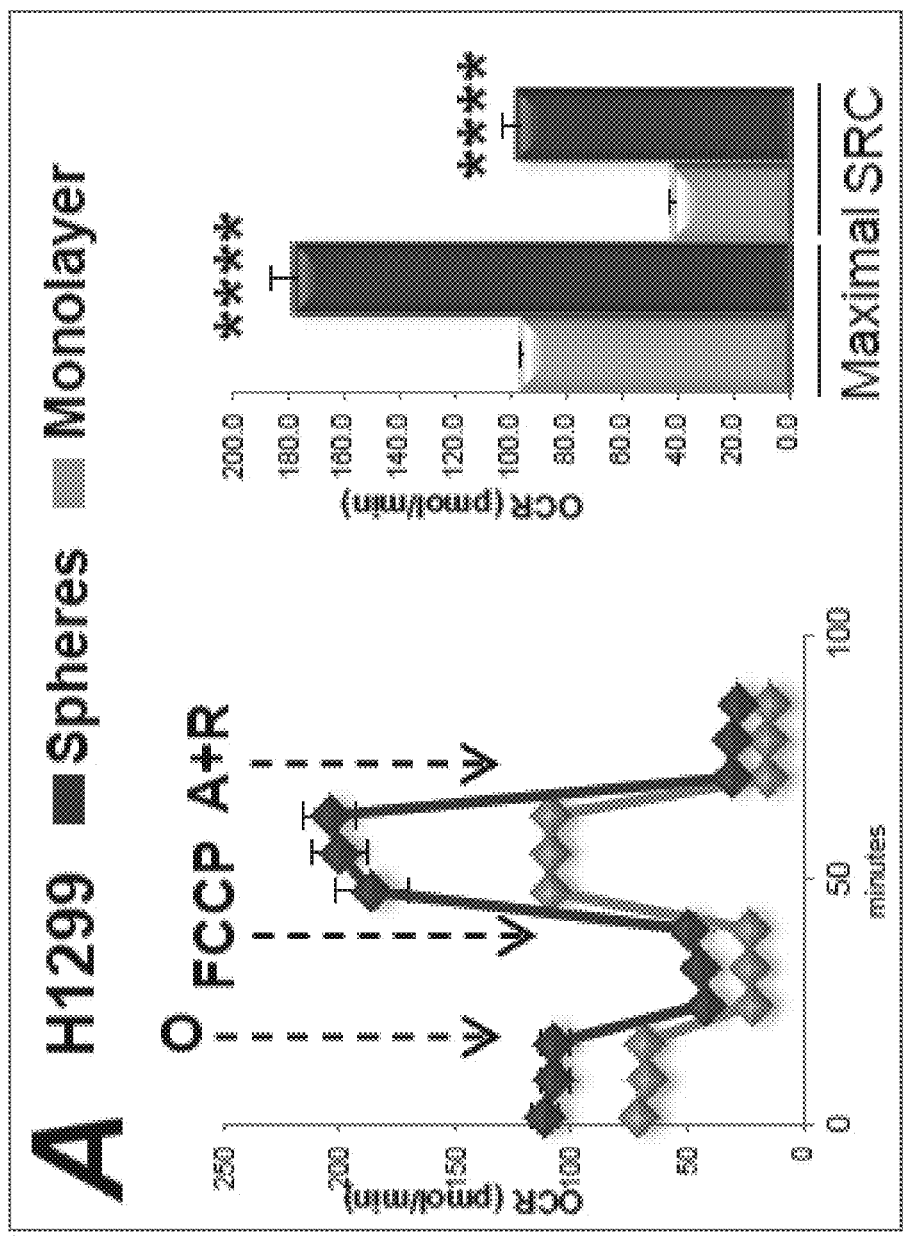
FIGS. 11A-C show the metabolic activities of CTPI-2.
Figure 11B:
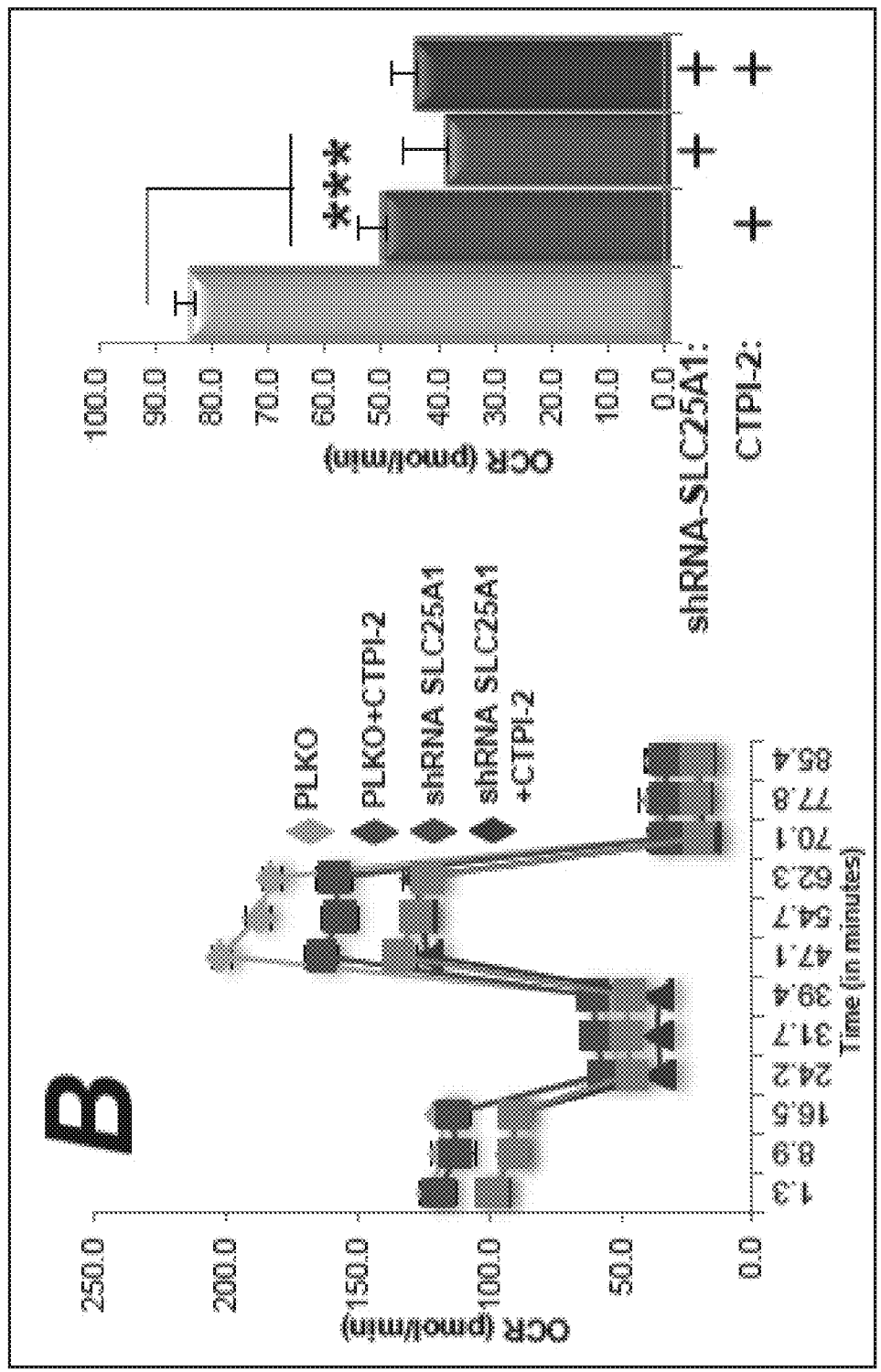

A SLC25A1-mediated citrate import pathway supports mitochondrial oxidative phosphorylation in lung CSCs. To investigate the link between the ability of SLC25A1 to promote CSC expansion and their mitochondrial metabolism, oxygen consumption rates (OCR) of monolayer or sphere cultures were measured with and without SLC25A1 over-expression. Relative to 2D cultures, H1299 cells derived from spheres showed higher levels of OCR (FIG. 11A) and expression of SLC25A1 enhanced basal, maximal and spare respiratory capacity (SRC), as well as mitochondrial ATP output in spheres (FIG. 3A). In contrast, treatment with the CTPI-2 inhibited respiratory capacity in a dose-dependent fashion and this inhibition was more prominent in spheres compared to monolayers (FIG. 3B-C). H1299 cells expressing the SLC25A1 shRNA also exhibited reduced OCR levels relative to monolayer cultures and CTPI-2 failed to affect the respiratory activity of these cells, demonstrating specificity of CTPI-2 for SLC25A1 (FIG. 11B).

SLC25A1 has been shown to function by exporting citrate from the mitochondria to the cytoplasm; however, a reverse citrate import pathway from the cytoplasm to the mitochondria has also been documented in purified mitochondria. In the mitochondria, citrate is utilized for the Kreb cycle and ATP production via oxidative phosphorylation. It was next determined whether changes in the export/import activity of this protein can account for such differences. A short-time inhibition (4 hours) of SLC25A1 with CTPI-2 induced accumulation of mitochondrial citrate in 2D cultures, coinciding with a reduction of cytoplasmic citrate (FIG. 3D, lanes 1 and 2 versus lanes 5 and 6, respectively). In contrast, CTPI-2 starkly decreased mitochondrial citrate in spheres (FIG. 3D, lane 4 versus 3), albeit without affecting the cytosolic citrate (FIG. 3D, lane 7 versus 8). In the mitochondria, citrate is converted to TCA cycle intermediates, including malate and succinate. Therefore, a deficit in the citrate import function of SLC25A1 can affect the availability of these substrates. Consistent with this, the addition of citrate itself or of succinate or malate rescued mitochondrial respiratory capacity as well as the self-renewal ability in CTPI-2 treated cells (FIG. 3E-G).

Figure 3H:
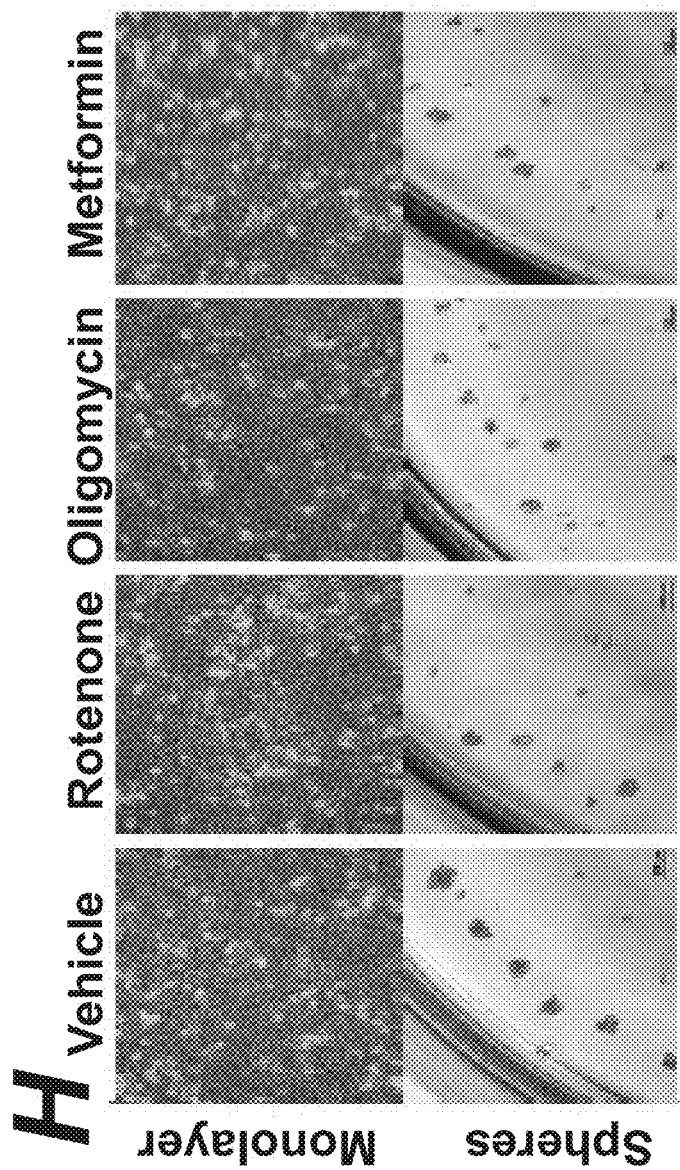

To confirm that the mitochondrial respiration is required for the growth of CSCs, the activities of other mitochondrial targeting drugs, specifically rotenone, metformin, oligomycin, and CPI-613, were studied. CPI-613 is in clinical trials for the treatment of advanced solid tumors and is a dual inhibitor of pyruvate dehydrogenase and of α-ketoglutarate dehydrogenase, two enzymes that promote citrate production and the TCA cycle, therefore in part acting on the same pathway as CTPI-2. At concentrations at which rotenone, oligomycyn and metformin, displayed no anti-proliferative activity in 2D cultures, the compounds all significantly reduced self-renewal (FIGS. 3H and 3I). CPI-613 and CTPI-2 exhibited anti-proliferative activity at comparable ranges of concentrations and, similarly to CTPI-2, CPI-613 was also more effective in sphere forming assays than in monolayer cultures (FIG. 3J). Therefore, the mitochondrial respiratory activity and the citrate production and transport pathway are targets with elective effects on CSCs.

Figure 11C:
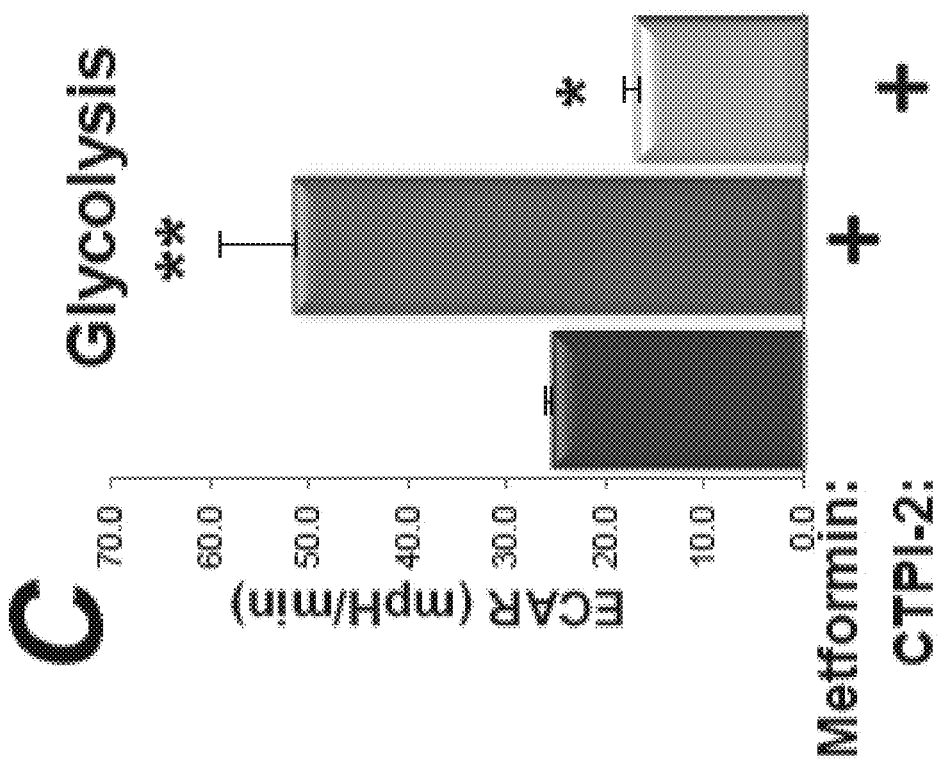

CTPI-2 is a unique regulator of glycolysis. Cancer cells switch toward a compensatory increase in aerobic glycolysis to derive energy when mitochondrial activity is inhibited and the majority of mitochondrial inhibitors enhance glycolytic rates, leading to the development of resistance. The anti-diabetic drug metformin, which has been vastly studied as a complex I inhibitor, has preferential anti-tumor activity against pancreatic CSCs, but resistance to metformin occurs through the activation of glycolysis. First, it was found that extracellular acidification rates (ECAR), which are indicative of glycolysis, were increased in monolayer cultures compared to spheroids, demonstrating that differentiated cells preferentially utilize glucose for aerobic glycolysis (FIGS. 4A and B). The assessment of the glucose-driven OCR levels indicated that in sphere-grown CSCs glucose is instead diverted towards mitochondrial respiration (FIG. 4C). These results are consistent with the switch towards oxidative mitochondrial metabolism in CSCs described before. Second, ECAR rates were starkly induced in monolayer cultures treated with CTPI-2 and this coincided with an increase in lactic acid levels (FIG. 4D, lane 4 versus 2; FIG. 4E), demonstrating that inhibition of SLC25A1 activity drives glycolysis in differentiated cells. However, such enhancement was completely lost in spheres where both ECAR and lactic acid levels remained unchanged or were slightly diminished (FIG. 4D, lane 8 versus 6; FIG. 4E). This effect of CTPI-2 was opposite to that exhibited by metformin that, as expected, enhanced glycolytic rates (FIG. 11C).

Figure 4F:
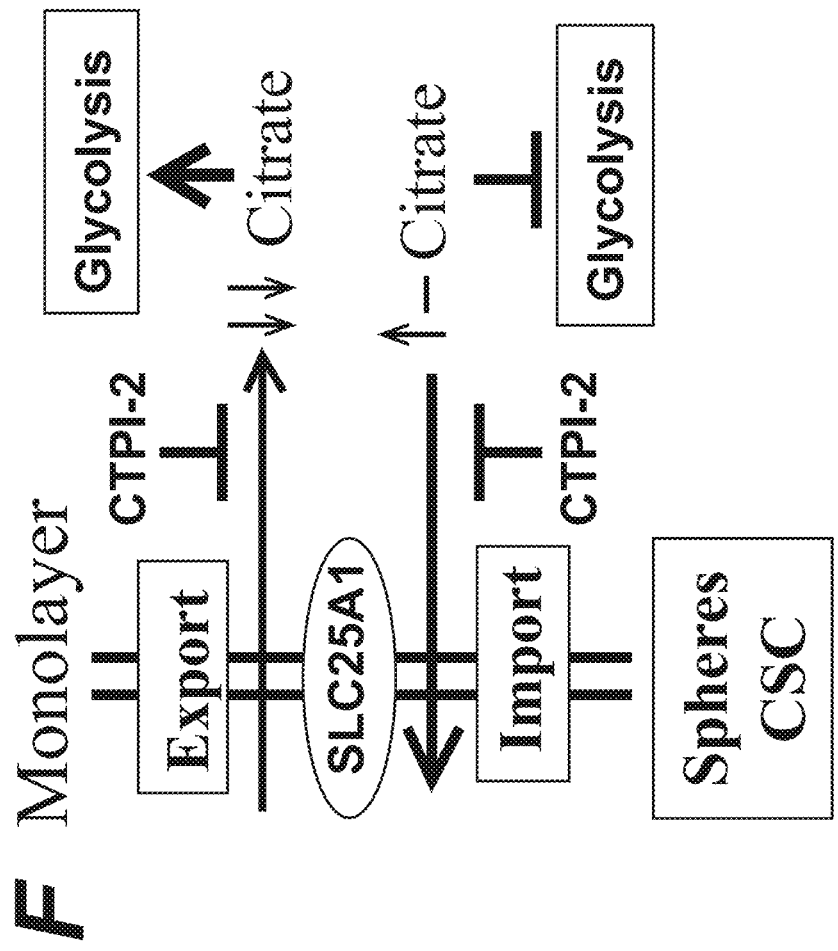
Figure 4G:
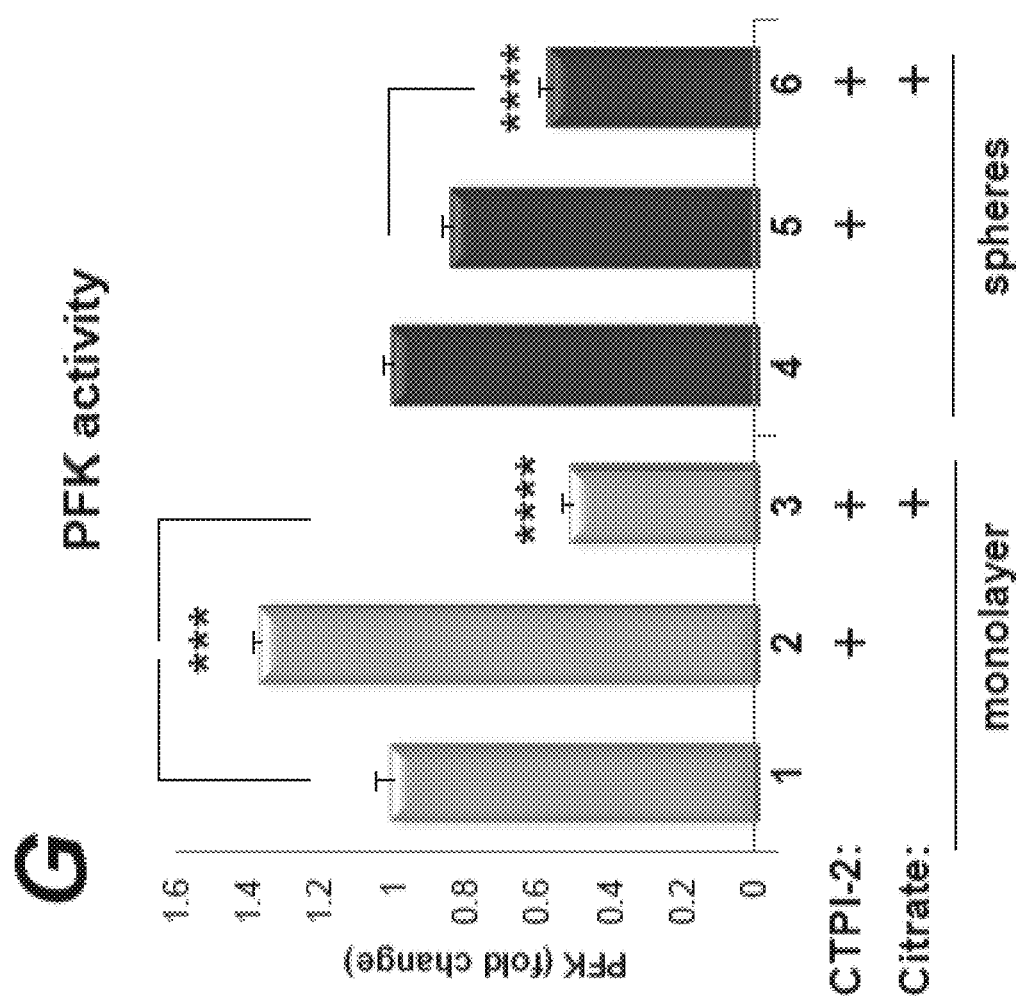

Because cytoplasmic citrate is a negative allosteric regulator of phosphofructokinase (PFK), the key enzyme that controls glycolysis, it was determined whether this unique mode of action relies upon CTPI-2 ability to differentially regulate the cytoplasmic concentration of citrate, which is lowered in monolayer cultures but remains stable in spheres (see FIG. 3D), thus allowing citrate to maintain a sustained block on glycolysis in the latter but not in the former (depicted in FIG. 4F). PFK activity was enhanced by CTPI-2 in monolayer differentiated cultures and such enhancement was completely reverted by citrate (FIG. 4G, lanes 3 versus lane 2). In contrast, PFK activity was unchanged in spheres (FIG. 4G, lane 5).

Although other pathways may also contribute to regulate the cytoplasmic concentration of citrate in CSCs, these data lead to the important conclusion that CTPI-2 differs from other known mitochondrial inhibitors in that it does not induce a compensatory increase in glycolysis in CSCs. Therefore, while differentiated cells escape the block of oxidative phosphorylation exerted by CTPI-2 by deriving energy through aerobic glycolysis, in CSCs this switch is prevented and consequently, at least in this respect, this drug is more potent in limiting the energetic supplies for this cell population. Such differential effects of CTPI-2 could also potentially explain its more potent activity in CSCs.

Figure 5A:
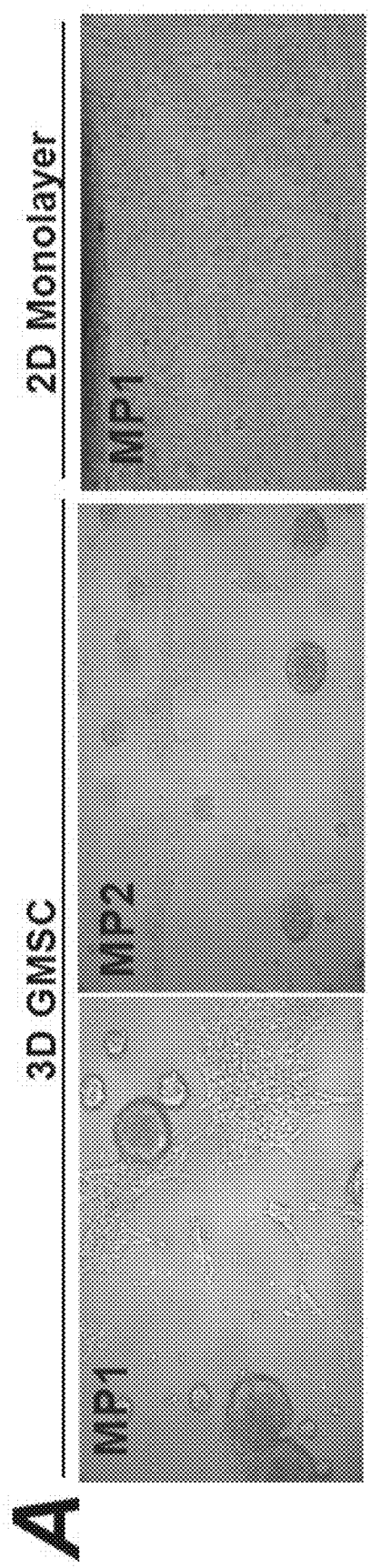
FIGS. 5A-F show that patient-derived CSCs depend on SLC25A1 driven mitochondrial respiration for survival and matrix invasion.

SLC25A1 inhibition blunts mitochondrial respiratory activity and the invasive ability in patient-derived CSCs. Experiments were then performed on clinically relevant models of NSCLC. Cancer stem cells can be isolated from established canonical cells in culture, but it is more difficult to isolate them from biological specimens, in part due to the fact that CSCs undergo rapid differentiation in the growth conditions employed by most laboratories which nearly universally utilize animal-derived serum. Culturing of lung cancer primary tumor samples as tumor spheres in the absence of serum leads to enrichment of CSCs endowed with tumor initiating capability. For the experiments, a system was developed that utilizes a dual matrix composition (Geltrex and human-derived Maxgel) and growth medium optimized to prevent differentiation through the elimination of animal-derived serum. The medium is supplemented with components that have been employed for the growth of pluripotent stem cells (see materials and methods). This system is referred to herein as GMSC (Geltrex-Maxgel, Stem Cell media). It has been found able to support tumor cell enrichment more rapidly and more efficiently than other culturing conditions (FIG. 12). Moreover, while primary tumors frequently lose viability if established directly as adherent two-dimensional cultures (FIG. 12), once stabilized as GMSC, these cells can be grown also as 2D cultures. Functionally, GMSC-expanded cells maintain a three-dimensional architecture, growing as spheroids attached to the ECM matrix (FIG. 5A), thus more faithfully recapitulating the growth of tumors in tissues. Importantly, when injected into immuno-compromised mice, these GMSC cultures form tumors that resemble the histological characteristics of the tumor of origin (FIG. 13).

Figure 5B:
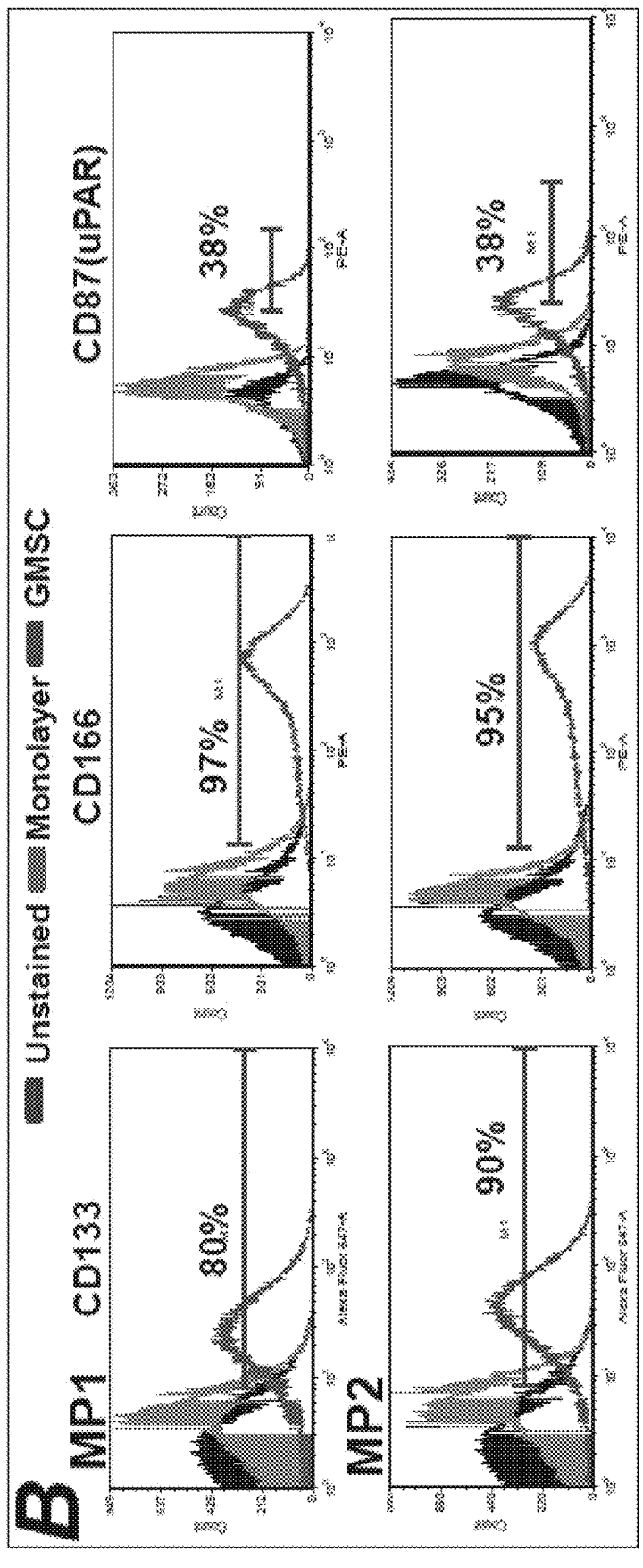
Figure 5C:
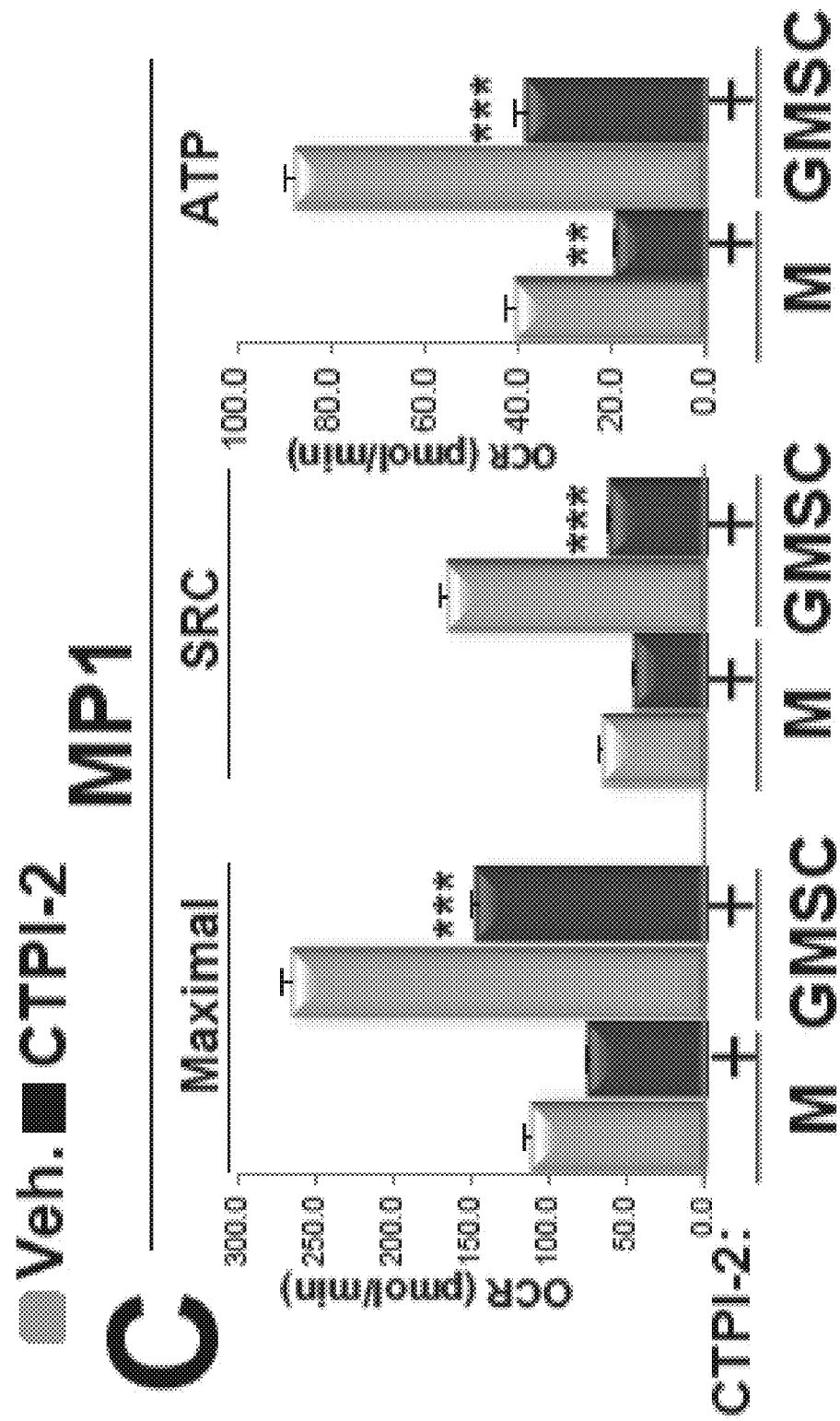
Figure 5D:
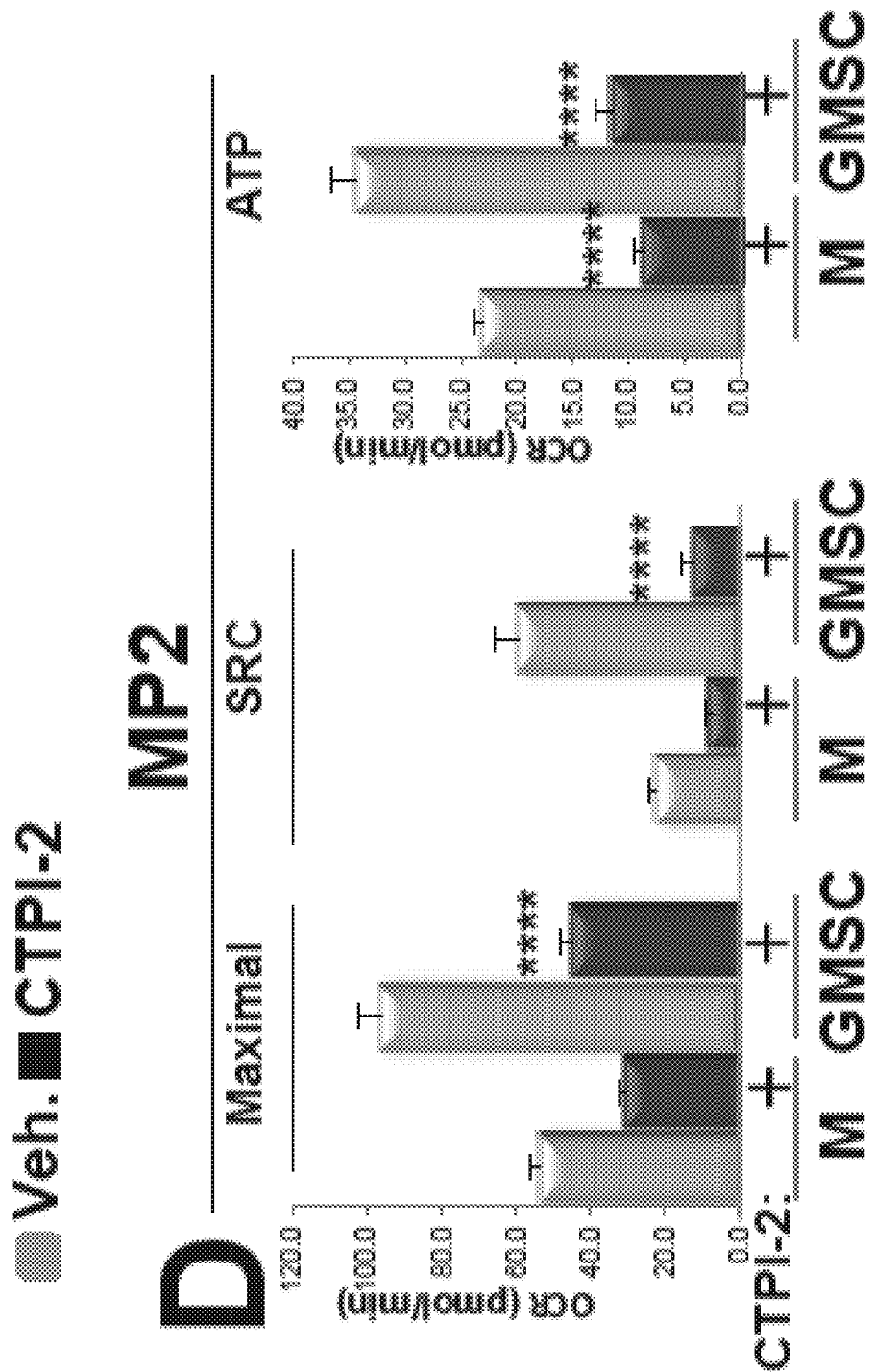
Figure 14A:
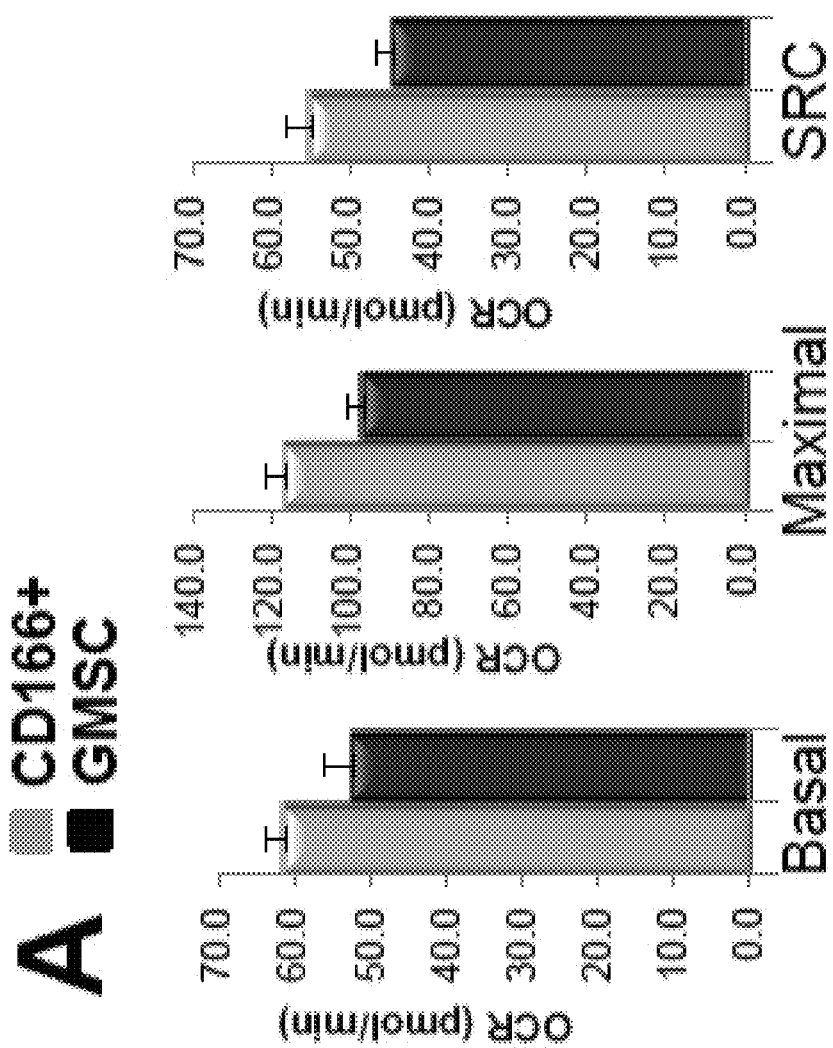
Figure 14D:
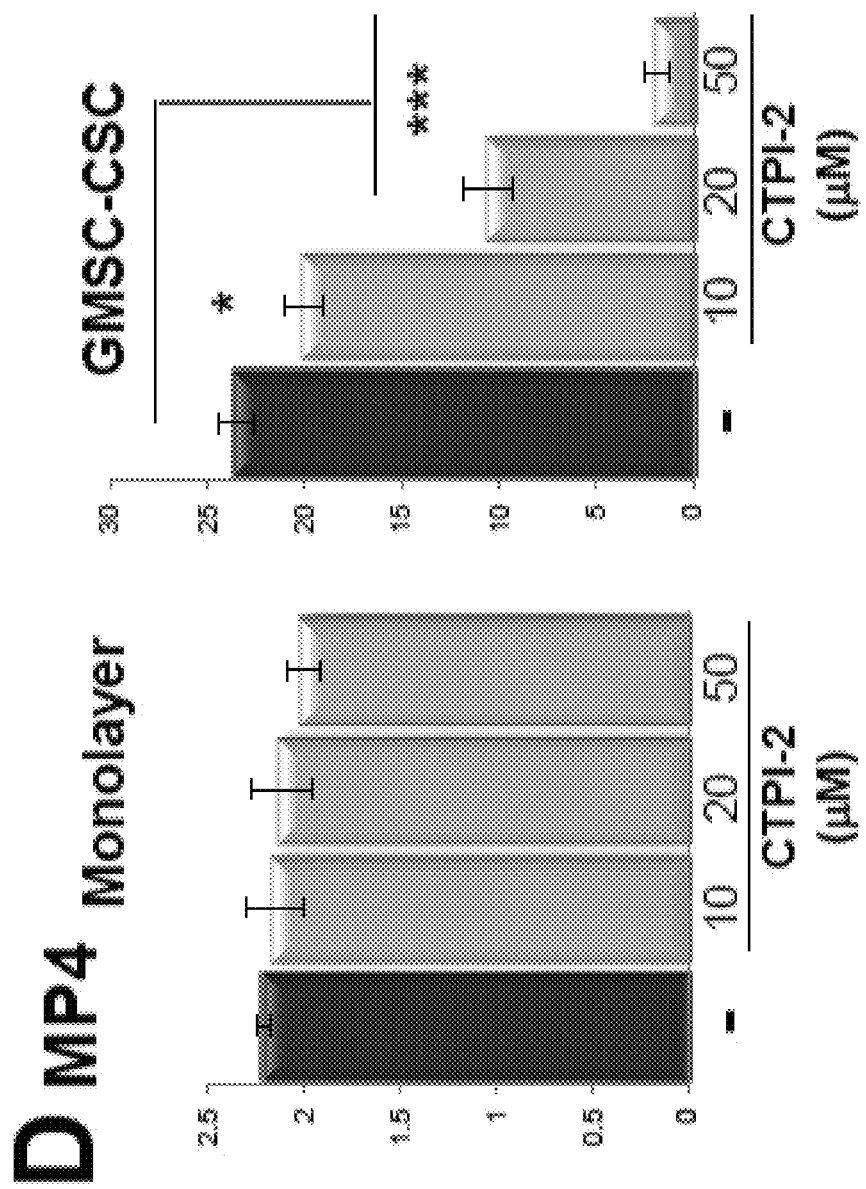

Stem cell markers and mitochondrial OCR were analyzed. The MP1 or MP2 NSCLC cells grown as 2D cultures had poor expression of stem cell markers, consistent with differentiation in these conditions while GMSC cells showed a stark enrichment (nearly 100%) of CD166, CD133, as well as of the urokinase plasminogen activator receptor CD87 (FIG. 5B), which are all lung cancer stem cell markers. Oxygen consumption rates, basal, SRC, and mitochondrial ATP output were increased in GMSC cells relative to differentiated cells and such increase was reverted by CTPI-2 more prominently in CSCs than in monolayer cultures (FIGS. 5C and 5D). When analyzed individually, the CD166 positive cells isolated by FACS cell sorting exhibited nearly identical respiratory capacity to the whole population of GMSC cells (FIG. 14A), demonstrating that GMSC-grown cells model the mitochondrial activity of CSCs. Moreover, CTPI-2 blunted self-renewal and sphere forming ability of these CSCs and several others GMSC, but not differentiated monolayer cultures were highly sensitive to CTPI-2 (FIG. 14B-D).

Figure 5E:
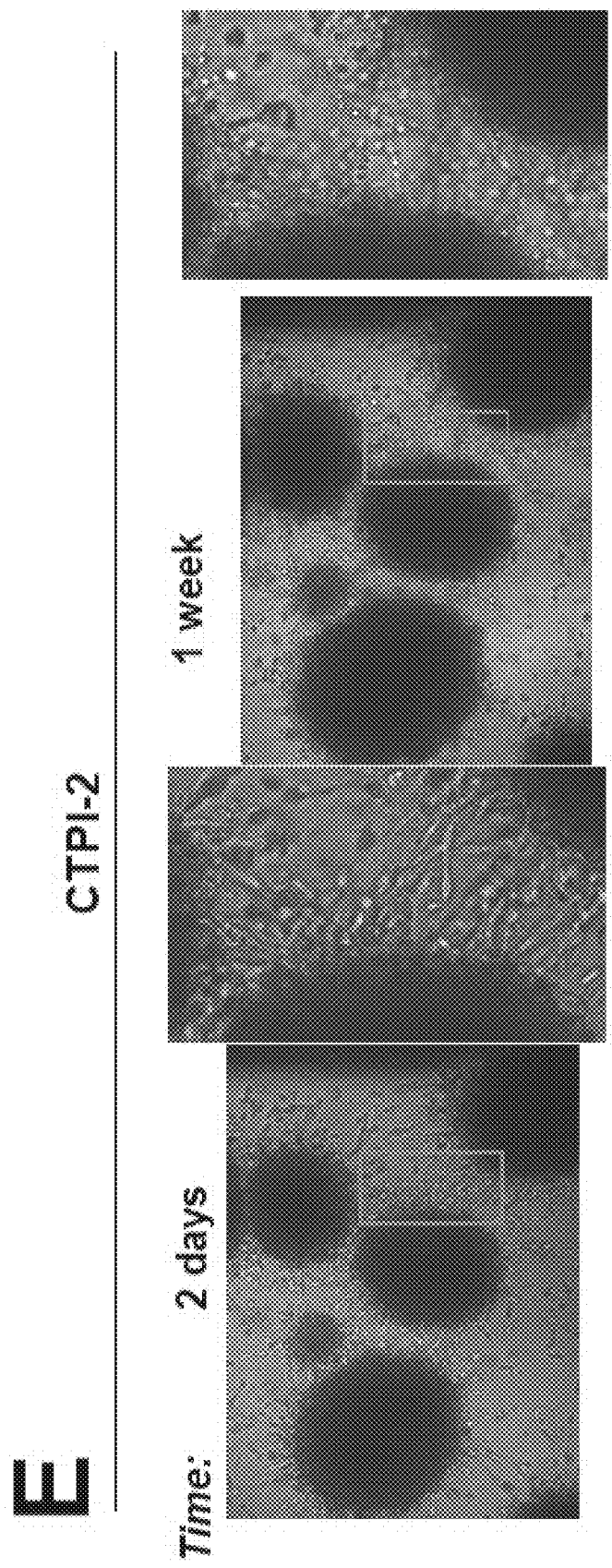
Figure 5F:
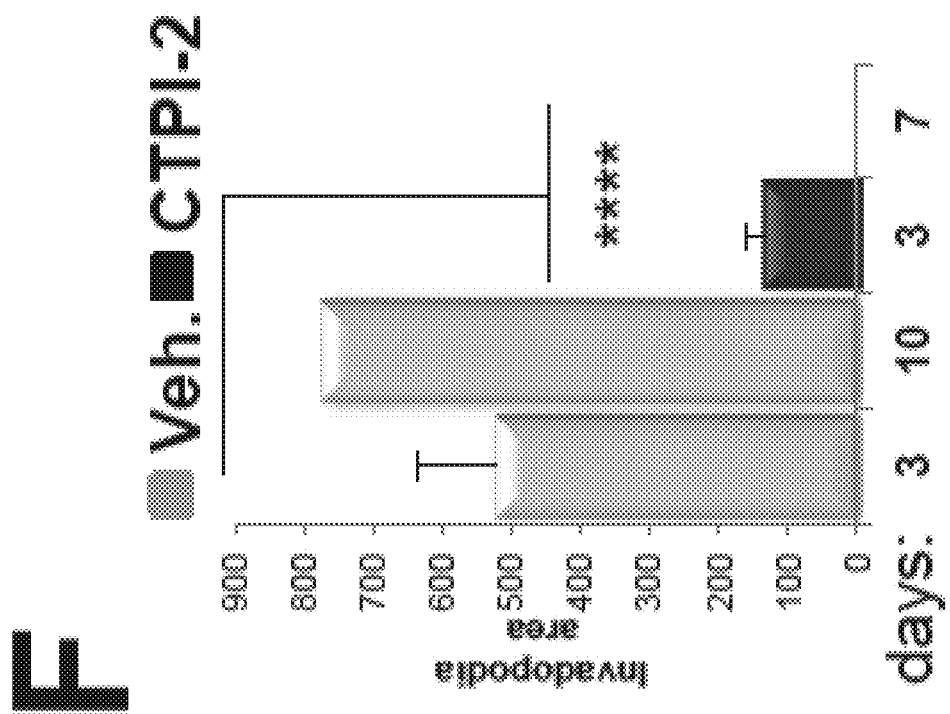
Figure 14E:
Figure 14F:
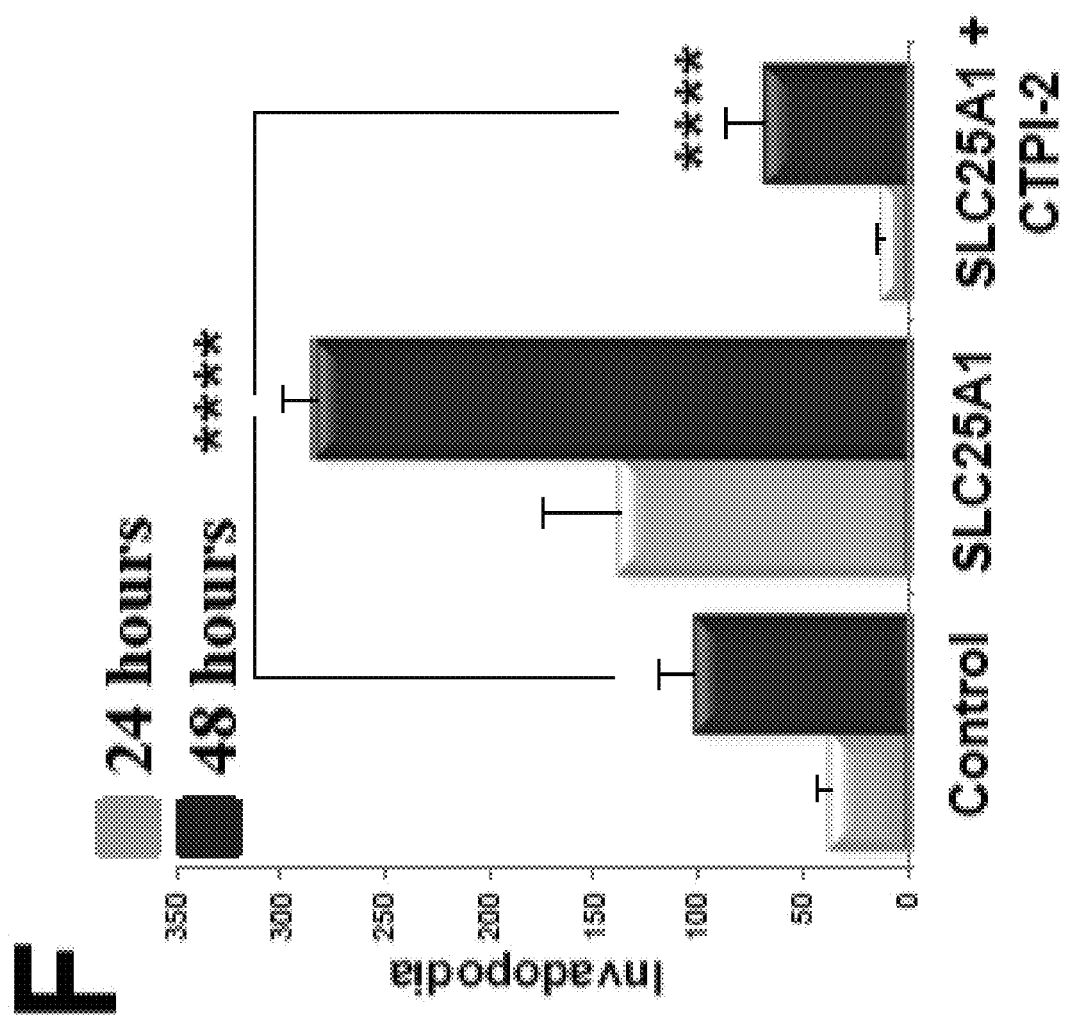

Cancer stem cells become migratory driving tumor infiltration and metastasis and SLC25A1 expression is elevated in metastatic lymph nodes (FIG. 1). By employing a spheroid-based matrix invasion assay that mimics the interaction of tumors with the extracellular matrix, it was found that MP1 tumor spheres were highly invasive in the matrix and CTPI-2 completely reverted this phenotype (FIG. 5E). The expression of SLC25A1 enhanced the ability of lung tumor spheres to invade the matrix (FIG. 14E-F). These results demonstrate that CTPI-2 has broad activity on lung cancer stem cells, inhibiting mitochondrial respiratory activity and matrix invasion.

SLC25A1 drives resistance to cisplatin or AZD9291. The phenotypic plasticity of CSCs that are left behind by conventional therapies plays an important role in the development of resistance. It was determined whether resistant tumors evolve towards a stemness-associated mitochondrial metabolic profile. Clinically, the MP1 tumor showed a partial response to platinum doublet chemotherapy, then the patient progressed towards disseminated disease, indicative of intrinsic primary resistance. The MP2 tumor carries the L858R/T790M mutation which accounts for resistance to first generation EGFR inhibitors (EGFR-i). This mutation can be targeted by selective second generation inhibitors (e.g., dacomitinib) and by third generation EGFR-i that have specificity for the T790M mutation (e.g., osimertinib or AZD9291). However, resistance to third generation EGFR-i has been reported highlighting that advanced tumors with EGFR mutations are often incurable. The patient in this case progressed on dacomitinib and crizotinib (a MET/ALK inhibitor). MP3, a third tumor which also harbors the L858R/T790M and was derived from a patient who progressed on Osimertinib treatment, was expected to be resistant to this drug.

Figure 6A:
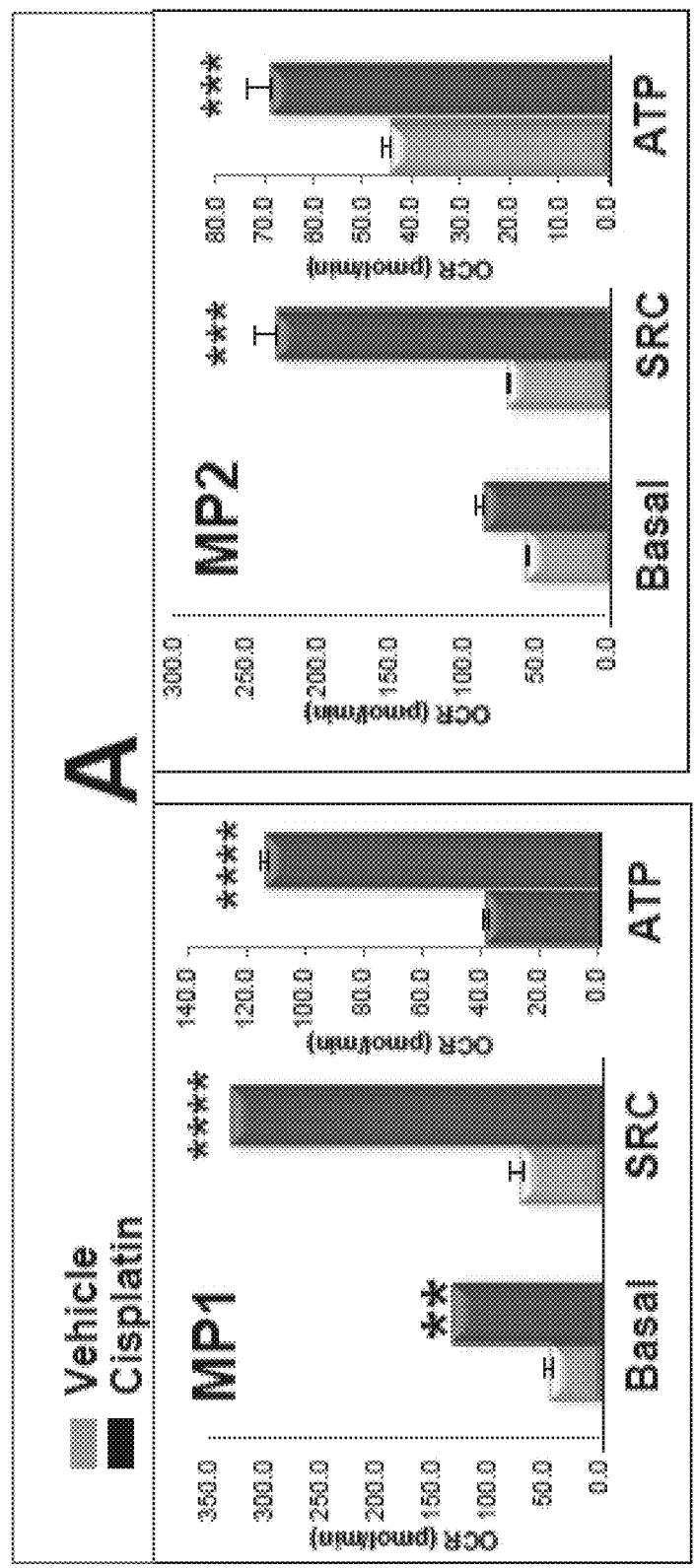
Figure 6D:
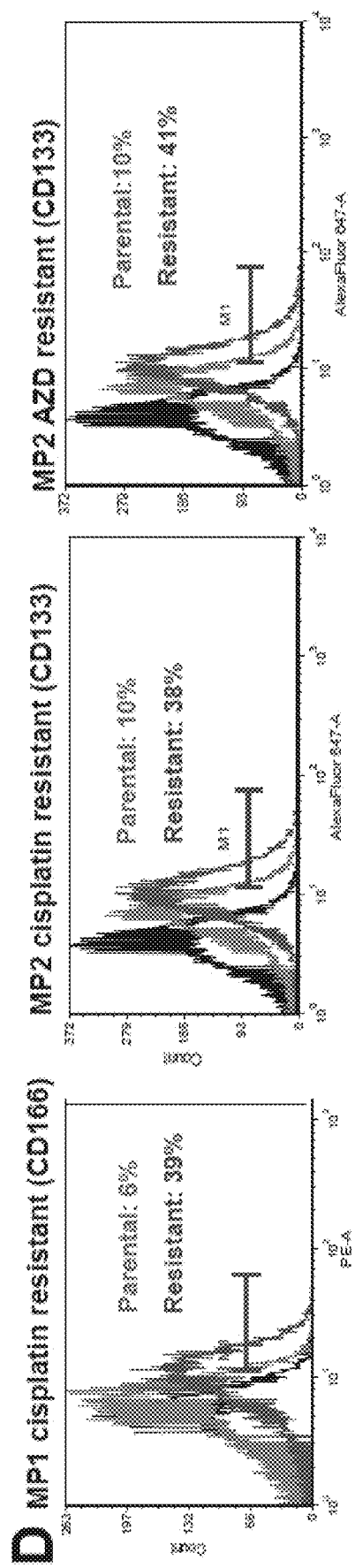

Because of the enrichment of stem cells and the enhanced mitochondrial respiration in CSCs, these experiments were performed in cells grown as monolayers which are more representative of "bulk" tumor cells exposed to the drugs during treatment. The MP1 or MP2 tumor cells were first exposed to chronic treatment with cisplatin or AZD9291 for several passages (FIGS. 6A and 6B, respectively). All treated cells underwent a dramatic shift towards mitochondrial respiration, which in turn starkly improved mitochondrial-derived ATP production, paradoxically indicating a far better energetic output in the presence of these drugs. In the case of the cisplatin treated cells, SLC25A1 expression levels were increased (FIG. 6C) and CTPI-2 blocked basal respiration, SRC and ATP production in these treated cells (FIG. 15A). Further, all of the cisplatin or AZD9291-resistant cells were strongly enriched for stem cell markers (FIG. 6D), supporting that the stemness phenotype is coupled to mitochondrial respiratory activity.

Phenotypically, the MP1, MP2, and MP3 tumor cells maintain the salient characteristics of the tumor of origin with respect to their drug-sensitivity properties, showing a minimal response to either cisplatin or AZD9291 in the case of the MP1 and MP2, and complete insensitivity to AZD9291 in the case of the MP3 (FIG. 6E-G). Most importantly, CTPI-2 re-sensitized the MP1, MP2 and MP3 cells to either cisplatin or AZD9291 treatment in a starkly synergistic fashion (FIG. 6E-G).

To understand the mechanisms by which this sensitization occurs, the extent of apoptosis was studied. While treatment with cisplatin or CTPI-2 alone did not induce apoptosis, a strong pro-apoptotic effect occurred when cells were co-treated with both drugs (FIG. 15B). Given that H1299 cells harboring the SLC25A1 knock-out were more sensitive to cisplatin relative to control cells (FIG. 15C), the combination of these results strongly suggests, for the first time, a synthetic lethal activity of CTPI-2 with cisplatin treatment. As importantly, these effects of CTPI-2 are independent of heterogeneity, because similarly to polyclonal cell populations, a single clone with cisplatin resistance could also be re-sensitized to cisplatin by co-treatment with CTPI-2, becoming even more sensitive than the parental cells (FIG. 15D).

In light of these data, under drug-treatment lung cancer cells switch towards a stemness, likely dormant, phenotype in which they strongly rely upon SLC25A1 activity for mitochondrial respiration, and this metabolic trait allows them to endure the stress of drug treatment in an energetically favorable state (depicted in FIG. 6H). Consequently, in such state they become vulnerable to SLC25A1 inhibitors. The results also highlight the attractive possibility that a common metabolic feature, specifically a switch towards mitochondrial metabolism, hallmarks resistance to different types of therapy, specifically EGFR inhibitors and cisplatin.

Figure 7C:
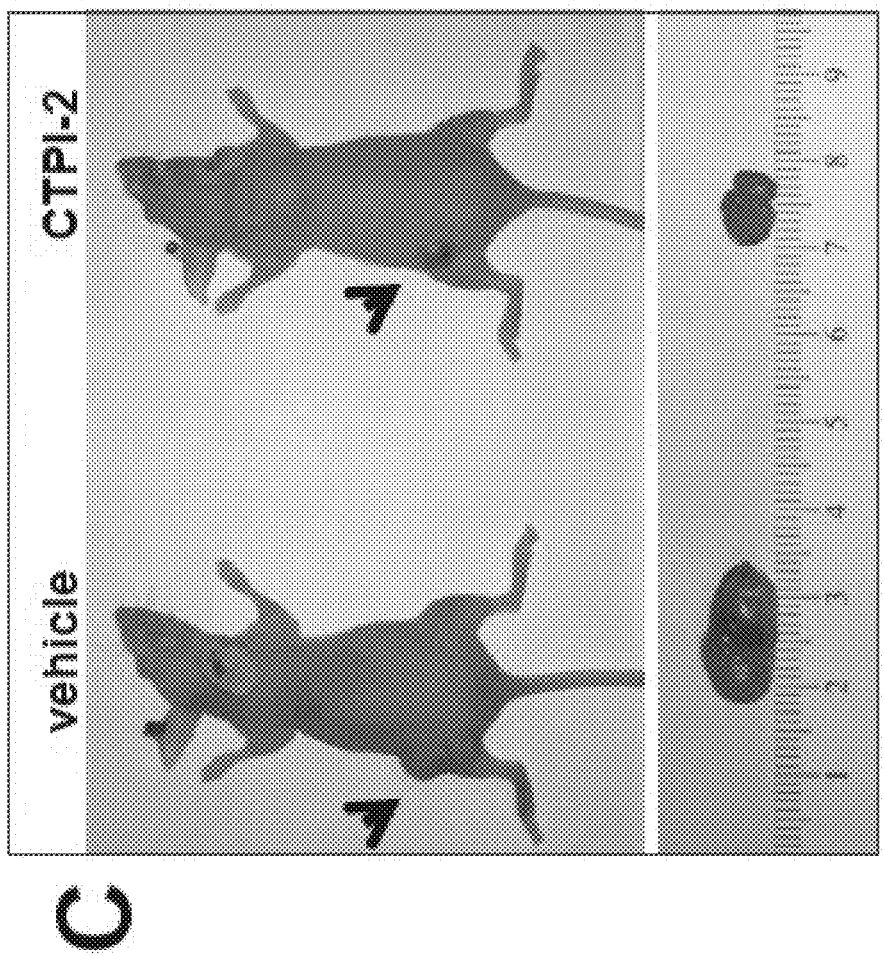

CTPI-2 inhibits tumor growth in pre-clinical models of NSCLC. Several experiments were next performed to assess the therapeutic potential of CTPI-2. First, its activity as single agent in MP1 cells, injected either as monolayer or as GMSC-spheres in immuno-compromised mice, was studied. CTPI-2 was administered at 26 mg/Kg at alternate days intra-peritoneally after tumors had reached a size of 50-100 mm$^3$. At this dose, CTPI-2 was well tolerated during the entire treatment period and body weights remained unchanged, suggesting that the maximum tolerated dose had not been reached at this treatment regimen. Injection of MP1 cells derived from monolayer cultures resulted in engraftment of 50% and tumors arose with a latency of three weeks, in comparison with cells derived from GMSC-grown spheres that generated tumors with 100% frequency and a latency of less than one week (FIG. 7A), consistent with the enrichment of stem cells with tumor initiating capability herein. CTPI-2 was more effective in inhibiting the growth of GMSC-derived MP1 tumors relative to tumors derived from differentiated monolayer cultures (FIG. 7B-C).

Figure 7D:
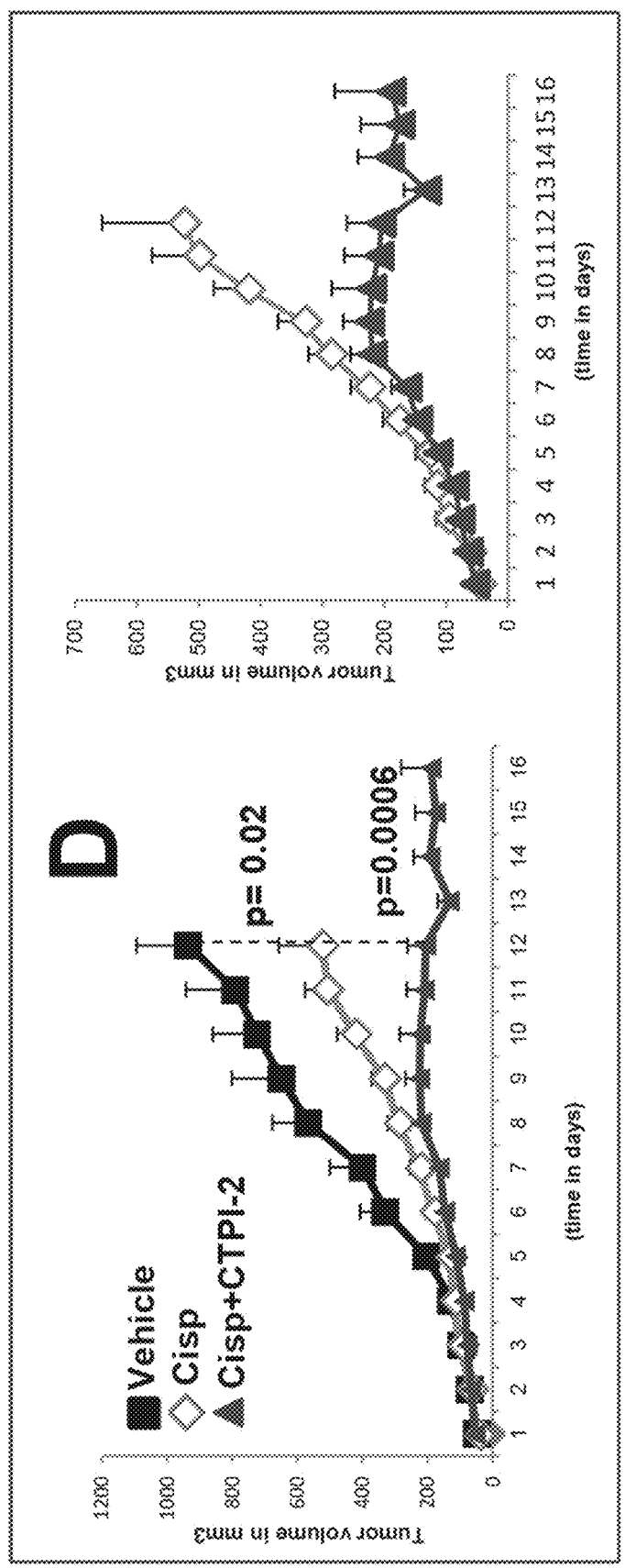
Figure 7E:
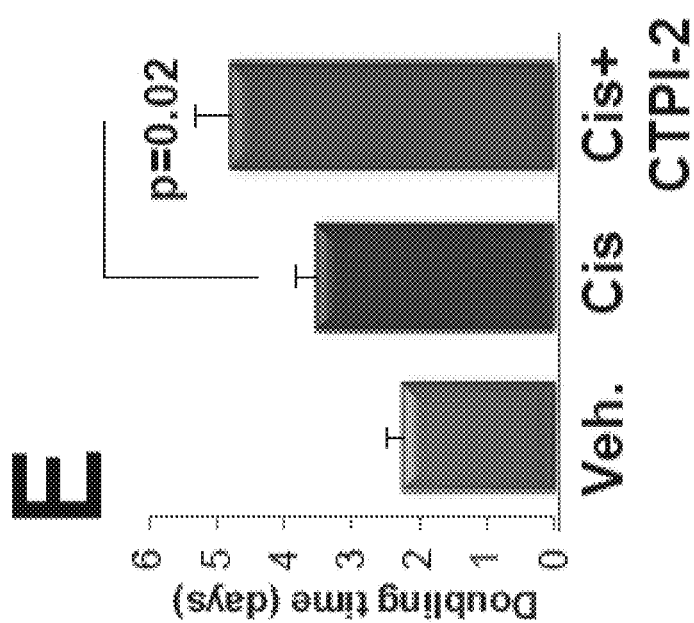

In keeping with the results obtained in vitro (FIG. 6), the effects of CTPI-2 in combination therapy with either cisplatin in MP1 cells or AZD9291 in MP2 cells were determined. As shown in FIG. 7D, cisplatin treatment alone resulted in inhibition of tumor growth but this effect was lost over time, and most tumors restarted to grow within two weeks of treatment. This response is similar to that observed in the patient who showed a partial response to platinum therapy then followed by progressive disease. When CTPI-2 was added to the cisplatin regimen, tumor growth inhibition was very significant and it was sustained for a longer period of time compared to cisplatin alone. Consistent with this pattern, CTPI-2 significantly extended the tumor doubling times relatively to the mock- and the cisplatin-treated groups, indicative of a better response (FIG. 7E). The immuno-blot analysis of these tumors showed an enrichment of stem cell markers in GMSC-grown cells which was enhanced by cisplatin treatment (FIG. 7F, compare lane 1 versus 2, and lane 2 versus 3, respectively), consistent with previous observations that cisplatin selects for the emergence of resistant CSC populations (FIG. 6). Treatment with CTPI-2 led instead to a dramatic reduction in the levels of these markers (lane 4). These results provide a molecular basis for the efficacy of co-treatment with these drugs. Consistent with the in vitro data (FIG. 6F), co-treatment with CTPI-2 and AZD9291 also led to a prominent enhancement of tumor growth inhibition relative to AZD9291 treatment alone (FIG. 7G).

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods and combinations of various features of the compositions and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method of treating cancer in a subject, comprising: administering to the subject an effective amount of a compound of the following structure:

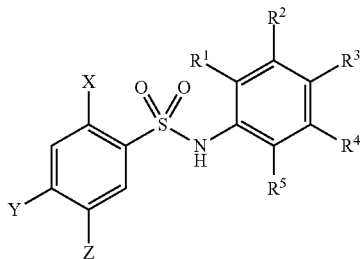

or a pharmaceutically acceptable salt thereof, wherein:
$R^1$, $R^2$, $R^3$, $R^4$, and X are each independently selected from the group consisting of hydrogen, halogen, nitro, hydroxy, amino, alkoxy, substituted or unsubstituted carbonyl, substituted or unsubstituted alkyl, substituted or unsubstituted alkenyl, and substituted or unsubstituted alkynyl, Y is selected from the group consisting of halogen, nitro, hydroxy, amino, alkoxy, substituted or unsubstituted carbonyl, substituted or unsubstituted alkyl, substituted or unsubstituted alkenyl, and substituted or unsubstituted alkynyl, Z is selected from the group consisting of halogen, nitro, hydroxy, amino, alkoxy, substituted or unsubstituted carbonyl, substituted or unsubstituted alkyl, substituted or unsubstituted alkenyl, and substituted or unsubstituted alkynyl, and $R^5$ is selected from the group consisting of halogen, nitro, hydroxy, amino, alkoxy, substituted or unsubstituted carbonyl, substituted or unsubstituted alkyl, substituted or unsubstituted alkenyl, and substituted or unsubstituted alkynyl.

2. The method of claim 1, wherein X is hydrogen.
3. The method of claim 1, wherein Y is chloro.
4. The method of claim 1, wherein Z is nitro.
5. The method of claim 1, wherein $R^5$ is —$CO_2H$.
6. The method of claim 1, wherein the compound is

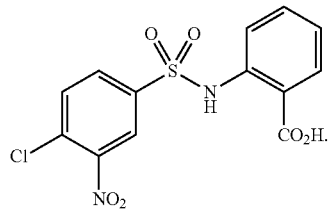 [SMILES: O=C(O)c1ccccc1NS(=O)(=O)c1ccc(Cl)c([N+](=O)[O-])c1]

7. The method of claim 1, further comprising administering a second therapeutic agent to the subject.
8. The method of claim 7, wherein the second therapeutic agent is a chemotherapeutic agent.
9. The method of claim 8, wherein the chemotherapeutic agent is an epidermal growth factor receptor (EGFR) inhibitor.
10. The method of claim 9, wherein the EGFR inhibitor is selected from the group consisting of gefitinib, erlotinib, lapatinib, cetuximab, panitumumab, vandetanib, necitumumab, and osimertinib.
11. The method of claim 1, wherein the cancer is lung cancer, breast cancer, or colon cancer.
12. The method of claim 1, wherein the cancer is a cisplatin-resistant cancer or an EGFR inhibitor-resistant cancer.
13. A method of treating cancer in a subject, comprising: administering to the subject an effective amount of a compound of the following structure:

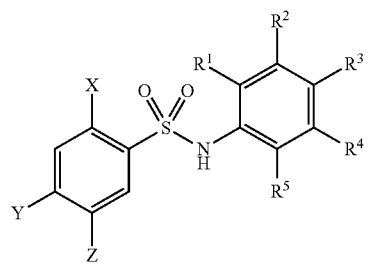

or a pharmaceutically acceptable salt thereof, wherein:
$R^1$, $R^2$, $R^3$, $R^4$, and X are each independently selected from the group consisting of hydrogen, halogen, nitro, hydroxy, amino, alkoxy, substituted or unsubstituted carbonyl, substituted or unsubstituted alkyl, substituted or unsubstituted alkenyl, and substituted or unsubstituted alkynyl, Y is selected from the group consisting of halogen, nitro, hydroxy, amino, alkoxy, substituted or unsubstituted carbonyl, substituted or unsubstituted alkyl, substituted or unsubstituted alkenyl, and substituted or unsubstituted alkynyl, Z is selected from the group consisting of halogen, nitro, hydroxy, amino, alkoxy, substituted or unsubstituted carbonyl, substituted or unsubstituted alkyl, substituted or unsubstituted alkenyl, and substituted or unsubstituted alkynyl, and $R^5$ is selected from the group consisting of halogen, nitro, hydroxy, amino, alkoxy, substituted or unsubstituted carbonyl, substituted or unsubstituted alkyl, substituted or unsubstituted alkenyl, and substituted or unsubstituted alkynyl, wherein $R^1$, $R^4$, and X are not simultaneously hydrogen.

* * * * *